United States Patent
Won et al.

(10) Patent No.: US 10,327,715 B2
(45) Date of Patent: Jun. 25, 2019

(54) SYSTEM AND METHOD OF PROVIDING INFORMATION OF PERIPHERAL DEVICE

(71) Applicant: Samsung Electronics Co., Ltd., Suwon-si, Gyeonggi-do (KR)

(72) Inventors: Ji-seon Won, Suwon-si (KR); Yong Kim, Seoul (KR); Jing-sung Kim, Seoul (KR); Hwa-kyung Kim, Seoul (KR); Jong-youb Ryu, Suwon-si (KR); Kyoung-jin Moon, Suwon-si (KR); Chang-hyun Lee, Suwon-si (KR); Yong-hyun Lim, Suwon-si (KR); Hae-in Chun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 325 days.

(21) Appl. No.: 15/184,437

(22) Filed: Jun. 16, 2016

(65) Prior Publication Data
US 2016/0367204 A1 Dec. 22, 2016

(30) Foreign Application Priority Data
Jun. 16, 2015 (KR) ........................ 10-2015-0085141

(51) Int. Cl.
*A61B 5/0482* (2006.01)
*A61B 5/04* (2006.01)
*A61B 5/00* (2006.01)
*A61B 5/16* (2006.01)
*A61F 4/00* (2006.01)

(52) U.S. Cl.
CPC .......... *A61B 5/747* (2013.01); *A61B 5/04012* (2013.01); *A61B 5/0482* (2013.01); *A61B 5/165* (2013.01); *A61B 5/4088* (2013.01); *A61B 5/6803* (2013.01); *A61B 5/742* (2013.01); *A61B 5/7405* (2013.01); *A61B 5/746* (2013.01); *A61F 4/00* (2013.01)

(58) Field of Classification Search
None
See application file for complete search history.

(56) References Cited

U.S. PATENT DOCUMENTS

| | | | |
|---|---|---|---|
| 8,510,166 B2 | 8/2013 | Neven | |
| 2010/0094097 A1 | 4/2010 | Liu et al. | |
| 2011/0050707 A1 | 3/2011 | Kim et al. | |
| 2011/0137137 A1 | 6/2011 | Shin et al. | |
| 2011/0144520 A1* | 6/2011 | Causevic | A61B 5/0476 600/544 |
| 2012/0136274 A1* | 5/2012 | Burdea | A61B 5/04842 600/545 |
| 2013/0303837 A1* | 11/2013 | Berka | A61B 5/0476 600/28 |
| 2014/0139551 A1 | 5/2014 | McCulloch et al. | |
| 2015/0058804 A1 | 2/2015 | Kim | |
| 2015/0095088 A1 | 4/2015 | Dabbiru et al. | |

FOREIGN PATENT DOCUMENTS

| | | | | |
|---|---|---|---|---|
| WO | 01-54043 A1 | 7/2001 | | |
| WO | WO 2014102722 A1 * | 7/2014 | ........... | H04L 9/3231 |
| WO | 2015-080360 A1 | 6/2015 | | |

* cited by examiner

*Primary Examiner* — Etsub D Berhanu
(74) *Attorney, Agent, or Firm* — Jefferson IP Law, LLP

(57) ABSTRACT

Provided is a device for detecting stress of a user based on a bio-signal of the user, and when the stress is detected, outputting information of a peripheral device.

14 Claims, 32 Drawing Sheets

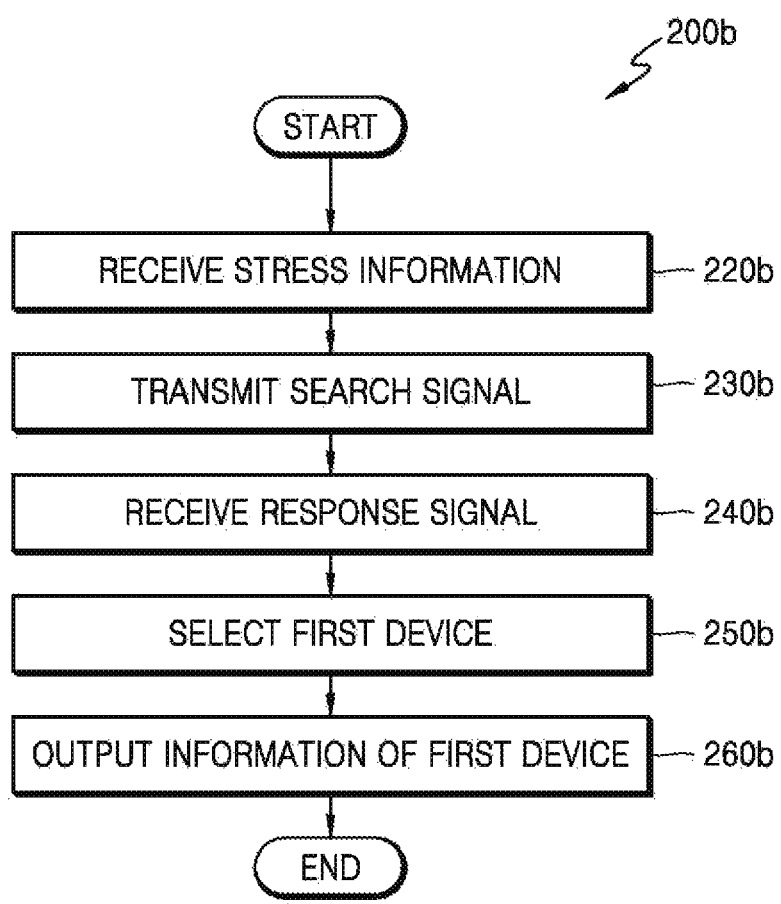

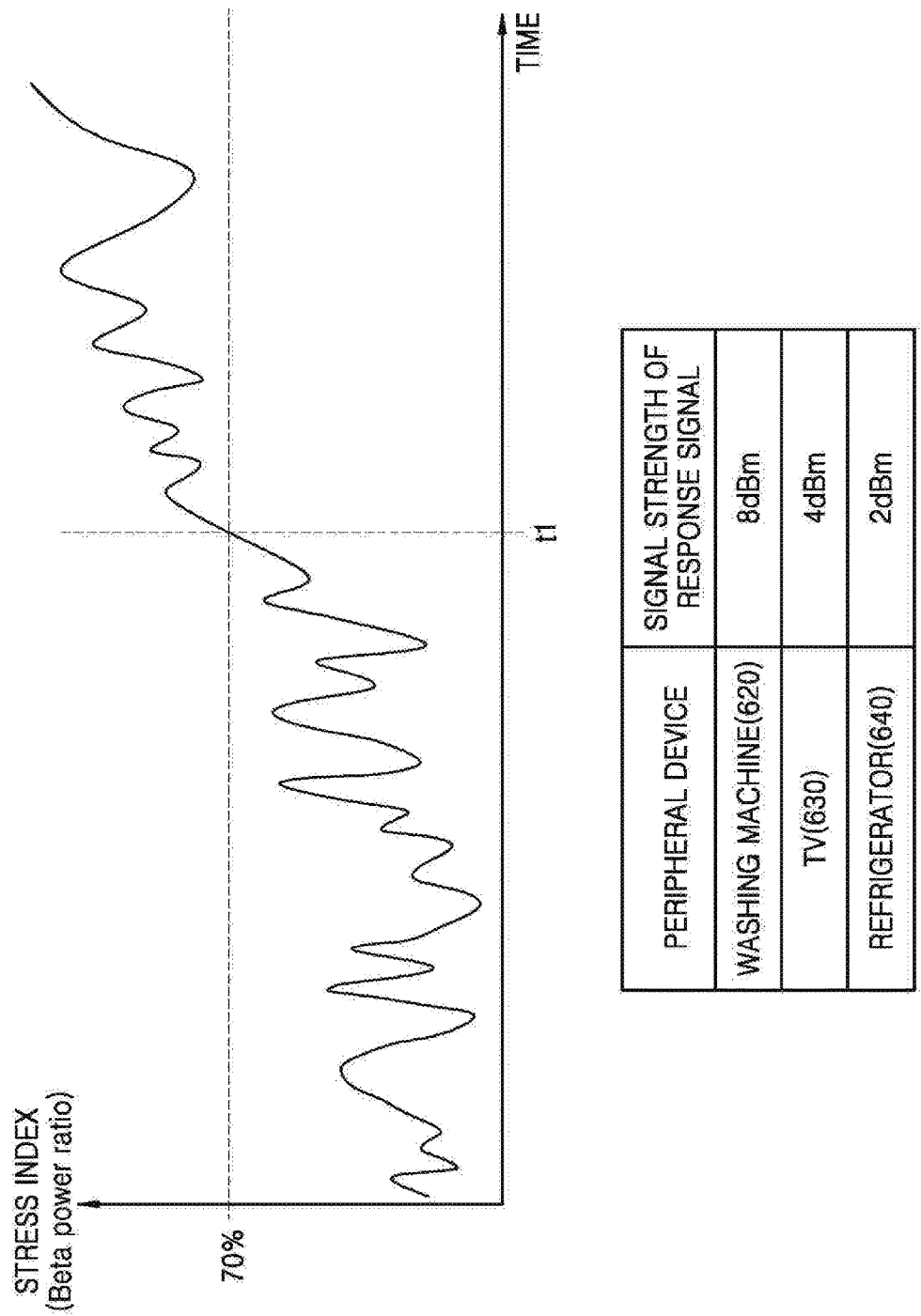

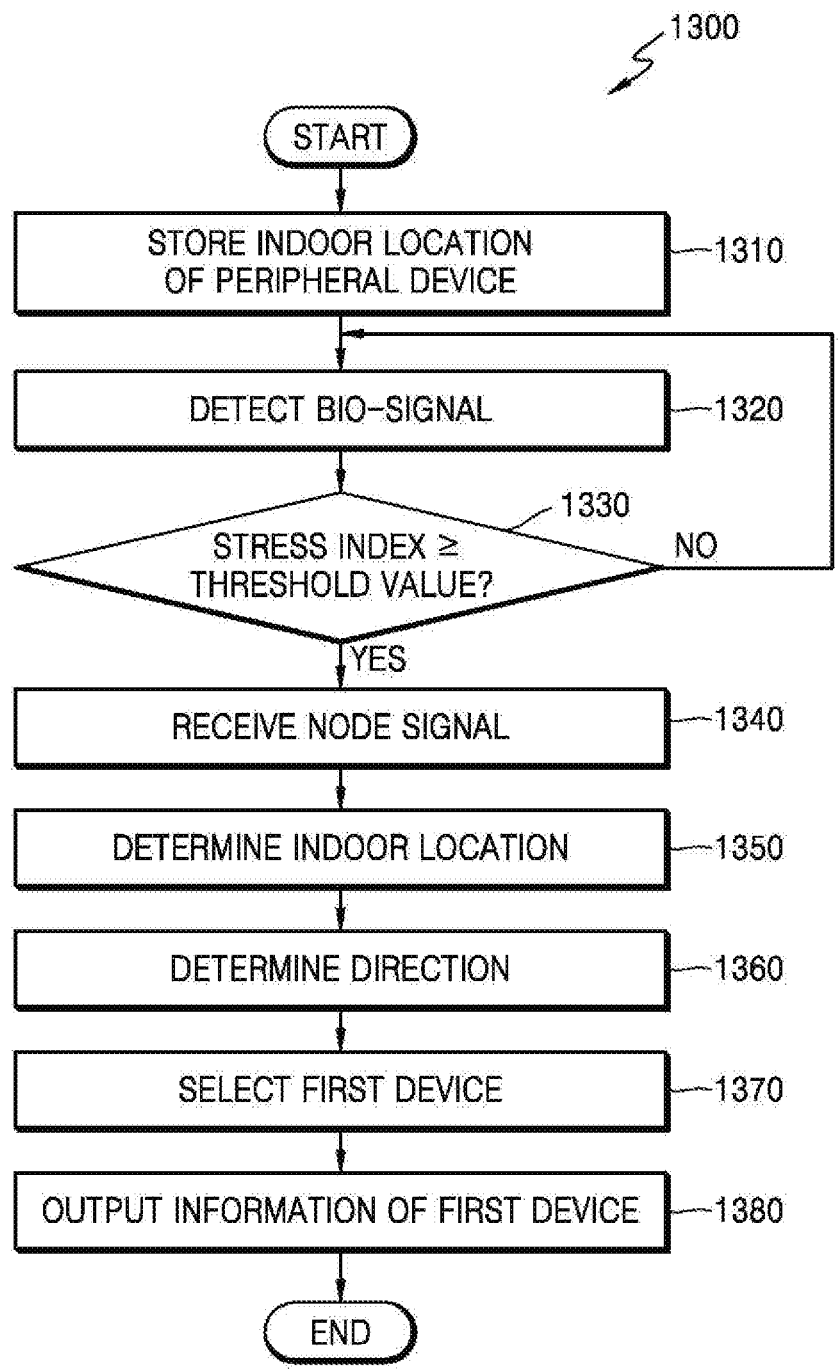

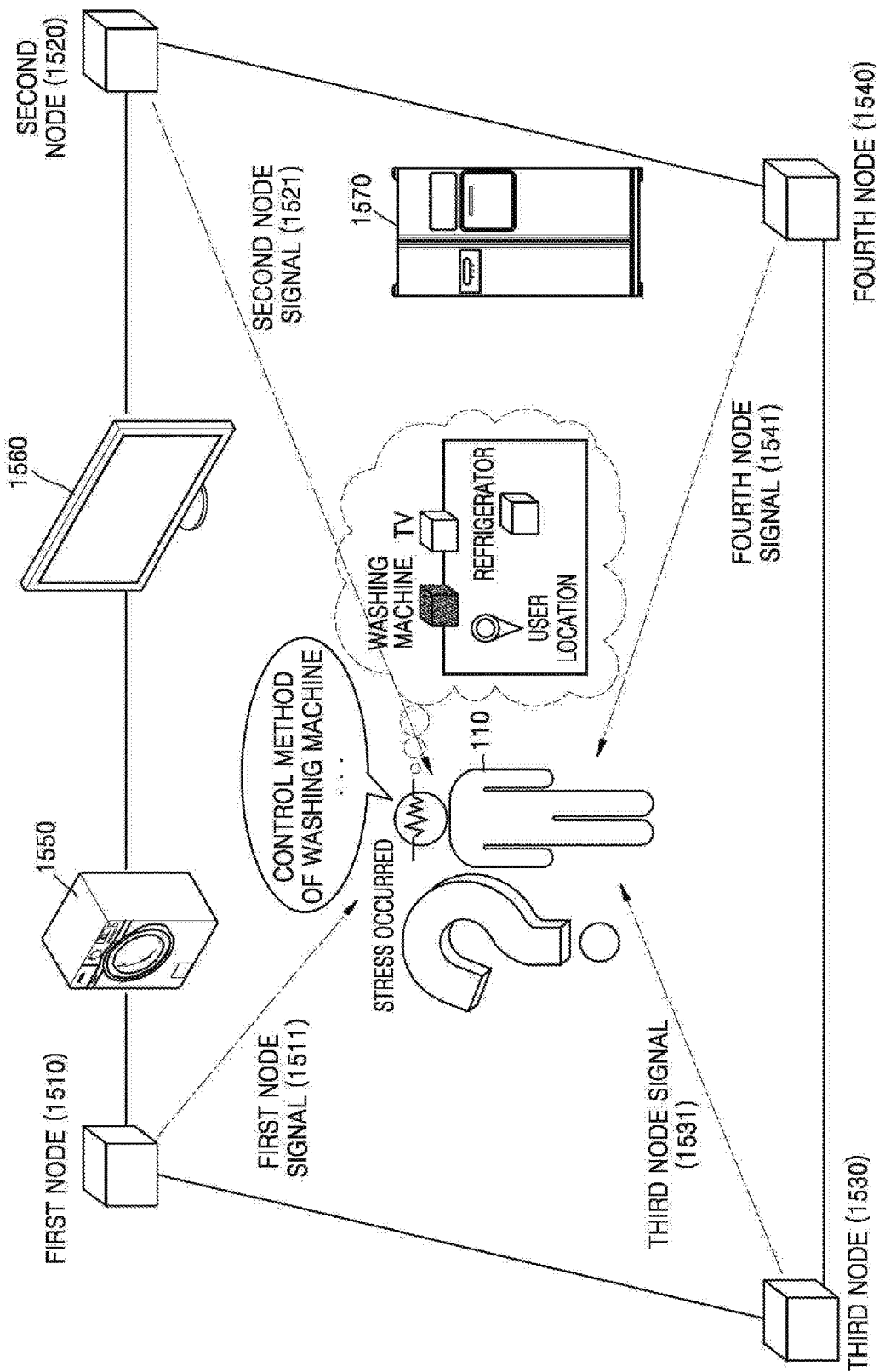

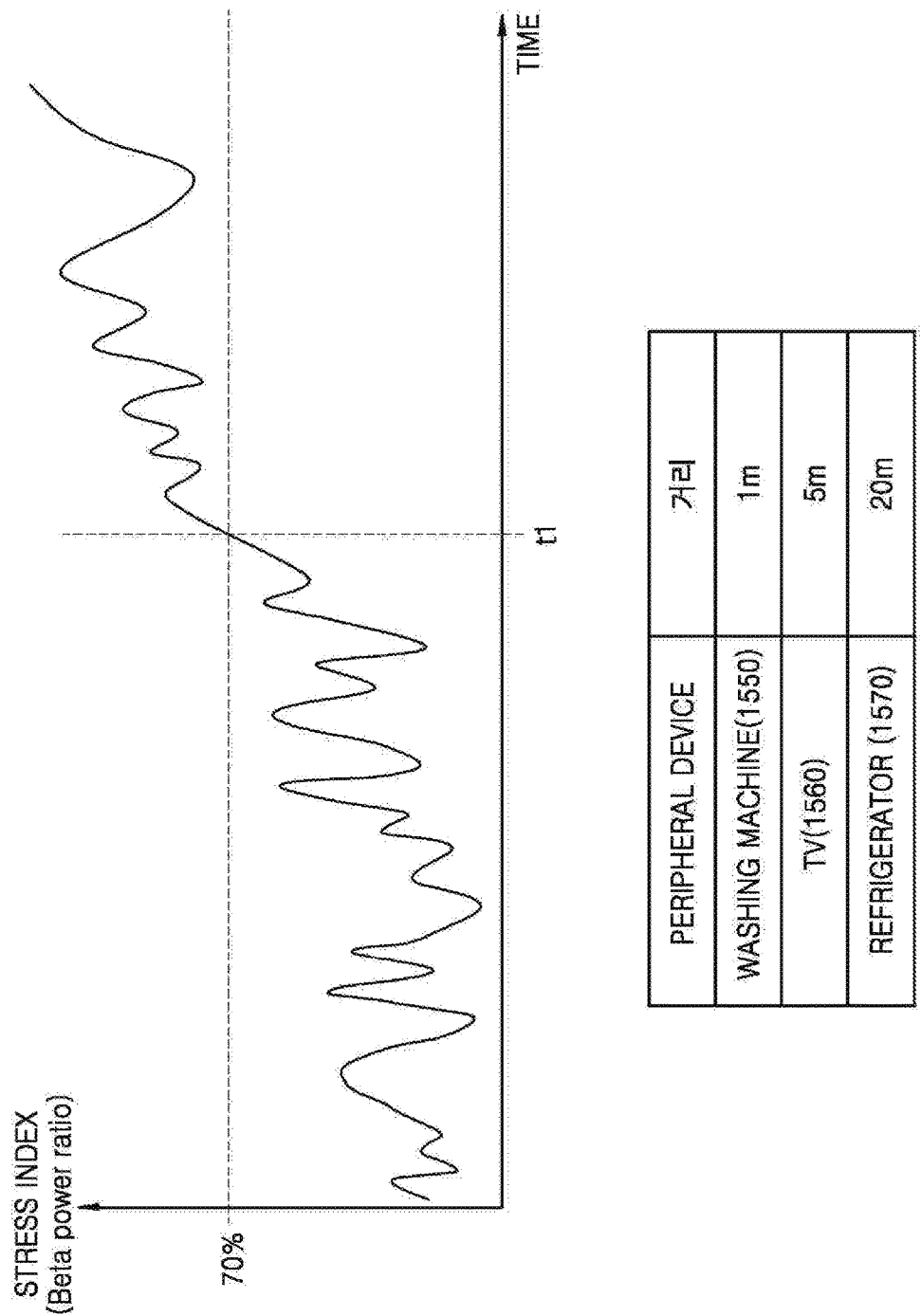

SYSTEM AND METHOD OF PROVIDING INFORMATION OF PERIPHERAL DEVICE

CROSS-REFERENCE TO RELATED APPLICATION(S)

This application claims the benefit under 35 U.S.C. § 119(a) of a Korean patent application filed on Jun. 16, 2015 in the Korean Intellectual Property Office and assigned Serial number 10-2015-0085141, the entire disclosure of which is hereby incorporated by reference.

TECHNICAL FIELD

The present disclosure relates to a system and method of outputting information of a peripheral device according to stress of a user.

BACKGROUND

Most dementia patients suffer from memory loss in the early stages of dementia. Dementia patients who suffer from memory loss are unable to recognize a person or an object, or to find a way. Accordingly, it is difficult for the dementia patients to live a normal life without help from other people. Generally, since the dementia patients need to notify other people about their memory loss to ask them for help, the dementia patients may feel shame or humiliation.

Accordingly, a technology for helping dementia patients to live a normal life without help from other people is required.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an apparatus and method for determining whether a user is stressed out based on a bio-signal of the user and outputting information of a peripheral device of the user when it is determined that the user is stressed out.

Additional aspects will be set forth in part in the description which follows and, in part, will be apparent from the description, or may be learned by practice of the presented embodiments.

In accordance with an aspect of the present disclosure, a device is provided. The device includes a sensor configured to detect a bio-signal of a user, a communicator configured to communicate with at least one peripheral device, a processor configured to calculate a stress index of the user based on the bio-signal, and when the stress index is equal to or higher than a threshold value, search for the at least one peripheral device and select a first device from among the at least one peripheral device, and an outputter configured to output information of the first device, wherein the processor is configured to transmit a search signal to the at least one peripheral device by using the communicator and search for the peripheral device by receiving a response signal from the peripheral device.

The processor may be configured to transmit the search signal in a pre-set direction by using the communicator.

The bio-signal may include electroencephalography (EEG).

The processor may be configured to output the information of the first device as at least one of visual information and auditory information by using the outputter.

The information of the first device may include guide information corresponding to execution of a function of the first device.

When the first device is a dangerous device, the processor may be configured to output a warning signal by using the outputter.

When the first device is a dangerous device, the processor may be configured to transmit a notification to a pre-set contact number by using the communicator.

In accordance with another aspect of the present disclosure, a method is provided. The method includes detecting a bio-signal of a user, calculating a stress index of the user based on the bio-signal, when the stress index is equal to or higher than a threshold value, transmitting a search signal to at least one peripheral device and searching for the peripheral device by receiving a response signal from the peripheral device, selecting a first device from among at least one found peripheral device, and outputting information of the first device.

The search signal may be transmitted in a pre-set direction.

The bio-signal may include EEG.

The information of the first device may be output as at least one of voice or sound.

The information of the first device may include guide information corresponding to execution of a function of the first device.

The method may further include, when the first device is a dangerous device, outputting a warning signal.

The method may further include, when the first device is a dangerous device, transmitting a notification to a pre-set contact number.

In accordance with another aspect of the present disclosure, a device is provided. The device includes a sensor configured to detect a bio-signal of a user, a communicator configured to communicate with a node at home, a storage unit configured to store indoor location information of at least one peripheral device, a processor configured to calculate a stress index of the user based on the bio-signal, and when the stress index is equal to or higher than a threshold value, select a first device from among the at least one peripheral device by using an indoor location of a device determined via communication with the node, and an outputter configured to output information of the first device.

The processor may be configured to determine the indoor location of the device based on a node signal received from the node and select the first device by comparing the indoor location of the device with an indoor location of the at least one peripheral device.

The processor may be configured to determine the indoor location of the device based on a magnetic field detected from the device.

In accordance with another aspect of the present disclosure, a device is provided. The device includes a sensor configured to detect a bio-signal of a user, an imaging unit configured to capture an image of a surrounding person or object, a processor configured to calculate a stress index of the user based on the bio-signal, and when the stress index is equal to or higher than a threshold value, search for the surrounding person or object by using the captured image, and an outputter configured to output information of a found surrounding person or object.

The processor may be configured to search for the surrounding person or object by comparing the captured image with an image of the surrounding person or object pre-stored in the device.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 2B is a flowchart of a method of searching for, by a device, a peripheral device based on a search signal and a response signal, and outputting information of the peripheral device, according to an embodiment of the present disclosure;

FIGS. 6A and 6B are diagrams for describing an operation of searching for, by a device, peripheral devices based on a broadcasting method, according to various embodiments of the present disclosure;

FIG. 13 is a flowchart of a method of determining, by a device, an indoor location, detecting a direction of the device, selecting a first device, and outputting information of the first device, according to an embodiment of the present disclosure;

FIGS. 15A and 15B are diagrams for describing a device determining an indoor location of the device and searching for peripheral devices, according to various embodiments of the present disclosure;

Throughout the drawings, like reference numerals will be understood to refer to like parts, components, and structures.

DETAILED DESCRIPTION

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the specification, when a region is "connected" to another region, the regions may not only be "directly connected", but may also be "electrically connected" via another device therebetween. Also, when a region "includes" an element, the region may further include another element instead of excluding the other element, otherwise differently stated.

As used herein, the singular forms "a," "an", and "the" are intended to include the plural forms as well, unless the context clearly indicates otherwise.

Expressions such as "at least one of", when preceding a list of elements, modify the entire list of elements and do not modify the individual elements of the list.

Hereinafter, one or more embodiments will be described with reference to accompanying drawings.

Figure 1:
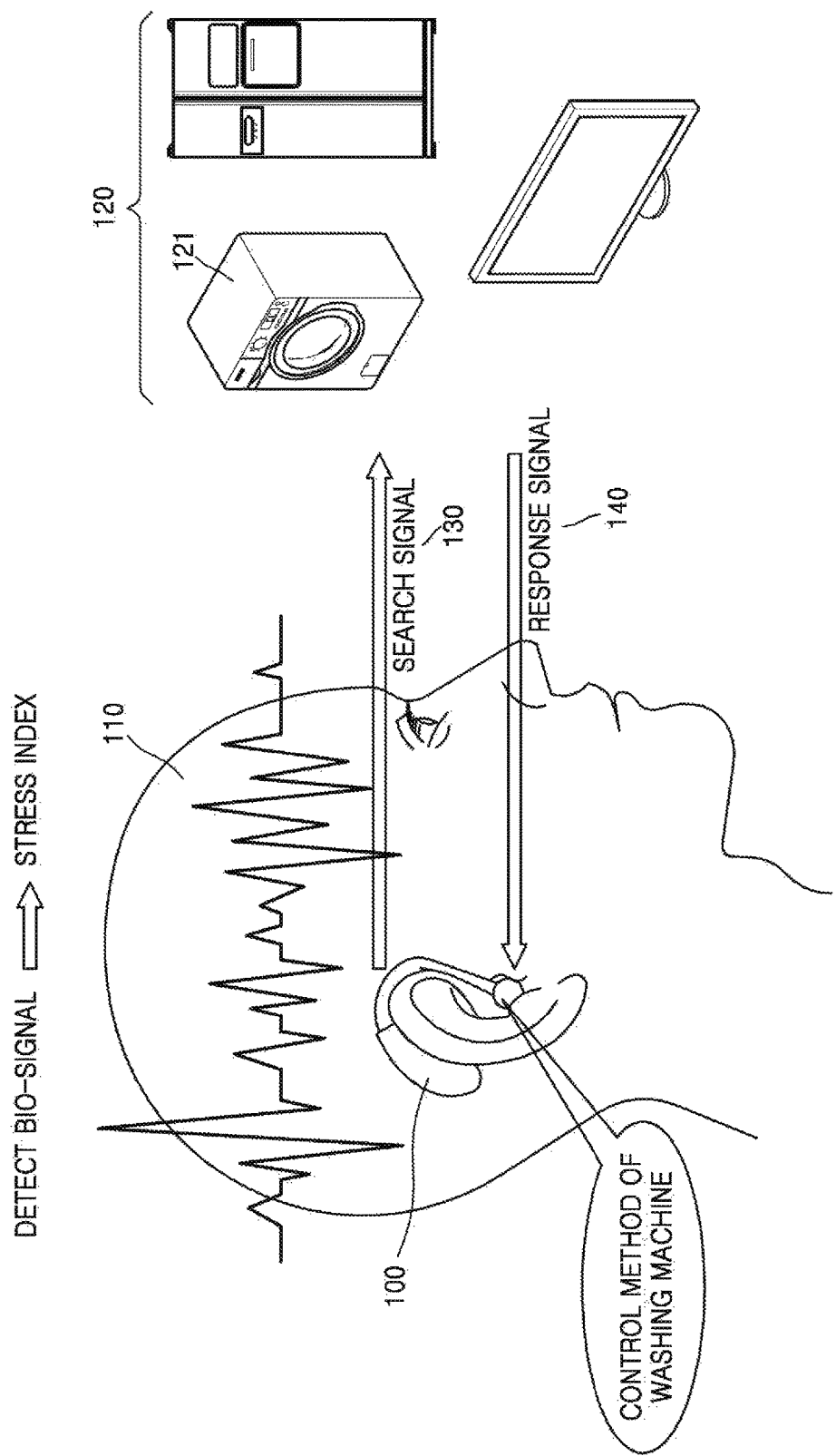
FIG. 1 illustrates a system for outputting information of at least one peripheral device, according to an embodiment of the present disclosure.

FIG. 1 illustrates a system for outputting information of at least one peripheral device 120, according to an embodiment of the present disclosure.

Referring to FIG. 1, the system may include the at least one peripheral device 120 and a device 100 outputting information of the at least one peripheral device 120.

The device 100 may be an electronic apparatus carried by a user 110. For example, the device 100 may be a wearable device, an implantable device, or a mobile device.

Here, a wearable device may be a device that is worn on a body of the user 110 and performs computing operations. For example, the wearable device may have any form wearable by the user 110, such as a hearing aid, an earphone, glasses, goggles, a helmet, a hair band, a head-mounted device (HMD), a bracelet, a ring, a necklace, a shoe, a belt, a sticker, or a clip.

An implantable device may be a device that is implanted into the body of the user 110 and performs computing operations. For example, the implantable device may have any form that may be inserted behind an ear, into a wrist, or into the chest of the user 110.

A mobile device may be a device that is sufficiently small to be carried by the user 110 and performs computing operations. For example, the mobile device may be a mobile phone, a tablet personal computer (PC), or a laptop.

The device 100 may detect a bio-signal of the user 110. The device 100 may calculate a stress index of the user 110 based on the bio-signal, and search for the at least one peripheral device 120 when the stress index is equal to or higher than a threshold value.

The peripheral device 120 may be an external device located around the device 100 and may be, for example, a consumer electronics (CE) device, an electronic device, a home device, or a mobile device. The peripheral device 120 may stress the user 110. Referring to FIG. 1, a washing machine 121, a television (TV), and a refrigerator are shown as examples of the peripheral devices 120.

The device 100 may select one peripheral device from among the at least one peripheral device 120 and output information of the selected peripheral device. For example, the information of the selected peripheral device may include guide information corresponding to execution of a function of the selected peripheral device. In detail, the information of the selected peripheral device may include information about a control method for executing a pre-set function of the selected peripheral device.

For example, referring to FIG. 1, the user 110, who is a dementia patient, may be wearing the device 100 of a hearing aid type. Also, the user 110 may want to use the washing machine 121, but may not remember how to use the washing machine 121 due to memory loss. The device 100 may detect electroencephalography (EEG) β waves of the user 110 and calculate the stress index of the user 110, caused by the memory loss, based on the EEG β waves. Also, when the stress index is equal to or higher than a threshold value, the device 100 may search for the at least one peripheral device 120. The device 100 may select the washing machine 121 from among the at least one peripheral device 120. Also, the device 100 may output information about a control method of the washing machine 121 (i.e., information of a peripheral device) as a voice.

The user 110 may listen to the information output from the device 100 and manipulate the washing machine 121 without help from other people, despite intermittent memory loss.

Figure 2A:
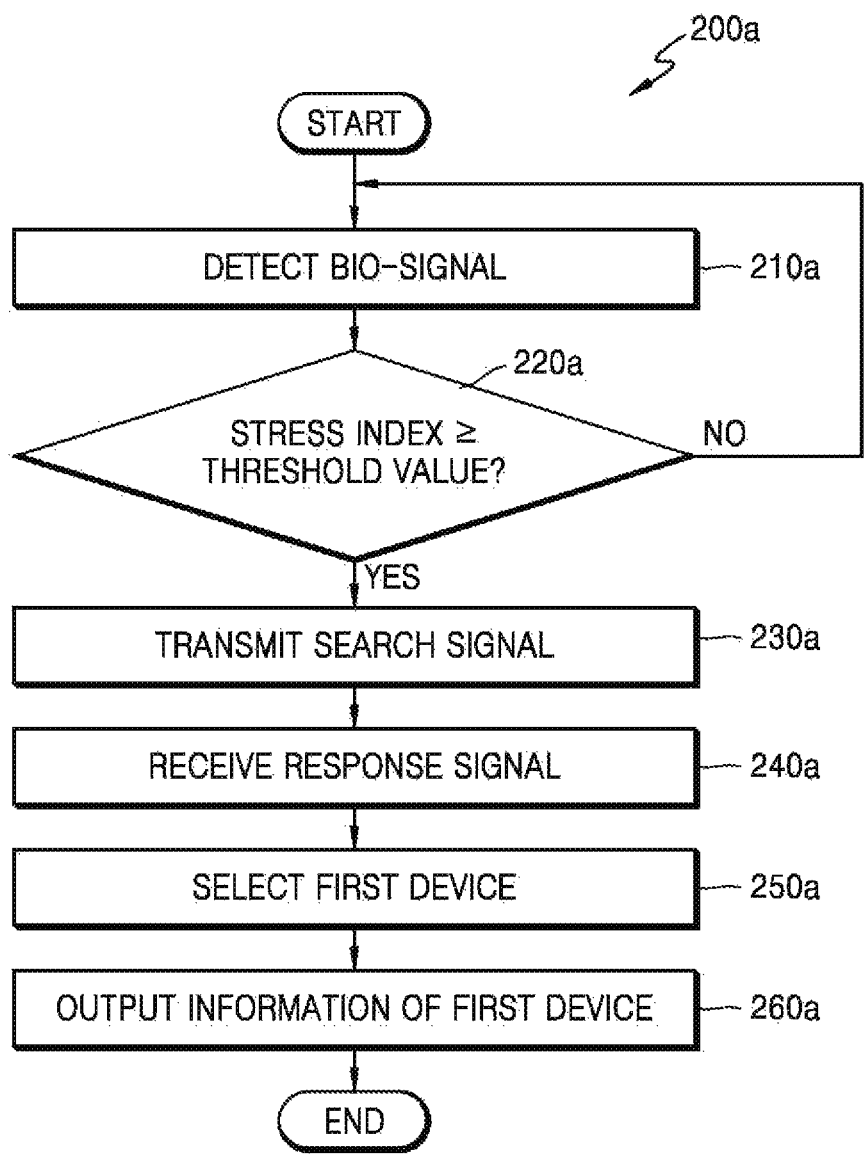
FIG. 2A is a flowchart of a method of searching for, by a device, a peripheral device based on a search signal and a response signal, and outputting, by the device, information of the peripheral device, according to an embodiment of the present disclosure.

FIG. 2A is a flowchart of a method 200a of searching for, by the device 100, the peripheral device 120 based on a search signal 130 and a response signal 140, and outputting, by the device 100, information of the peripheral device 120, according to an embodiment of the present disclosure.

In operation 210a, the device 100 may detect a bio-signal of the user 110.

The device 100 may detect the bio-signal of the user 110 by using a sensor in the device 100. The bio-signal of the user 110 may be an electric or non-electric signal detected or measured from the user 110. The bio-signal may be continuously or periodically detected. Also, a value of the bio-signal may change according to time. The device 100 may detect, from the user 110, at least one of EEG, brainwaves, electrocardiography (ECG), the heartbeat, a body temperature, blood pressure, a pupil, hemoglobin saturation, skin conductivity, respiration, perspiration, and a voice signal, by using the sensor in the device 100.

The bio-signal detected by the device 100 may vary depending on a body portion of the user 110, where the device 100 is worn, or depending on types of the sensor included in the device 100.

For example, when the device 100 is a wearable device worn on an ear of the user 110, such as a hearing aid or an earphone, the device 100 may detect EEG near an inner ear, an external ear, behind the ear, or a mastoid. As well as the EEG, the device 100 worn on the ear may detect a body temperature from the inner ear or detect the heartbeat from the carotid behind the ear.

In operation 220a, the device 100 may calculate a stress index of the user 110 based on the bio-signal and determine whether the stress index is equal to or higher than a threshold value.

Here, stress of the user 110 may include at least one of mental stress and physical stress. The stress of the user 110 may occur whenever the user 110 suffers from mental pain or physical pain. For example, the stress of the user 110 may occur due to memory loss, intermittent memory loss, anxiety, fear, embarrassment, hesitation, and nervousness.

Also, in operation 220a, the stress index being equal to or higher than the threshold value means that the device 100 detected the stress of the user 110.

The stress index may be an indicator indicating a degree or level of the stress. For example, when the stress index is high, the degree of stress may be high or the level of stress may be high.

The stress index may be obtained by intactly using or processing a value of the bio-signal detected from the user 110. For example, the device 100 may calculate the stress index of the user 110 based on at least one of a size, an amplitude, a change rate, and a frequency of the bio-signal. A method of calculating, by the device 100, the stress index of the user 110, may be registered, edited, and deleted based on a user input.

For example, the device 100 may detect EEG of the user 110, who is a dementia patient, and analyze electricity distribution according to a frequency of the EEG to calculate the stress index of the user 110. For example, the device 100 may calculate the stress index of the user 110 based on the EEG according to Equation 1 below and determine whether the stress index is equal to or higher than the threshold value.

Beta power ratio ≥ Threshold    Equation 1

Beta power ratio [%] =

$$100 \times \frac{\text{Beta power}}{\text{Total power}} = 100 \times \frac{\int_{f \in \beta} FFT\{EEG(t)\}^2 \, df}{\int_0^\infty FFT\{EEG(t)\}^2 \, df}$$

In Equation 1, EEG(t) denotes an EEG signal detected from the user 110 according to time. FFT{EEG(t)} denotes a result value of performing a fast Fourier transform (FFT) on the EEG signal at a point of time t. Beta power denotes electricity of EEG β wave components (about 16 to 31 Hz) at the point of time t and may correspond to a value obtained by adding or integrating electricity of the EEG β wave components at the point of time t. Total power may denote total electricity of EEG at the point of time t and may correspond to a value obtained by adding or integrating electricity of EEG of all frequencies at the point of time t. Beta power ratio denotes a stress index of the user 110 at the point of time t. Also, beta power ratio may correspond to a value obtained by normalizing a value of beta power compared to total power to a value between 0% to 100%. The device 100 may determine whether beta power ratio that is the stress index of the user 110 at the point of time t is equal to or higher than a threshold value Threshold.

As another example, the device 100 may calculate the stress index of the user 110 based on the EEG detected from the user 110 according to Equation 2 and determine whether the stress index is equal to or higher than the threshold value.

Beta power *ratio(n)* ≥ Threshold    Equation 2

$$\text{Beta power } ratio(n) \, [\%] = 100 \times \frac{\text{Beta } power(n)}{\text{Total } power(n)} =$$

$$100 \times \frac{\int_{f \in \beta} STFT\{EEG(t)\}^2 \{n, f\} \, df}{\int_0^\infty STFT\{EEG(t)\}^2 \{n, f\} \, df}$$

In Equation 2, EEG(t) denotes an EEG signal detected from the user 110 according to time. STFT{EEG(t)}(n,f) denotes a result value of performing short-term Fourier transform (STFT) on the EEG signal at an $n^{th}$ time interval. Beta power(n) denotes electricity of EEG β wave components (about 16 to 31 Hz) during the $n^{th}$ time interval, and may correspond to a value obtained by adding or integrating electricity of the EEG β wave components during the $n^{th}$ time interval. Total power may denote total electricity of EEG during the $n^{th}$ time interval, and may correspond to a value obtained by adding or integrating electricity of EEG of all frequencies during the $n^{th}$ time interval. Beta power ratio(n) denotes a stress index of the user 110 during the $n^{th}$ time interval. Also, beta power ratio(n) may correspond to a value obtained by normalizing a value of beta power(n) compared to total power(n) to a value between 0 to 100. The device 100 may determine whether beta power ratio(n) that is the stress index of the user 110 during the $n^{th}$ time interval is equal to or higher than a threshold value Threshold.

As another example, the device 100 may calculate the stress index of the user 110 based on a voice signal detected from the user 110. For example, the device 100 may calculate the stress index by analyzing a size and a frequency of the voice signal of the user 110. For example, the device 100 may calculate the stress index based on a size of amplitude, a size of the frequency, a change rate of the amplitude, and a change rate of the frequency of the voice signal. Also, the device 100 may determine whether the stress index is equal to or higher than the threshold value based on the voice signal. For example, the device 100 may calculate the stress index by analyzing a frequency and amplitude of a scream of the user 110.

Also, the threshold value compared with the stress index may be flexibly set based on a state of the user 110 and a surrounding environment of the user 110.

For example, it may be highly likely that the user 110 is more stressed during a timeline from morning to daytime than during a timeline from night to dawn. In this case, the device 100 may set the threshold value applied to the timeline from morning to daytime to be lower than the threshold value applied to the timeline from night to dawn. Accordingly, the device 100 may more sensitively detect the stress of the user 110 from morning to daytime than from night to dawn.

As another example, it may be highly likely that the user may be stressed more in a kitchen or near a shoe rack than other locations. In this case, the device 100 may set the threshold value when the user 110 is in the kitchen or near the shoe rack to be lower than the threshold value when the user 110 is in another location. Accordingly, the device 100 may more sensitively detect the stress of the user 110 when the device 100 is in the kitchen or near the shoe rack. Here, a method of determining, by the device 100, an indoor location of the device 100 will be described later with reference to FIGS. 12A and 12B, 13, 14, 15A, 15B, 16, and 17.

When it is determined that the stress index of the user 110 is lower than the threshold value in operation S220a, the device 100 may continuously periodically detect the bio-signal of the user 110.

When it is determined that the stress index of the user 110 is equal to or higher than the threshold value, the device 100 may transmit the search signal 130 to the peripheral device 120 in operation 230a.

Here, the search signal 130 may be a communication signal externally transmitted from the device 100 to search for the peripheral device 120. Also, the search signal 130 may have any one of various formats according to a communication method between the device 100 and the peripheral device 120.

The device 100 may efficiently consume electricity by setting a condition under which the search signal 130 is transmitted when the stress index of the user 110 is equal to or higher than the threshold value.

Figure 2C:
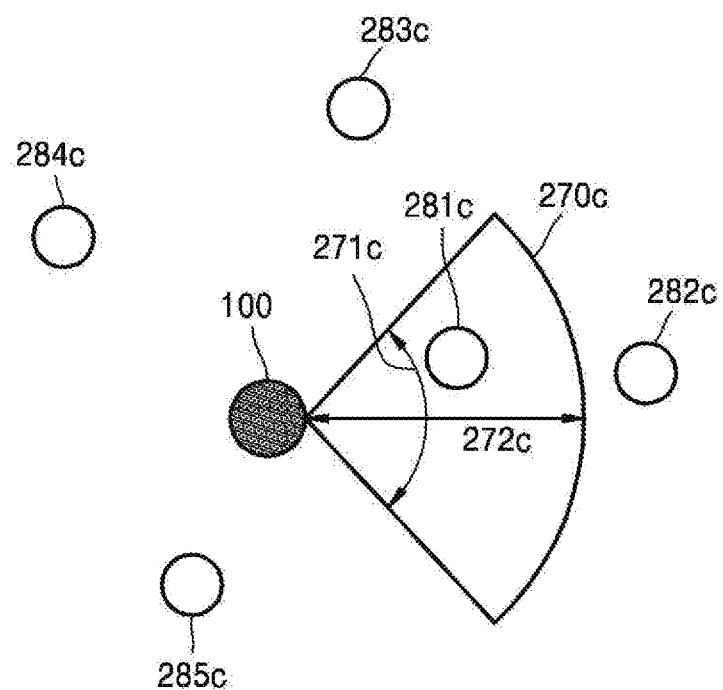
FIGS. 2C and 2D are diagrams for describing an operation of transmitting, by a device, a search signal, according to various embodiments of the present disclosure.
Figure 2D:
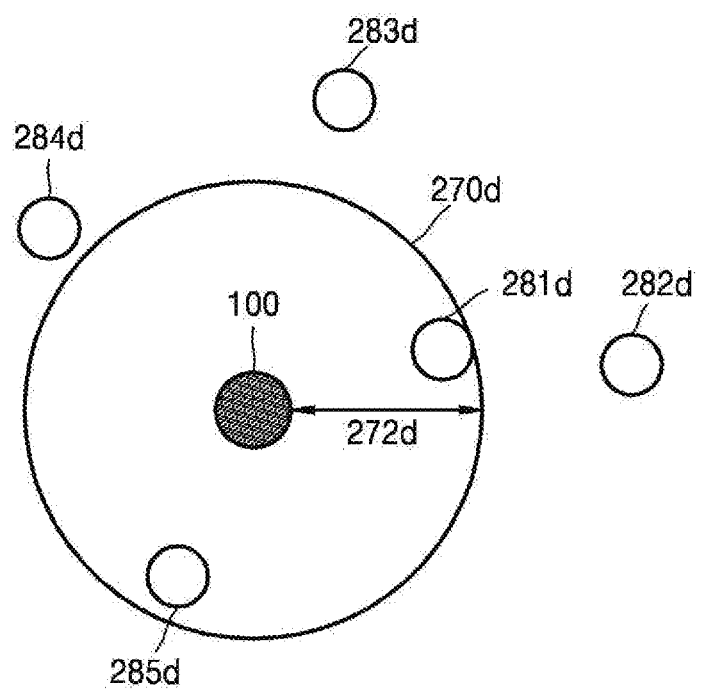

For example, the device 100 may search for the peripheral device 120 by adjusting the strength and direction of the search signal 130. FIGS. 2C and 2D are conceptual diagrams for describing search ranges 270c and 270d for the device 100 to search for a peripheral device, according to embodiments. Here, the search ranges 270c and 270d may be ranges of a search signal transmitted by the device 100.

FIG. 2C illustrates an example of the search range 270c formed when the device 100 transmits a search signal by a beamforming method according to an embodiment of the present disclosure. When the device 100 transmits the search signal by the beamforming method, the search range 270c may be formed based on a direction of the device 100. The device 100 may adjust a maximum distance 272c and an angle 271c of the search range 270c. For example, the device 100 may adjust the maximum distance 272c of the search range 270c by adjusting the transmission strength of the search signal. Also, the device 100 may adjust the angle 271c of the search range 270c from 0° to 360° by adjusting a transmission angle of the search signal. Referring to FIG. 2C, among first through fifth peripheral devices 281c through 285c, only the first peripheral device 281c is in the search range 270c, and thus only the first peripheral device 281c receives the search signal from the device 100. A method of searching for, by the device 100, at least one peripheral device based on a beamforming method will be described later with reference to FIGS. 4A, 4B, and 5.

FIG. 2D illustrates an example of the search range 270d formed when the device 100 transmits a search signal by a broadcasting method according to an embodiment of the present disclosure. Unlike the search range 270c of FIG. 2C, when the device 100 transmits the search signal via the broadcasting method, the search range 270d may be generated independently from a direction of the device 100. The device 100 may adjust a maximum distance 272d of the search range 270d. For example, the device 100 may adjust the maximum distance 272d of the search range 270d by adjusting the transmission strength of the search signal. Referring to FIG. 2D, among first through fifth peripheral devices 281 through 285d, only the first and fifth peripheral devices 281d and 285d are included in the search range 270d, and thus only the first and fifth peripheral devices 281d and 285d may receive the search signal from the device 100. A method of searching for, by the device 100, at least one peripheral device based on a broadcasting method will be described later with reference to FIGS. 6A, 6B, and 7.

Referring back to FIG. 2A, in operation 240a, the device 100 may receive the response signal 140.

The response signal 140 may be a communication signal transmitted from the peripheral device 120 to the device 100 in response to the search signal 130.

For example, referring to FIG. 2C, only the first peripheral device 281c that received the search signal from among the first through fifth peripheral devices 281c through 285c may transmit a response signal to the device 100, in response to the search signal. Also, referring to FIG. 2D, only the first and fifth peripheral devices 281d and 285d from among the first through fifth peripheral devices 281d through 285d may transmit a response signal to the device 100, in response to the search signal.

Also, the response signal 140 may include identification (ID) information of the peripheral device 120 that transmitted the response signal 140, such as a serial number, a model type, and a model name. For example, when the washing machine 121 transmits the response signal 140 to the device 100, the response signal 140 may include ID information of the washing machine 121. Accordingly, the device 100 may analyze the ID information included in the response signal 140 and identify the peripheral device 120 that transmitted the response signal 140.

Also, the response signal 140 may include state information of the peripheral device 120 that transmitted the response signal 140. For example, the state information may include at least one of state information indicating whether the peripheral device 120 is on or off, state information indicating whether a pre-set function is activated in the peripheral device 120, state information indicating an activated function in the peripheral device 120, and state information indicating whether a door or a lid of the peripheral device 120 is opened. The device 100 may analyze the state information included in the response signal 140 and determine a current state of the peripheral device 120.

In operations 230a and 240a, the device 100 may communicate with the peripheral device 120 via a wireless communication method. For example, the device 100 may transmit and receive data to and from the peripheral device 120 via a wireless communication method, such as Bluetooth (BT), Bluetooth low energy (BLE), near field communication (NFC), ZigBee, ultra-wideband (UWB), infrared communication, ultrasonic communication, and magnetic field communication.

Also, the device 100 may communicate with the peripheral device 120 through an external server. For example, the device 100 may transmit and receive data to and from the peripheral device 120 through a server, via a 3rd generation (3G) communication network, a 4th generation (4G) communication network, or WiFi.

The device 100 may search for the at least one peripheral device 120 within a pre-set distance from the device 100 based on the search signal 130 and the response signal 140.

In operation 250a, the device 100 may select a peripheral device that stressed the user 110 from among the at least one peripheral device 120 based on the at least one response signal received in operation 240a. Hereinafter, a peripheral device selected by the device 100 from among the at least one peripheral device 120 will be referred to as a 'first device'.

The device 100 may select a peripheral device nearest to the user 110 as the first device, from among the at least one peripheral device 120. Generally, it is most likely that the peripheral device nearest to the user 110 from among the at least one peripheral device 120 may stress the user 110.

For example, the device 100 may select the peripheral device nearest to the user 110 as the first device based on signal strength of the at least one response signal 140. For example, the device 100 may select the peripheral device 120 that transmitted the response signal 140 having highest signal strength as the first device.

As another example, the device 100 may select the peripheral device nearest to the user 110 as the first device based on receiving sensitivity of the at least one response signal 140. For example, the device 100 may select the peripheral device 120 that transmitted the response signal 140 having highest receiving sensitivity from among the at least one response signal 140 received from the at least one peripheral device 120, as the first device.

The device 100 may select the first device from among the at least one peripheral device 120 based on a history of selecting the first device by the device 100. The history of selecting the first device may include information in which a number of times the peripheral device 120 is selected as the first device or a probability of the peripheral device 120 being selected as the first device is accumulated according to the peripheral devices 120. Also, the history of selecting the first device may include time information and location information when and where the stress index of the user 110 exceeds the threshold value, and a maximum value of the stress index of the user 110.

TABLE 1

History of Selecting First Device

| | Selected First Device | Maximum Value of Stress Index | Time | Location |
|---|---|---|---|---|
| 1 | Washing Machine | S1 | 12:00 | Laundry Room |
| 2 | Refrigerator | S2 | 09:00 | Kitchen |
| 3 | Washing Machine | S3 | 12:30 | Laundry Room |
| 4 | Washing Machine | S4 | 13:30 | Laundry Room |
| 5 | TV | S5 | 19:00 | Living Room |
| 6 | ... | ... | ... | ... |

Table 1 shows an example of the history of selecting the first device. For example, referring to Table 1, the device 100 selected the washing machine 121 as the first device three times and the refrigerator as the first device one time, and thus it may be highly likely that the washing machine 121 is selected as the first device compared to the refrigerator.

In this case, even if signal strength of a response signal of the washing machine 121 is the same as signal strength of a response signal of the refrigerator, the device 100 may select the washing machine 121 as the first device based on the history of selecting the first device.

As another example, according to Table 1, it is highly likely that the washing machine 121 is selected as the first device compared to the TV and the refrigerator at a time between 12:00 to 14:00. When the stress index of the user 110 exceeds the threshold value at the time between 12:00 to 14:00, the device 100 may select the washing machine 121 as the first device according to the history of selecting the first device, even when the signal strength of the response signal of the washing machine 121 is the same as the signal strength of the response signal of the refrigerator As another example, according to Table 1, when the device 100 is in the laundry room, it is highly likely that the washing machine 121 is selected as the first device compared to the TV and the refrigerator. When the device 100 is in the laundry room and the stress index of the user 110 exceeds the threshold value, the device 100 may select the washing machine 121 as the first device according to the history of selecting the first device, even when the signal strength of the response signal of the washing machine is the same as the signal strength of the response signal of the refrigerator.

In operation 260a, the device 100 may output information of the selected peripheral device, i.e., information of the first device.

The information of the first device that stressed the user 110 may include guide information corresponding to execution of a function of the first device, state information of the first device, and information for describing characteristics of the first device.

For example, the guide information corresponding to the execution of the function of the first device may include guide information for manipulating a graphical user interface (GUI) of the first device and guide information for manipulating a switch or button of the first device, in order to execute a certain function of the first device.

The state information of the first device may be state information of the first device at a point of time when the user 110 is stressed. Also, the device 100 may receive the state information included in the response signal of the first device and output the state information of the first device. For example, the state information of the first device may include at least one of state information indicating whether the first device is on or off, state information indicating whether a pre-set function is activated in the first device, state information indicating an activated function in the first device, and state information indicating whether a door or a lid of the first device is opened.

For example, the information for describing the characteristics of the first device may include a name of the first device, a main function of the first device, directions for using the first device, and an error recovery method.

The device 100 may pre-store the information of the first device in order to output the information of the first device. Also, the device 100 may register, edit, and delete the information of the first device based on a user input.

Alternatively, the device 100 may request the first device for the information of the first device in order to output the information of the first device. For example, the device 100 may be paired with the first device, request the first device for the information of the first device, receive the information of the first device from the first device, and output the information of the first device.

The device 100 may output the information of the first device in at least one form from visual information, auditory information, and a vibration signal, but a form of the information of the first device is not limited thereto.

For example, the device 100 may output the information of the first device as visual information by using a displayer or a projector included in the device 100. For example, the device 100 may display, on the displayer, the information of the first device including at least one of a character, a number, a sign, a still image, and a moving image. Also, when the device 100 includes the projector, the device 100 may externally project the information of the first device including at least one of a character, a number, a sign, a still image, and a moving image.

As another example, the device 100 may output the information of the first device via a voice or sound through a sound outputter.

As another example, the device 100 may output the information of the first device as a vibration signal through a vibration motor. For example, the device 100 may output a warning signal described later with reference to FIGS. 20 through 22 in a vibration signal. A method of outputting, by the device 100, the information of the first device may vary depending on a type of the device 100. For example, when the device 100 is worn on an ear, like a hearing aid or an earphone, the device 100 may output the information of the first device in at least one of voice and sound.

The device 100 may output different types of the information of the first device according to a state of the first device. For example, the device 100 may analyze the state information included in the response signal of the first device and determine the state of the first device. The device 100 selects the information of the first device to be output according to the state of the first device and output the selected information of the first device. For example, when the first device is turned off according to the state information of the first device, the device 100 may output information about how to turn on the first device. Also, when the first device is turned on according to the state information of the first device, the device 100 may output information about how to turn off the first device or how to activate a certain function of the first device.

FIG. 2B is a flowchart of a method 200b of searching for, by the device 100, the peripheral device 120 based on the search signal 130 and the response signal 140, and outputting information of the peripheral device 120, according to an embodiment of the present disclosure.

In operation 220b, the device 100 may receive stress information of the user 110 from the at least one peripheral device 120.

The stress information may be information used to determine whether the user 110 is stressed. The stress information may include an image of the user 110, which is captured by the peripheral device 120. Also, the stress information may include a voice signal of the user 110, recognized by the peripheral device 120. Also, the stress information may include an input signal received by the peripheral device 120.

When the stress information includes the image of the user 110, the device 100 may analyze the image and calculate a stress index of the user 110. Here, image of the user 110 may be a still image or a moving image. For example, the peripheral device 120 may capture the image of the user 110 by using a built-in camera and transmit the image of the user 110 to the device 100. The device 100 may recognize a pre-set expression, such as a surprised look or a puzzled expression, based on the image of the user 110, and calculate the stress index of the user 110. As another example, the device 100 may recognize a pre-set action or movement, such as a trembling hand, a stiff body (for example, if the user 110 does not move for a certain time period), or an abnormal movement, based on the image of the user 110, and calculate the stress index of the user 110. Also, the device 100 may determine whether the stress index is equal to or higher than a threshold value.

When the stress information includes the voice signal of the user 110, the device 100 may analyze the voice signal and calculate the stress index of the user 110. For example, the peripheral device 120 may recognize the voice signal of the user 110 by using a built-in microphone and transmit the voice signal to the device 100. The device 100 may analyze a size and frequency of the voice signal and determine the stress index of the user 110. For example, the device 100 may calculate the stress index based on a size of amplitude, a size of a frequency, a change rate of the amplitude, and a change rate of the frequency of the voice signal. Also, the device 100 may determine whether the stress index is equal to or higher than the threshold value.

When the stress information includes the input signal received by the peripheral device 120, the device 100 may analyze the input signal and calculate the stress index. For example, the device 100 may analyze an amount of the input signal received by the peripheral device 120 for a certain time period and calculate the stress index. For example, the stress index may be proportional to the amount of the input signal received by the peripheral device 120 for the certain time period. As another example, the device 100 may analyze a pattern of the input signal and calculate the stress index. For example, the stress index may be proportional to a number of times the user 110 repeatedly pressed a button or switch of the peripheral device 120. Alternatively, the stress index may be proportional to a number of buttons or switches of the peripheral device 120 the user pressed together.

Upon receiving the stress information in operation 220b, the device 100 may transmit the search signal 130 to the at least one peripheral device 120 in operation 230b.

In operation 240b, the device 100 may receive the at least one response signal 140 from the at least one peripheral device 120 that received the search signal 130 transmitted in operation 230b.

In operation 250b, the device 100 may select the first device from among the at least one peripheral device 120 based on the at least one response signal 140 received in operation 240b.

The first device may be the peripheral device 120 that transmitted the stress information of the user 110. For example, the user 110, who is a dementia patient, wants to use the washing machine 121, but may not remember how to use the washing machine 121 due to memory loss. Then, the washing machine 121 may capture an image of the user 110 by using a built-in camera and transmit the image to the device 100. The device 100 may determine that the user 110 is stressed based on the image of the user 110 received from the washing machine 121. Also, the device 100 may transmit the search signal 130 to the at least one peripheral device 120. Also, the device 100 may select the washing machine 121 as the first device based on the at least one response signal 140.

The first device may be different from the peripheral device 120 that transmitted the stress information of the user 110. For example, the user 110, who is a dementia patient, wants to use the washing machine 121, but may not remember how to use the washing machine 121 due to memory loss. Then, the refrigerator may capture an image of the user 110 by using a built-in camera and transmit the image to the device 100. The device 100 may determine that the user 110 is stressed from the image of the user 110 received from the refrigerator. Also, the device 100 may transmit the search signal 130 to the at least one peripheral device 120. Also, the device 100 may select the washing machine 121 as the first device based on the at least one response signal 140.

Meanwhile, when the stress information includes the input signal received by the peripheral device 120, the device 100 may select a peripheral device that received an abnormal input signal as the first device, and thus operations 230b through 250b may be omitted. For example, the washing machine 121 may receive an abnormal input signal from the user 110, and the device 100 may receive the stress information from the washing machine 121. Accordingly, the device 100 may select the washing machine 121 that received the abnormal input signal as the first device, without having to transmit a search signal.

In operation 260b, the device 100 may output information of the first device.

As described above with reference to FIG. 2B, a method of determining, by the device 100, whether the user 110 is stressed may include a method of receiving stress information from the peripheral device 120.

Figure 3:
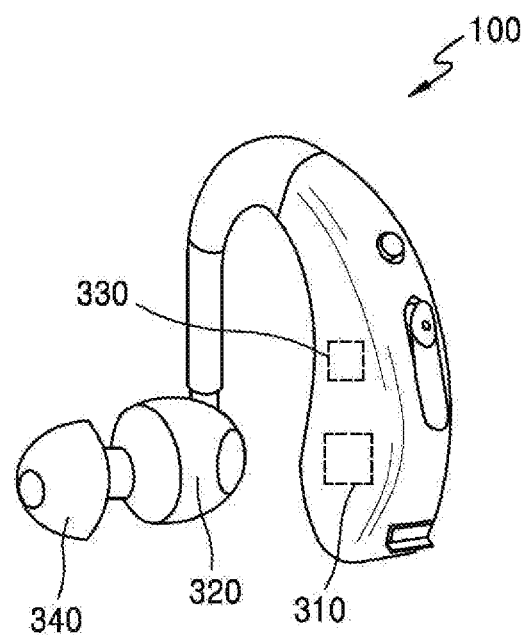
FIG. 3 illustrates a device in an ear-hook type, according to an embodiment of the present disclosure.

FIG. 3 illustrates a device 100 in an ear-hook type, according to an embodiment of the present disclosure.

The device 100 may be a wearable device worn on an ear. For example, the device 100 may be an ear-hook type that is hooked behind an ear, an ear canal type that is inserted into an entrance of an ear canal, an eardrum type that is completely inserted into an ear canal, and a concha type that is worn on a concha of auricle.

The device 100 according to an embodiment may include a sensor 320 for detecting a bio-signal of a user at an inner ear or an external ear of the user.

Also, the device 100 that is worn on the ear may include a sensor 310 for detecting a bio-signal of the user at a body part near the ear, such as a temple, a mastoid, and the carotid behind the ear.

Also, the device 100 that is worn on the ear may include a communicator 330 for communication with an external device, and an outputter 340 that outputs information of the first device as a voice.

Since most dementia patients are elderly people, their physical abilities, such as sensory nerves and motor nerves, may be relatively low compared to other patients who do not suffer from dementia. Thus, the device 100 that is worn on the ear may provide functions that are helpful to the physical abilities of dementia patients.

For example, the device 100 that is worn on the ear may have a hearing aid function for the user 110 who has hearing impairment. For example, the device 100 may amplify the volume of sound according to frequencies.

Also, the device 100 that is worn on the ear may output the information of the first device as a voice.

The dementia patients may have eye movement abnormalities. For example, the dementia patients may be unable to look at an object accurately. Alternatively, since most dementia patients are elderly people, they may have presbyopia. Even when the user 110 with presbyopia looks at an object, an image of the object may not fall on the retina. In this case, the device 100 may more efficiently provide the information of the first device to the user 110 by using an auditory signal than a visual signal.

Figure 4A:
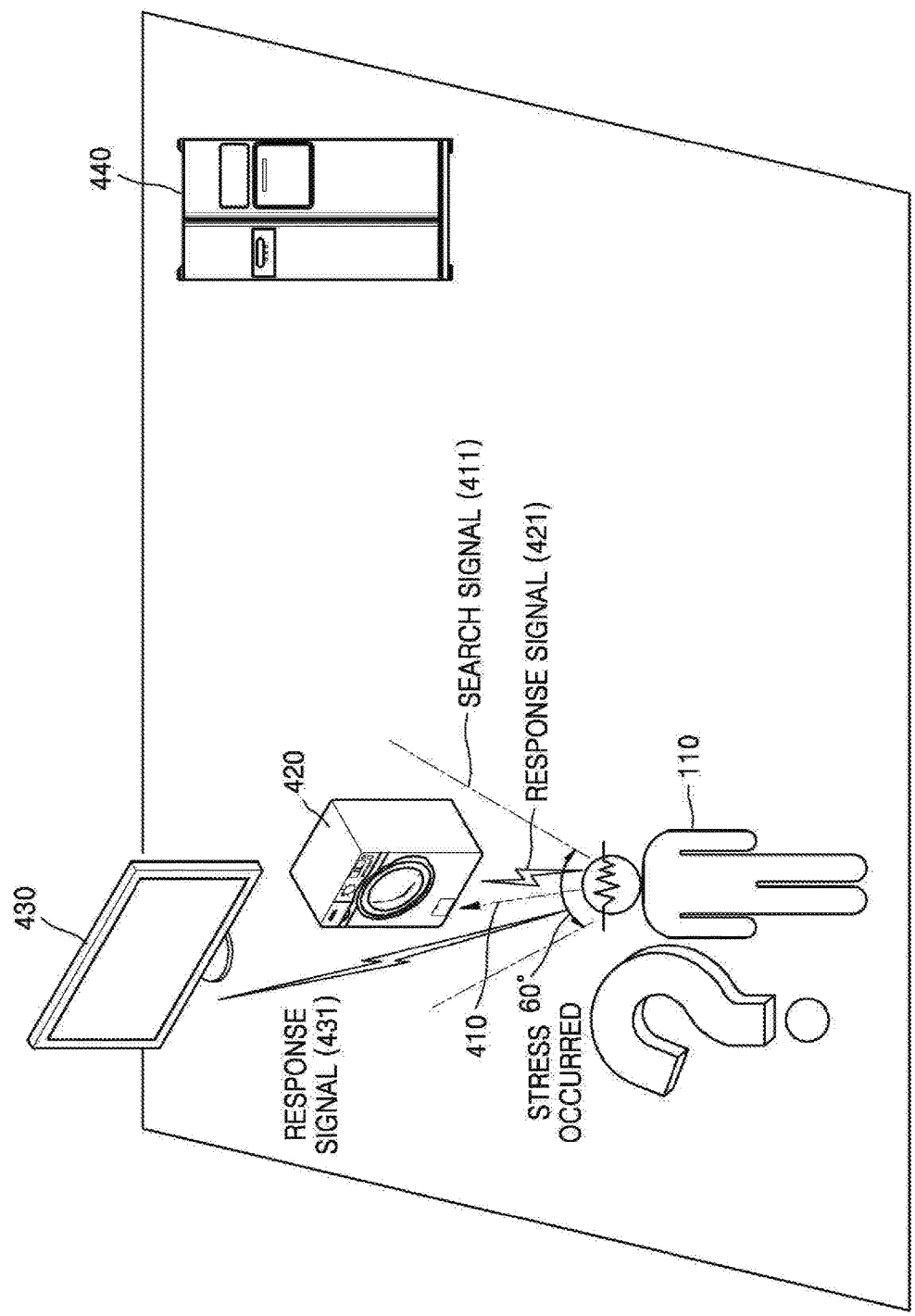
FIGS. 4A and 4B are diagrams for describing an operation of searching for, by a device, peripheral devices based on a beamforming method, according to various embodiments of the present disclosure.
Figure 4B:
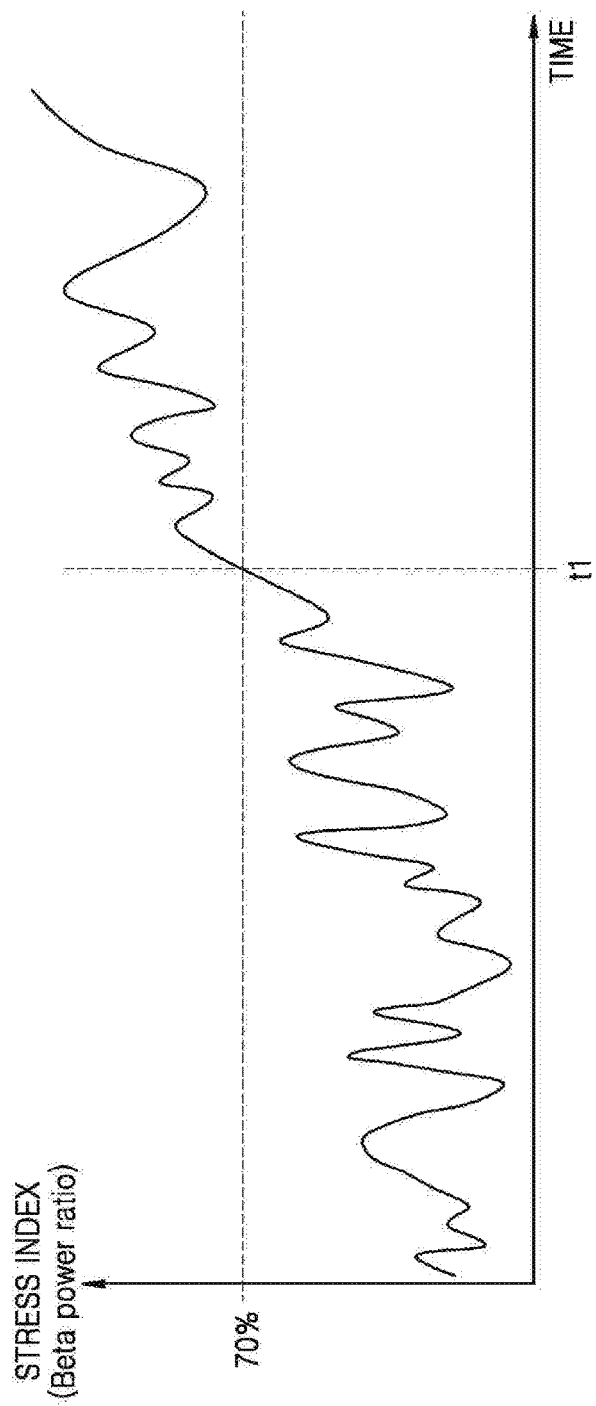

FIGS. 4A and 4B are diagrams for describing an operation of searching for, by the device 100, peripheral devices, i.e., a washing machine 420 and a TV 430, based on a beamforming method, according to various embodiments of the present disclosure.

The device 100 may search for peripheral devices, i.e., the washing machine 420, the TV 430, and a refrigerator 440, which are located within a pre-set distance from the device 100 and within a certain range from a pre-set direction 410 of the device 100.

FIG. 4B shows a graph of a stress index according to time. When the user 110 is not stressed, the stress index of the user 110, calculated by the device 100, may be lower than the threshold value. However, when the user 110 is stressed, the stress index of the user 110, calculated by the device 100, may be equal to or higher than the threshold value. For example, at a point of time t1, the user 110, who is a dementia patient, may not remember how to manipulate the washing machine 420 due to intermittent memory loss and suffer from mental stress. Also, at the point of time t1, the stress index of the user 110 may exceed the threshold value. For example, as described above with reference to FIG. 2A, the stress index may be a beta power ratio calculated based on EEG measured from the user 110. The beta power ratio may have a value between 0% to 100%. Also, a threshold value of the beta power ratio may be set to be 70% by the user 110 and may vary based on location information of the user 110 or current time information.

When the stress index of the user 110 is equal to or higher than the threshold value, the device 100 may receive, from the user 110, a user input requesting the device 100 to search for the peripheral devices, i.e., the washing machine 420 and the TV 430. For example, when the stress index of the user 110 is equal to or higher than the threshold value, the device 100 may output a voice signal of "Do you need help?" to request the user 110 for a user input. After requesting for the user input, the device 100 may recognize the voice of the user 110, such as "Yes" or "Device information request", to receive the user input. As another example, when the stress index of the user 110 is equal to or higher than the threshold value, the device 100 may output a vibration signal to request the user 110 for a user input. After requesting for the user input, the device 100 may receive the user input requesting the device 100 to search for the washing machine 420 and the TV 430 based on at least one of voice recognition, button manipulation, and a user interface (UI) screen. If the user 110 does not want help from the device 100 despite that the stress index is equal to or higher than the threshold value, the user 110 may end an operation of the device 100 based on at least one of voice recognition, button manipulation, and a UI screen.

Referring to FIG. 4A, the device 100 may transmit a search signal 411 in a beamforming method in order to search for the washing machine 420 and the TV 430 that stressed the user 110. For example, upon receiving a user input of requesting the device 100 to search for the washing machine 420 and the TV 430, the device 100 may transmit the search signal 411 within a left and right range of 30° based on the pre-set direction 410 of the device 100. The pre-set direction 410 may vary depending on a type of the device 100. For example, when the device 100 is worn on an ear, the pre-set direction 410 may be a direction perpendicular to a face of the user 110. As another example, when the device 100 is a glasses type, the pre-set direction 410 may be perpendicular to lenses.

The washing machine 420 and the TV 430, which are located with the pre-set distance and within the left and right range of 30° based on the pre-set direction 410, may receive the search signal 411 from the device 100. However, since the refrigerator 440 is not located with the left and right range of 30° based on the pre-set direction 410, the refrigerator 440 does not receive the search signal 411. The washing machine 420 and the TV 430 that received the search signal 411 may respectively transmit response signals 421 and 431 to the device 100.

The device 100 may select any one of the washing machine 420 and the TV 430 as the first device based on the response signal 421 and 431. For example, the device 100 may select the washing machine 420 that transmitted the response signal 421 having strongest signal strength among the response signals 421 and 431 as the first device.

FIG. 4B shows signal strength of response signals of peripheral devices, i.e., the washing machine 420, the TV 430, and the refrigerator 440, which is measured by the device 100. For example, the signal strength of the response signal 421 of the washing machine 420 may be 10 dBm, and the signal strength of the response signal 431 of the TV 430 may be 4 dBm. Since the refrigerator 440 does not receive the search signal 411, the refrigerator 440 does not transmit a response signal to the device 100. When the device 100 transmits the search signal 411 by the beamforming method, the washing machine 420 that transmitted the response signal 421 having the strongest signal strength may be located close to the device 100 based on the pre-set direction 410 of the device 100, and thus the device 100 may select the washing machine 420 as the first device. Also, the device 100 may output a control method of the washing machine 420 to help the user 110, who does not remember how to control the washing machine 420.

Figure 5:
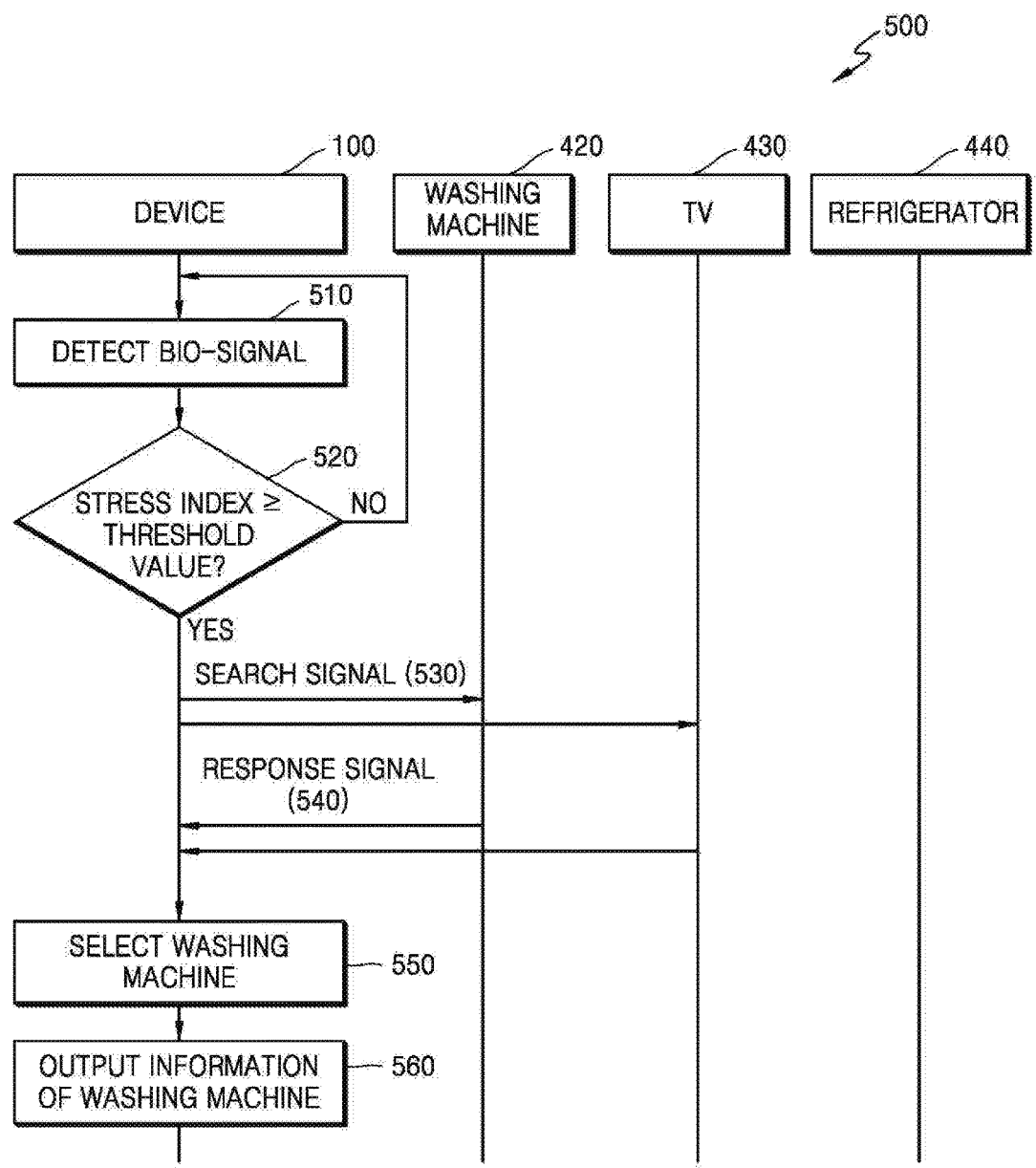
FIG. 5 is a flowchart of a method of searching for, by a device, a peripheral device based on a beamforming method, according to an embodiment of the present disclosure.

FIG. 5 is a flowchart of a method 500 of searching for, by the device 100, a peripheral device based on a beamforming method, according to an embodiment of the present disclosure.

In operation 510, the device 100 may detect a bio-signal of the user 110.

In operation 520, the device 100 may calculate a stress index of the user 110 based on the bio-signal and determine whether the stress index is equal to or higher than a threshold value.

When it is determined that the stress index is equal to or higher than the threshold value, the device 100 may transmit a search signal in a pre-set direction based on the device 100, in operation 530.

In order to transmit the search signal in the pre-set direction, the device 100 may use a radio frequency (RF) signal based on a directional antenna, or may use a communication signal having a linear characteristic, such as infrared ray or ultrasonic wave.

The device 100 may transmit the search signal within a pre-set rage based on the pre-set direction. For example, the device 100 may transmit the search signal within a left and right range of 10° or 30° based on a front surface of the device 100. As another example, the device 100 may transmit the search signal within a left and right range of 10° or 30° based on a front of the user 110 when the device 100 is worn on the user 110.

For example, the device 100 may transmit the search signal to the washing machine 420 and the TV 430 located within the pre-set distance from the device 100 and within the pre-set direction based on the device 100.

Also, the device 100 may adjust a search range by adjusting signal strength of the search signal.

In operation 540, the device 100 may receive response signals from the washing machine 420 and the TV 430 that received the search signal. Unlike operation 730 of FIG. 7 that is described later, the refrigerator 440 does not receive the search signal in operation 530 of FIG. 5, and thus does not transmit a response signal to the device 100.

Here, a response signal may include ID information of a peripheral device that transmitted the response signal. For example, the response signal 421 of FIG. 4A may include ID information of the washing machine 420, and the response signal 431 of FIG. 4A may include ID information of the TV 430.

In operation 550, the device 100 may select the first device based on the response signals. For example, the device 100 may select the washing machine 420 that transmitted the response signal having highest signal strength as the first device.

In operation 560, the device 100 may output information of the washing machine 420 (i.e., information of the first device). For example, the device 100 may output information about a control method for executing a rinsing function, a detergent putting function, a spin-drying function, and a drying function of the washing machine 420. In detail, the device 100 may output, as a voice, the information about the control method, such as "Please put laundry in and press start button".

The device 100 may output different types of information of the washing machine 420 according to state information of the washing machine 420. For example, the device 100 may output different types of information based on whether the washing machine 420 is being operated. In detail, when it is determined that the washing machine 420 is currently performing a washing function based on the state information included in the response signal of the washing machine 420, the device 100 may output the state information and directions for the use as a voice, such as "Washing Please don't turn off power". As another example, when the washing is finished and laundry is left in the washing machine 420, the device 100 may output the state information and the use as a voice, such as "Washing is finished. Please open lid and take out laundry". As another example, when washing is not started but the washing machine 420 is filled with laundry, the device 100 may output the state information and the use as a voice, such as "Full with laundry. Please press start button". As another example, when washing is finished and the washing machine 420 is empty, the device 100 may output the state information and the use as a voice, such as "Please put laundry in and press start button".

In FIGS. 4A, 4B, and 5, the device 100 selects the washing machine 420 as the first device and outputs the information of the washing machine 420, but an embodiment is not limited thereto. For example, the device 100 may select, as the first device, the TV 430, the refrigerator 440, or another device from among peripheral devices.

For example, the TV 430 may be selected as the first device. The device 100 may output different types of information of the TV 430 based on state information included in the response signal 431 of the TV 430. For example, when it is determined that the TV 430 is turned off according to the state information included in the response signal 431, the device 100 may output information about how to turn on the TV 430. As another example, when it is determined that the TV 430 is turned on according to the state information included in the response signal 431, the device 100 may output information about how to turn off the TV 430, how to change a channel of the TV 430, or how to set an external input.

The device 100 may receive the information of the TV 430 (i.e., information of the first device) from the TV 430. For example, the device 100 may request the TV 430 for frequently viewed channel information, receive the frequently viewed channel information from the TV 430, and output the frequently viewed channel information as the information of the first device.

As another example, the refrigerator 440 may be the first device. The device 100 may output different types of information of the refrigerator 440 according to state information included in a response signal of the refrigerator 440. For example, when it is determined that the refrigerator 440 is opened according to the state information, the device 100 may output information about how to open the refrigerator 440. As another example, when it is determined that the refrigerator 440 is opened according to the state information, the device 100 may output information about a frequently found food. Here, the information about the frequently found food may be pre-set in the device 100.

As another example, an air conditioner (not shown) may be the first device. The device 100 may output different types of information of the air conditioner according to state information included in a response signal of the air conditioner. For example, when it is determined that the air conditioner is turned off according to the state information, the device 100 may output information about how to turn on the air conditioner. As another example, when it is determined that the air conditioner is turned on according to the state information, the device 100 may output information about how to set a temperature.

As another example, an electric rice cooker (not shown) may be the first device. The device 100 may output different types of information of the electric rice cooker according to state information included in a response signal of the electric rice cooker. For example, when it is determined that there is no rice in the electric rice cooker according to the state information, the device 100 may output information about cooking. As another example, when it is determined that there is rice in the electric cooker and a lid of the electric rice cooker is closed according to the state information, the device 100 may output information about how to open the lid of the electric rice cooker.

As another example, when a smart phone (not shown) is the first device, the device 100 may output information about how to make a call by using the smart phone.

In addition, when the device 100 selects a computer, a camera, or an MP3 as the first device by detecting stress of the user 110, the device 100 may output information about how to turn on or off the computer, the camera, or the MP3.

Figure 6A:
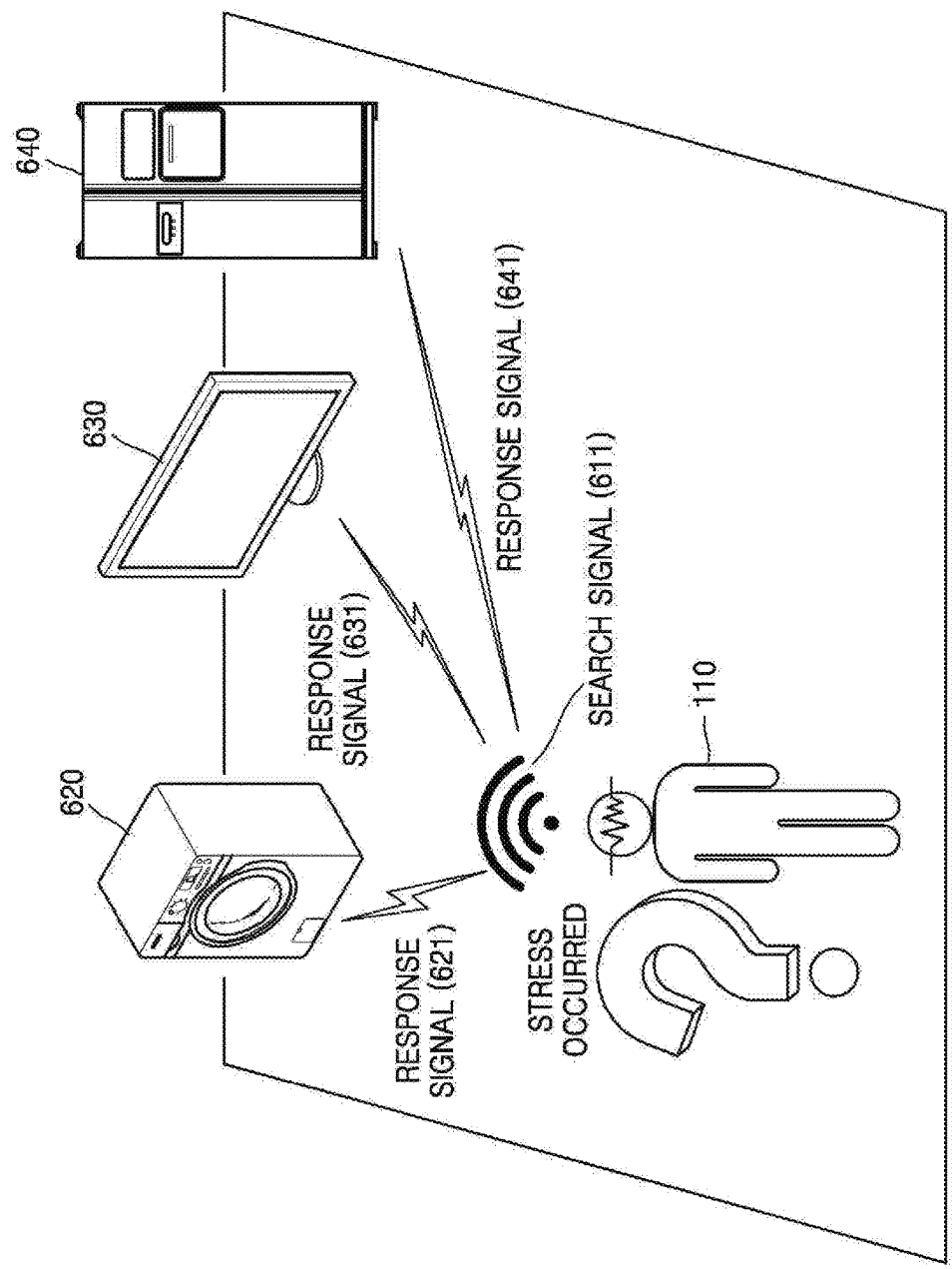

FIGS. 6A and 6B are diagrams for describing an operation of searching for, by the device 100, peripheral devices, i.e., a washing machine 620, a TV 630, and a refrigerator 640, based on a broadcasting method, according to various embodiments of the present disclosure.

The device 100 may search for the washing machine 620, the TV 630, and the refrigerator 640 that are located within a pre-set distance from the device 100 regardless of a direction of the device 100, by communicating with the washing machine 620, the TV 630, and the refrigerator 640.

FIG. 6B shows a graph of a stress index according to time. When the user 110 is not stressed, the stress index of the user 110, calculated by the device 100, may be lower than a threshold value. However, when the user 110 is stressed, the stress index of the user 110, calculated by the device 100, may be equal to or higher than the threshold value. For example, at a point of time t1, the user 110, who is a dementia patient, may not remember how to manipulate the washing machine 620 due to intermittent memory loss and suffer from mental stress. Also, at the point of time t1, the stress index of the user 110 may exceed the threshold value. For example, as described above with reference to FIG. 2A, the stress index may be a beta power ratio calculated based on EEG measured from the user 110. The beta power ratio may have a value between 0% to 100%. Also, a threshold value of the beta power ratio may be set to be 70% by the user 110 and may vary based on location information of the user 110 or current time information.

When the stress index of the user 110 is equal to or higher than the threshold value, the device 100 may receive, from the user 110, a user input requesting the device 100 to search for the peripheral devices, i.e., the washing machine 620, the TV 630, and the refrigerator 640. For example, when the stress index of the user 110 is equal to or higher than the threshold value, the device 100 may output a voice signal of "Do you need help?" to request the user 110 for a user input. After requesting for the user input, the device 100 may recognize the voice of the user 110, such as "Yes" or "Device information request", to receive the user input. As another example, when the stress index of the user 110 is equal to or higher than the threshold value, the device 100 may output a vibration signal to request the user 110 for a user input. After requesting for the user input, the device 100 may receive the user input requesting the device 100 to search for the washing machine 620, the TV 630, and the refrigerator 640 based on at least one of voice recognition, button manipulation, and a UI screen. If the user 110 does not want help from the device 100 despite that the stress index is equal to or higher than the threshold value, the user 110 may end an operation of the device 100 based on at least one of voice recognition, button manipulation, and a UI screen.

Referring to FIG. 6A, the device 100 may transmit a search signal 611 by the broadcasting method in order to search for a peripheral device that stressed the user 110. For example, upon receiving a user input requesting the device 100 to search for the washing machine 620, the TV 630, and the refrigerator 640, the device 100 may transmit the search signal 611 by using a non-directional antenna and search for the washing machine 620, the TV 630, and the refrigerator 640 within the pre-set distance from the device 100 regardless of the direction of the device 100.

The washing machine 620, the TV 630, and the refrigerator 640 located at the pre-set distance from the device 100 may receive the search signal 611. Then, the washing machine 620, the TV 630, and the refrigerator 640 may respectively transmit response signals 621, 631, and 641 to the device 100.

The device 100 may select one of the washing machine 620, the TV 630, and the refrigerator 640 as the first device based on the response signals 621, 631, and 641. For example, the device 100 may select the washing machine 620 that transmitted the response signal 621 having strongest signal strength among the response signals 621, 631, and 641, as the first device.

FIG. 6B shows signal strength of response signals 621, 631, and 641 of the washing machine 620, the TV 630, and the refrigerator 640, which is measured by the device 100. For example, the signal strength of the response signal 621 of the washing machine 620 may be 8 dBm, and the signal strength of the response signal 631 of the TV 630 may be 4 dBm, and the signal strength of the response signal 641 of the refrigerator 640 may be 2 dBm. When the device 100 transmits the search signal 611 by the beamforming method, the washing machine 620 that transmitted the response signal 621 having the strongest signal strength may be located close to the device 100, and thus the device 100 may select the washing machine 420 as the first device. Also, the device 100 may output a control method of the washing machine 620 to help the user 110, who does not remember how to control the washing machine 620.

Figure 7:
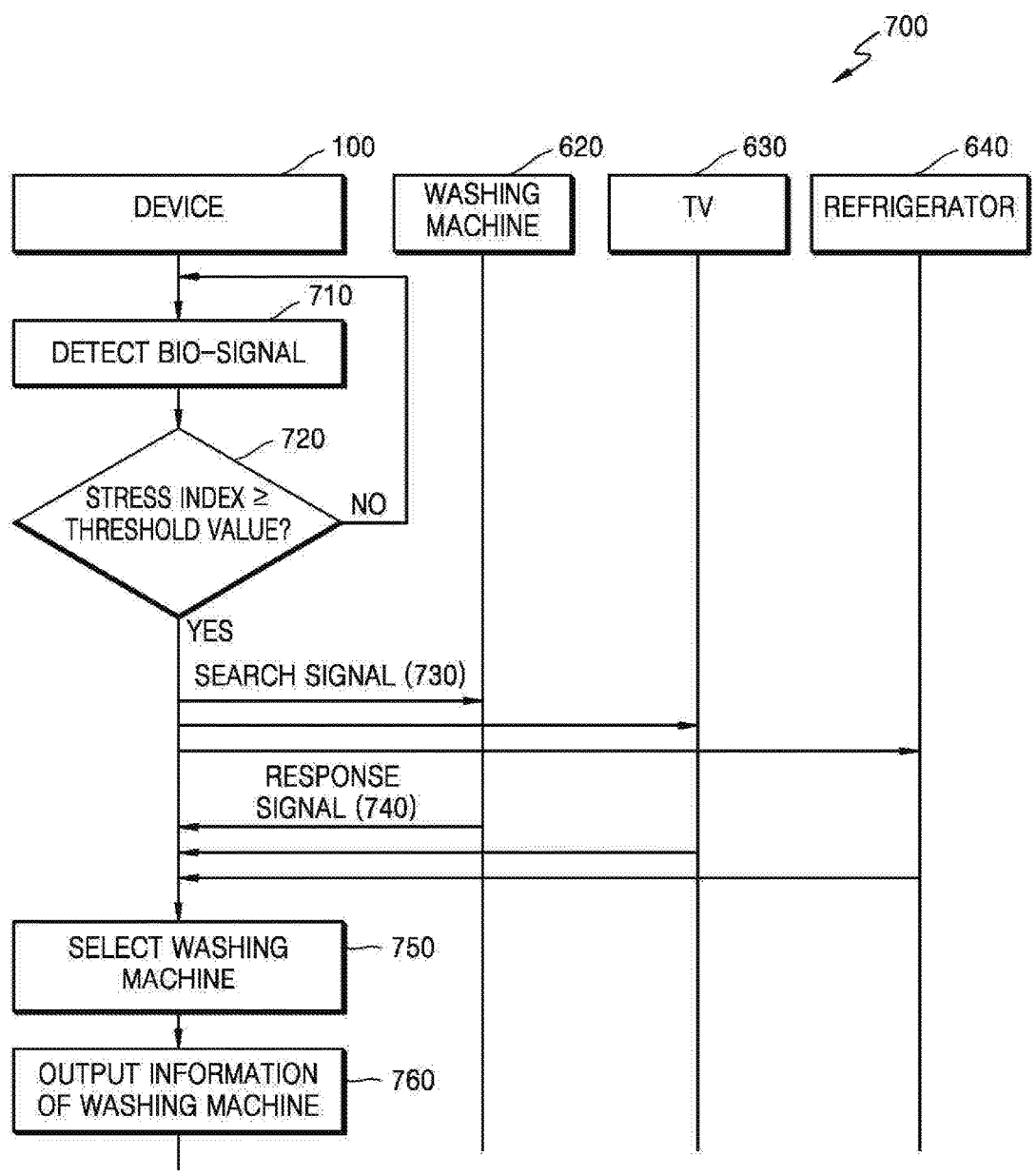
FIG. 7 is a flowchart of a method of searching for, by a device, peripheral devices based on a broadcasting method, according to an embodiment of the present disclosure.

FIG. 7 is a flowchart of a method 700 of searching for, by the device 100, peripheral devices, i.e., the washing machine 620, the TV 630, and the refrigerator 640, based on a broadcasting method, according to an embodiment of the present disclosure.

In operation 710, the device 100 may detect a bio-signal of the user 110.

In operation 720, the device 100 may calculate a stress index of the user 110 based on the bio-signal of the user 110 and determine whether the stress index is equal to or higher than a threshold value.

When it is determined that the stress index is equal to or higher than the threshold value, the device 100 may transmit the search signal 611 via the broadcasting method, in operation 730. For example, the device 100 may transmit the search signal 611 to at least one peripheral device, i.e., the washing machine 620, the TV 630, and the refrigerator 640, which is located within a pre-set distance from the device 100 regardless of a direction of the device 100. Also, the device 100 may adjust signal strength of the search signal 611 to adjust a search range.

In operation 740, the device 100 may receive the response signals 621, 631, and 641 respectively from the washing machine 620, the TV 630, and the refrigerator 640 that received the search signal 611.

A response signal may include ID information of a peripheral device that transmitted the response signal. For example, the response signal 621 may include ID information of the washing machine 620, the response signal 631 may include ID information of the TV 630, and the response signal 641 may include ID information of the refrigerator 640.

Also, the response signals 621 through 641 may include images of the user 110. The device 100 may analyze the images of the user 110 included in the response signals 621 through 641 to determine an eye direction of the user 110.

Upon receiving the search signal 611, the washing machine 620, the TV 630, and the refrigerator 640 may capture an image of a face of the user 110 and transmit the response signals 621 through 641 including the images to the device 100. The device 100 analyzes the received images to determine which one of the washing machine 620, the TV 630, and the refrigerator 640 transmitted the response signals 6210 through 641 the eyes of the user 110 are looking at.

For example, when the stress index of the user 110 exceeds the threshold value and the device 100 transmits the search signal 611 to the washing machine 620, the TV 630, and the refrigerator 640, the user 110 may be looking at the washing machine 620. Then, the washing machine 620, the TV 630, and the refrigerator 640 capture the images of the user 110 by using a camera at a point of time when the search signal 611 is received and transmit the images to the device 100. The device 100 may analyze the image included in the response signal 621 of the washing machine 620 and determine that the eyes of the user 110 are on the washing machine 620. Meanwhile, the device 100 may analyze the images included in the response signals 631 and 641 of the TV 630 and the refrigerator 640 and determine that the eyes of the user 110 are not on the TV 630 and the refrigerator 640.

In operation 750, the device 100 may select the first device based on the response signals 621 through 641. For example, the device 100 may analyze the ID information included in the response signal 621 having the strongest signal strength and select the washing machine 620 as the first device.

The device 100 may select the first device based on eye information of the user 110. For example, the device 100 may analyze the images of the user 110, which are included in the response signals 621 through 641, determine that the eyes of the user 110 are on the washing machine 620, and select the washing machine 620 as the first device.

In operation 760, the device 100 may output information of the washing machine 620, i.e., information of the first device.

Figure 8:
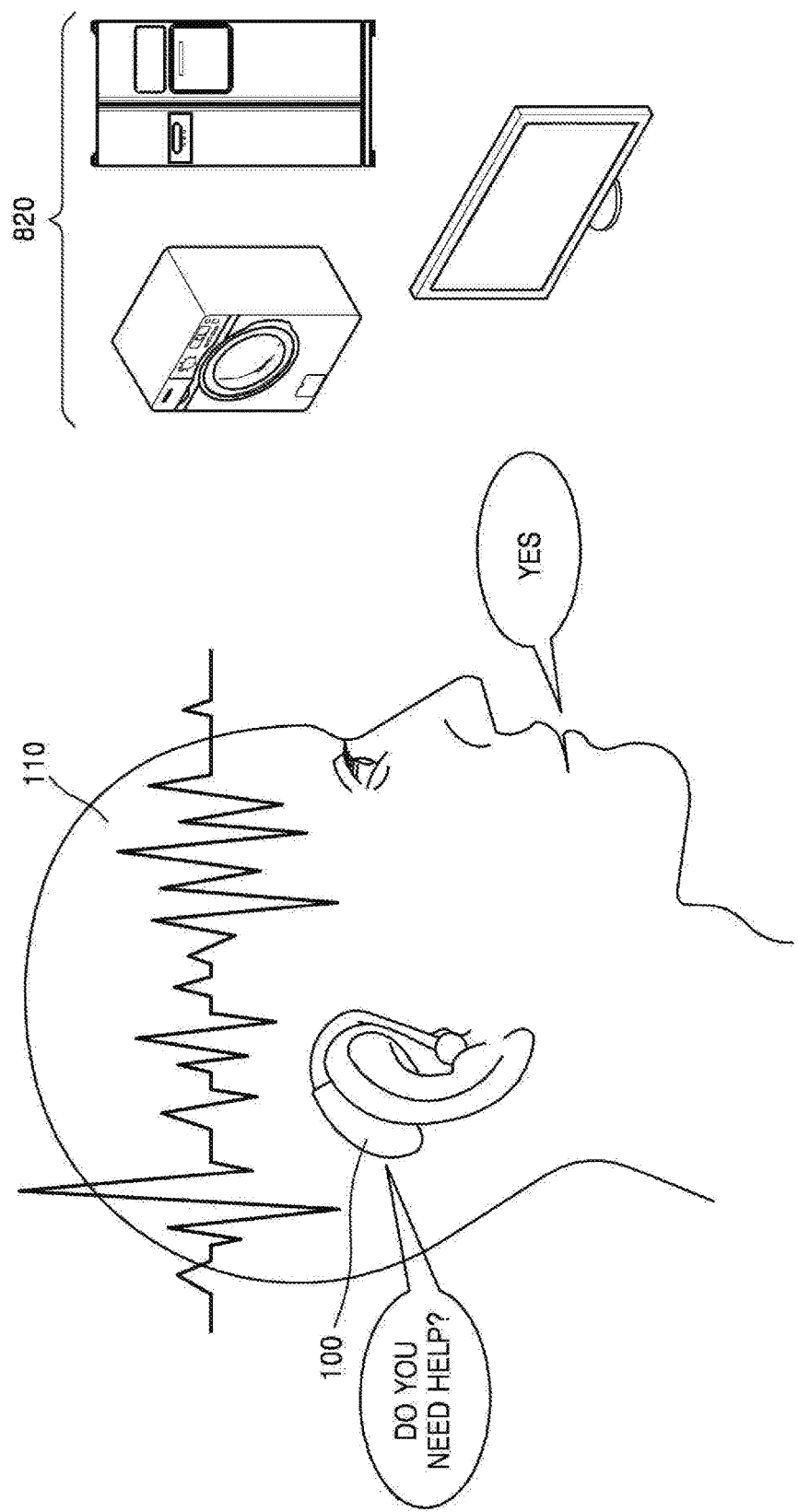
FIG. 8 is a diagram for describing a device receiving a user input for searching for a peripheral device, according to an embodiment of the present disclosure.

FIG. 8 is a diagram for describing a device 100 receiving a user input for searching for at least one peripheral device 820, according to an embodiment of the present disclosure.

The device 100 may receive a user input for searching for the at least one peripheral device 820. The user input may be a condition for the device 100 to search for the at least one peripheral device 820.

For example, the device 100 may receive the user input based on at least one of voice recognition, button manipulation, and a UI screen.

For example, referring to FIG. 8, the device 100 that is worn on an ear of the user 110 may output a voice signal of "Do you need help?" when a stress index of the user 110 is equal to or higher than a threshold value to request the user 110 to perform the user input. After requesting for the user input, the device 100 may recognize the voice of the user 110, such as "Yes" or "Device information request" to receive the user input.

Also, after receiving the user input, the device 100 may transmit a search signal to the at least one peripheral device 820.

By receiving the user input before transmitting the search signal, power of the device 100 may be efficiently consumed and malfunction of the device 100 may be prevented.

Figure 9:
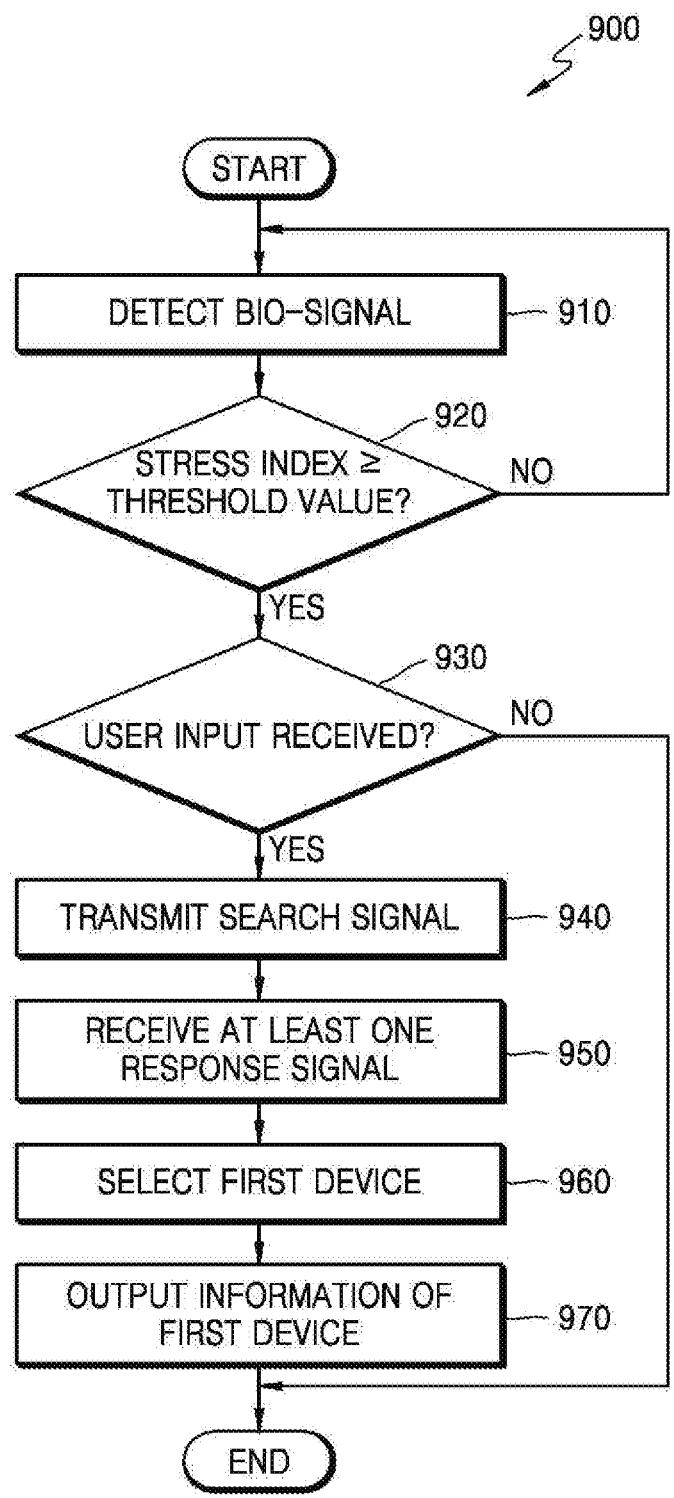
FIG. 9 is a flowchart of a method of receiving, by a device, a user input for searching for a peripheral device, and outputting, by the device, information of a first device, according to an embodiment of the present disclosure.

FIG. 9 is a flowchart of a method 900 of receiving, by the device, a user input for searching for the at least one peripheral device 820, and outputting, by the device 100, information of the first device, according to an embodiment of the present disclosure.

Since operations 910, 920, and 950 through 970 respectively correspond to operations 210, 220, and 240 through 260 of FIG. 2A, details thereof are not provided again.

In operation 910, the device 100 may detect a bio-signal of the user 110.

In operation 920, the device 100 may calculate a stress index of the user 110 based on the bio-signal and determine whether the stress index is equal to or higher than a threshold value.

If it is determined that the stress index is equal to or higher than the threshold value, it is determined whether the device 100 received a user input for searching for the at least one peripheral device 820 from the user, in operation 930.

If it is determined that the user input is received, the device 100 may transmit a search signal to the at least one peripheral device 820 in operation 940.

In operation 950, the device 100 may receive at least one response signal from the at least one peripheral device 820 that received the search signal.

In operation 960, the device 100 may select the first device from among the at least one peripheral device 820 based on the at least one response signal In operation 970, the device 100 may output information of the first device.

In FIG. 9, the device 100 receives the user input after it is determined that the stress index is equal to or higher than the threshold value and before the at least one peripheral device 820 is searched for based on the search signal and the at least one response signal. However, unlike FIG. 9, the device 100 may receive a user input for selecting the first device after it is determined that the stress index is equal to or higher than the threshold value and the at least one peripheral device 820 is searched for based on the search signal and the at least one response signal and before the first device is selected. For example, operation 930 may be performed after operation 950 and before operation 960. Also, the device 100 may receive a user input for outputting the information of the first device after the first device is selected and before the information of the first device is output. For example, operation 930 may be performed after operation 960 and before operation 970.

Figure 10:
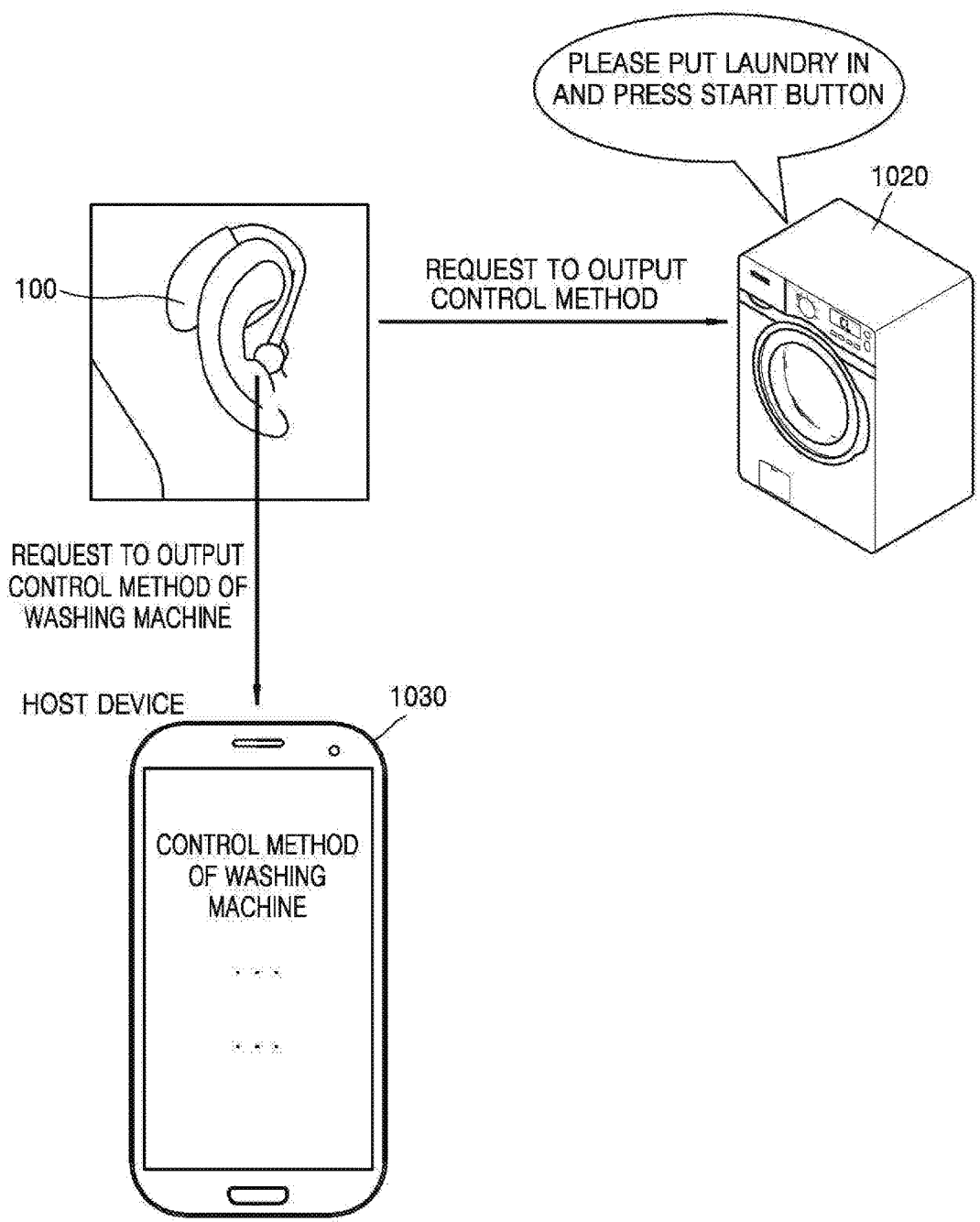
FIG. 10 is a diagram for describing a device requesting a first device and a host device to output information of the first device, according to an embodiment of the present disclosure.

FIG. 10 is a diagram for describing a device 100 requesting the first device and a host device 1030 to output information of the first device, according to an embodiment of the present disclosure.

As described above, the device 100 may directly output the information of the first device. Alternatively, according to an embodiment, the device 100 may request the first device to output the information of the first device.

For example, referring to FIG. 10, the device 100 may select a washing machine 1020 as the first device based on a response signal, and request the washing machine 1020 to output information about a control method of the washing machine 1020. For example, the washing machine 1020 may output information about the control method as a voice, such as "Please put laundry in and press start button".

As another example that is not shown in FIG. 10, the device 100 may request the washing machine 1020 to output state information. The washing machine 1020 may output the state information at a point of time when the device 100 requested. For example, the washing machine 1020 may output the state information as a voice, such as "Washing".

The device 100 according to an embodiment may request the host device 1030 to output the information of the first device.

Here, the host device 1030 may be a device capable of controlling the device 100 outputting the information of the first device. For example, an application for controlling the device 100 may be installed in the host device 1030. Also, a widget corresponding to the application installed in the host device 1030 may be installed in the device 100. The host device 1030 may execute the application to transmit data to the device 100, to receive data from the device 100, or instruct the device 100 to perform a certain operation. For example, the host device 1030 may control power of the device 100.

The host device 1030 may be embodied in any one of various forms, such as a smart phone, a tablet PC, and a computer. Also generally, a user of the device 100 may be the same as a user of the host device 1030.

Referring to FIG. 10, the device 100 may request the host device 1030 to output the information about the control method of the washing machine 1020, i.e., the information of the first device. Then, the host device 1030 may output the control method in at least one of text, an image, a moving image, and voice.

The device 100 requests the first device or the host device 1030 to output the information of the first device, thereby providing the information of the first device to the user 110 via any one of various methods.

Figure 11:
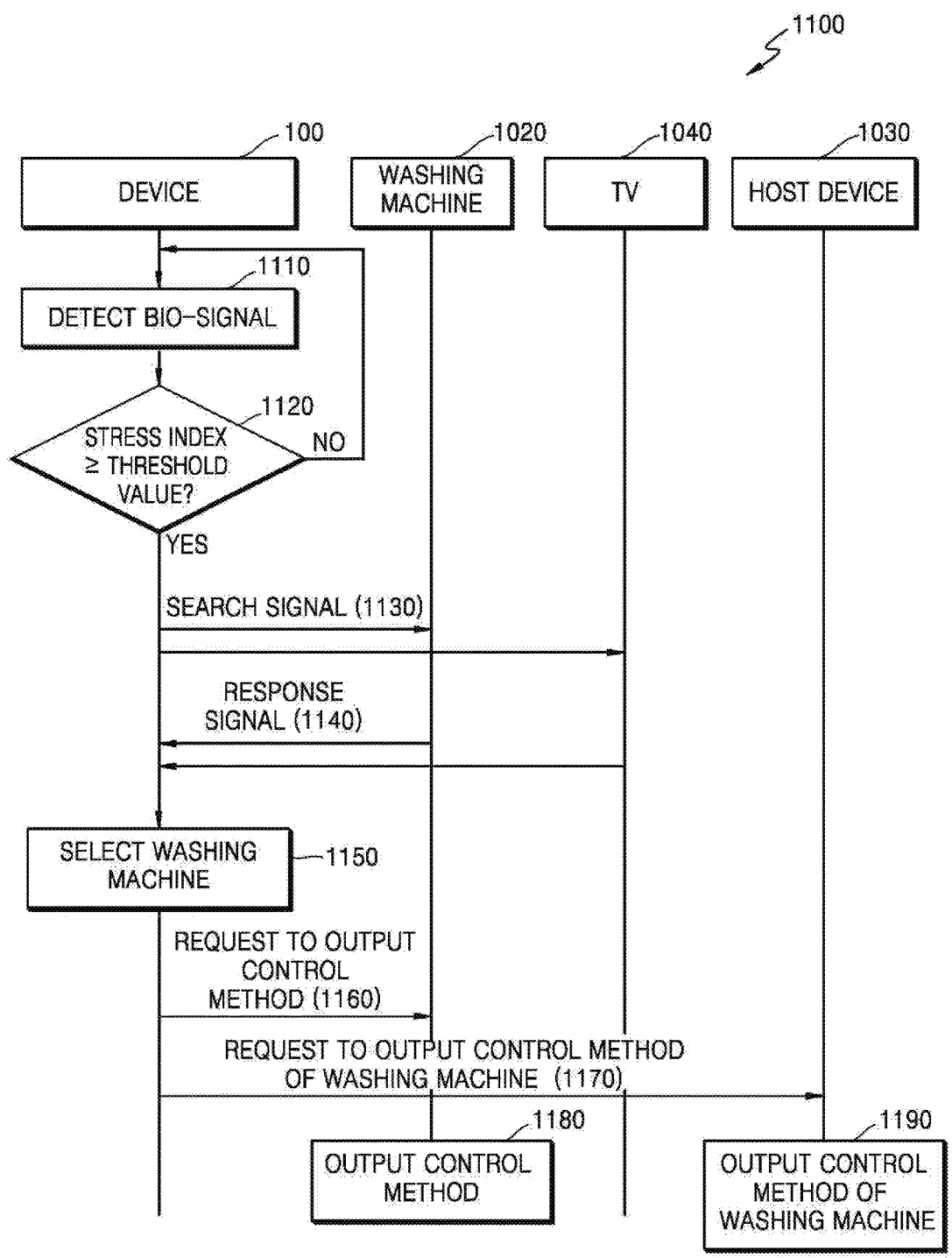
FIG. 11 is a flowchart of a method of requesting, by a device, a first device and a host device to output information of the first device, according to an embodiment of the present disclosure.

FIG. 11 is a flowchart of a method 1100 of requesting, by the device 100, the first device and the host device 1030 to output information of the first device, according to an embodiment of the present disclosure.

Since operations 1110 through 1150 and TV 1040 may correspond to operations 510 through 550 and TV 430 of FIG. 5, repeated descriptions thereof are omitted.

In operation 1160, the device 100 may request the first device to output the information of the first device. For example, the device 100 may request the washing machine 1020 selected as the first device in operation 1150 to output the information about the control method of the washing machine 1020.

In operation 1180, the first device may output the information of the first device based on the request in operation 1160.

The first device may output the information of the first device in at least one of visual information, auditory information, and a vibration signal. However, a form of the information of the first device is not limited thereto.

For example, the first device may output, on a displayer, the information of the first device including at least one of a character, a number, a sign, a still image, and a moving image. Also, when the first device includes a projector, the information of the first device including at least one of a character, a number, a sign, a still image, and a moving image may be externally projected from the first device.

As another example, the first device may output the information of the first device by flicker of a manipulation button or a display panel of the first device. For example, when the first device is requested to output the information of the first device from the device 100, the first device may make a manipulation button flicker based on a current state of the first device.

As another example, the first device may output the information of the first device as auditory information through a sound outputter.

As another example, the first device may output the information of the first device as a vibration signal through a vibration motor.

For example, the washing machine 1020 may output the information about the control method of the washing machine 1020 as a voice, according to the request of the device 100.

In operation 1170, the device 100 may request the host device 1030 to output the information of the first device.

For example, the device 100 may request the host device 1030 to output the information about the control method of the washing machine 1020 that is selected as the first device in operation 1150.

The device 100 may be paired with the host device 1030 to transmit data to the host device 1030 or to receive data from the host device 1030. Also, in order to pair with the host device 1030, the device 100 may perform authentication and registration processes.

For example, the device 100 may communicate with the host device 1030 via a wired/wireless communication method. For example, the device 100 may communicate with the host device 1030 through a data cable connected to the host device 1030. Also, the device 100 may communicate with the host device 1030 through a wireless communication method, such as NFC, ZigBee, BT, or UWB communication.

Also, the device 100 may communicate with the host device 1030 through an external server. For example, the device 100 may transmit data to the host device 1030 or receive data from the host device 1030 via a server, through a 3G or 4G communication network or WiFi.

A method of the device 100 communicating with the host device 1030 is not limited thereto. For example, the device 100 may communicate with the host device 1030 by using ultrasonic waves, infrared ray, or a body area network (BAN).

In operation 1190, the host device 1030 may output the information of the first device according to the request of operation 1170.

The host device 1030 may output the information of the first device in at least one of visual information, auditory information, and a vibration signal. However, a form of the information of the first device is not limited thereto.

For example, the host device 1030 may output, on a displayer, the information of the first device including at least one of a character, a number, a sign, a still image, and a moving image. Also, when the host device 1030 includes a projector, the information of the first device including at least one of a character, a number, a sign, a still image, and a moving image may be externally projected from the host device 1030.

As another example, the host device 1030 may output the information of the first device as auditory information through a sound outputter.

As another example, the host device 1030 may output the information of the first device as a vibration signal through a vibration motor.

For example, the host device 1030 may output the information about the control method of the washing machine 1020 as a moving image according to the request of the device 100.

As described above with reference to FIGS. 10 and 11, the device 100 may request the first device or the host device 1030 to output the information of the first device. Also, the device 100 may request a second device (not shown) among peripheral devices to output the information of the first device. For example, the device 100 may select the washing machine 1020 as the first device and request a TV (i.e., the second device) closest to the device 100 to output the information of the washing machine 1020. As another example, the device 100 may select the washing machine 1020 as the first device and request a wearable device (for example, a hearing aid, an earphone, glasses, goggles, a helmet, a hair band, HMD, a bracelet, a ring, a necklace, a shoe, a belt, a sticker, or a clip) worn on the user 110 to output the information of the washing machine 1020.

The second device may output the information of the first device as visual information, auditory information, and a vibration signal. However, a form of the information of the first device is not limited thereto.

For example, the second device may output, the information of the first device including at least one of a character, a number, a sign, a still image, a moving image, and lighting. Also, when the second device includes a projector, the information of the first device including at least one of a character, a number, a sign, a still image, and a moving image may be externally projected from the first device.

As another example, the second device may output the information of the first device as auditory information through a sound outputter.

As another example, the second device may output the information of the first device as a vibration signal through a vibration motor.

For example, when the second device is a speaker, the speaker may output the information of the first device as a voice or sound signal.

As described above with reference to FIGS. 1, 2A to 2D, 3, 4A and 4B, 5, 6A and 6B, 7 to 11, the device 100 according to an embodiment may search for at least one peripheral device by communicating with the at least one peripheral device.

Hereinafter, a method of searching for, by the device 100, at least one peripheral device without directly communicating with the at least one peripheral device will be described with reference to FIGS. 12A and 12B, 13, 14, 15A, 15B, and 16 to 19.

Figure 12A:
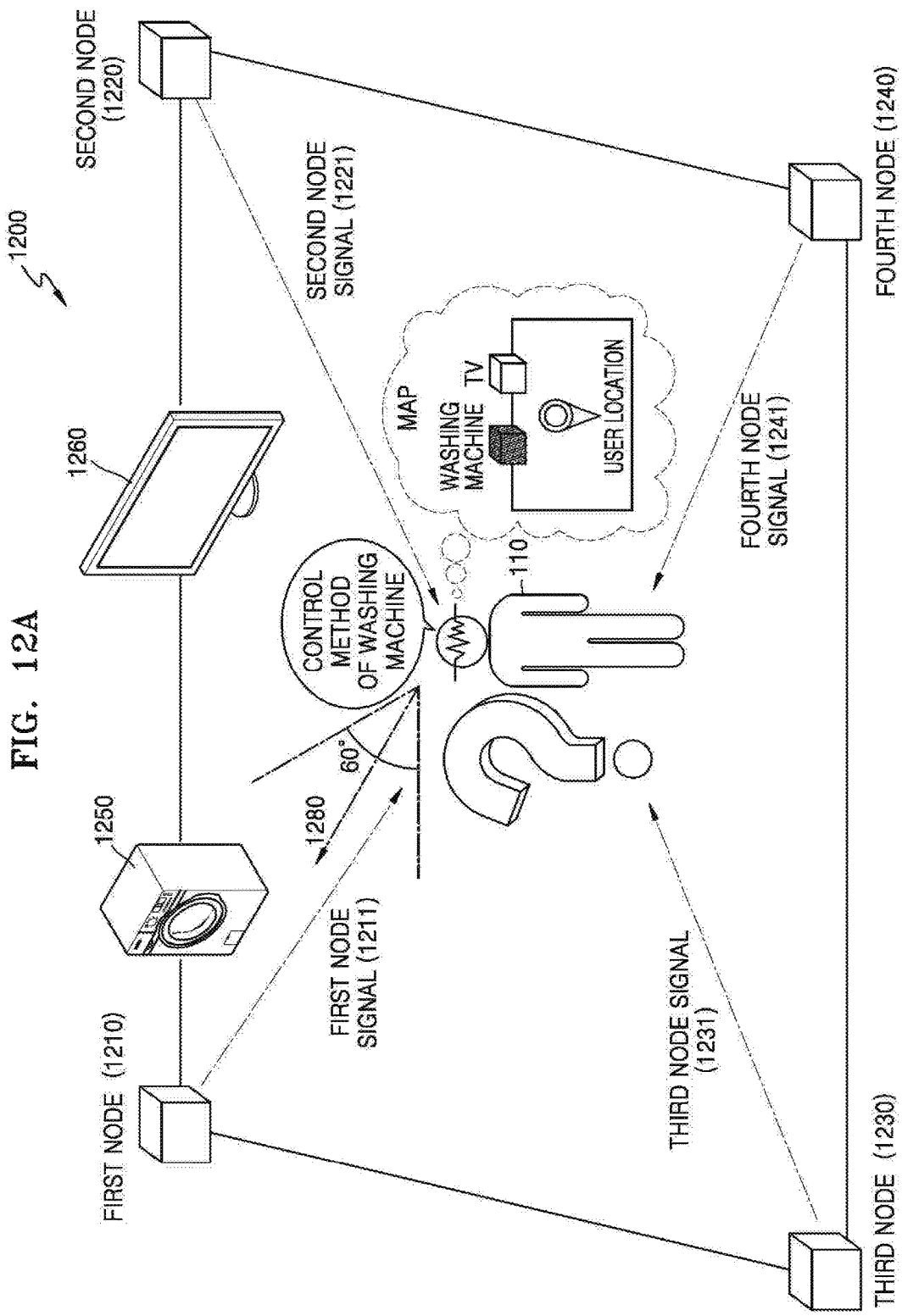
FIGS. 12A and 12B are diagrams for describing a device determining an indoor location, detecting a direction of the device, selecting a first device, and outputting information of the first device, according to various embodiments of the present disclosure.
Figure 12B:
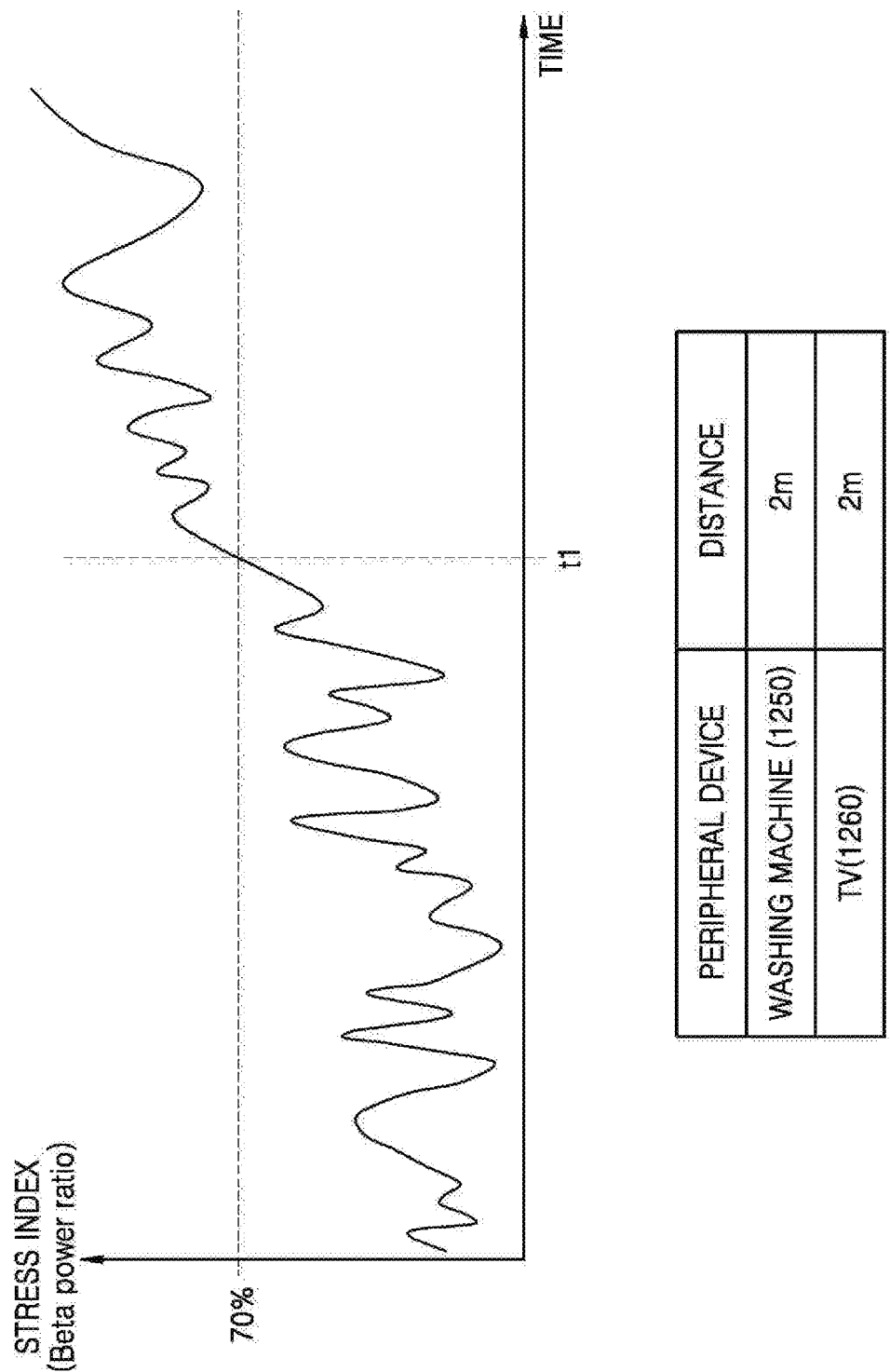

FIGS. 12A and 12B are diagrams 1200 for describing a device 100 determining an indoor location, detecting a direction of the device 100, selecting the first device, and outputting information of the first device, according to various embodiments of the present disclosure.

FIG. 12B shows a graph of a stress index according to time. When the user 110 is not stressed, the stress index of the user 110, calculated by the device 100, may be lower than a threshold value. However, when the user 110 is stressed, the stress index of the user 110, calculated by the device 100, may be equal to or higher than the threshold value. For example, the user 110, who is a dementia patient, may not remember how to manipulate a washing machine 1250 due to intermittent memory loss at a point of time t1 and suffer from mental stress. Also, the stress index of the user 110 may exceed the threshold value at the point of time t1. For example, as described above with reference to FIG. 2A, the stress index may be a beta power ratio calculated based on EEG measured from the user 110. The beta power ratio may have a value between 0% to 100%. Also, a threshold value of the beta power ratio may be set to 70% by the user 110 and may vary according to location information of the user 110 or current time information.

When the stress index is equal to or higher than the threshold value, the device 100 may receive a user input of requesting to search for peripheral devices, i.e., the washing machine 1250 and a TV 1260, from the user 110. For example, when the stress index is equal to or higher than the threshold value, the device 100 may output a voice signal of "Do you need help?" to request the user 110 to perform the user input. After requesting for the user input, the device 100 may recognize the voice of the user 110, such as "Yes" or "Device information request", to receive the user input. As another example, when the stress index is equal to or higher than the threshold value, the device 100 may output a vibration signal to request the user 110 for a user input. After requesting for the user input, the device 100 may receive the user input requesting the device 100 to search for the washing machine 1250 and the TV 1260 based on at least one of voice recognition, button manipulation, and a UI screen. If the user 110 does not want help from the device 100 despite that the stress index is equal to or higher than the threshold value, the user 110 may end an operation of the device 100 based on at least one of voice recognition, button manipulation, and a UI screen.

Referring to FIG. 12A, the device 100 may determine an indoor location of the device 100 at the point of time t1 in order to search for a peripheral device that stressed the user 110. For example, when the device 100 receives the user input of requesting the device 100 to search for the washing machine 1250 and the TV 1260, the device 100 may determine the indoor location of the device 100 based on signal strength of first through fourth node signals 1211 through 1241 respectively from first through fourth nodes 1210 through 1240, and locations of the first through fourth nodes 1210 through 1240. An example of the device 100 determining the indoor location will be described later with reference to FIG. 14.

Here, the first through fourth nodes 1210 through 1240 may be devices used to determine the indoor location of the device 100 that outputs information of the first device. The first through fourth nodes 1210 through 1240 may transmit pre-set data to the device 100 or receive pre-set data from the device 100. For example, the first through fourth nodes 1210 through 1240 may include an antenna and a WiFi access point, or a BT tag.

The device 100 may select one of the washing machine 1250 and the TV 1260 as the first device based on the indoor location of the device 100 and a direction 1280 of the device 100. For example, the device 100 may select the washing machine 1250 that is located within a left and right range of 30° based on the direction 1280 and closest to the device 100, as the first device. The direction 1280 may vary depending on a type of the device 100. The device 100 may detect the direction 1280 that is pre-set based on a part of the device 100 based on at least one of an acceleration sensor, a terrestrial magnetic sensor, and a gyroscope sensor.

FIG. 12B shows distances between the device 100 and the washing machine 1250 and between the device 100 and the TV 1260, which are measured by the device 100. The device 100 may calculate the distances between the device 100 and the washing machine 1250 and between the device 100 and the TV 1260 by comparing the indoor location of the device 100 at the point of time t1 with location information of the washing machine 1250 and the TV 1260 pre-stored in the device 100. For example, the device 100 may be away from the washing machine 1250 and the TV 1260 by 2 m. The device 100 is away from the washing machine 1250 and the TV 1260 by the same distance, but since the washing machine 1250 is located within the left and right range of 30° based on the direction 1280, whereas the TV 1260 is not, the device 100 may select the washing machine 1250 as the first device. Also, the device 100 may output a control method of the washing machine 1250 to help the user 110, who does not remember how to control the washing machine 1250.

As described above, the device 100 may search for the washing machine 1250 and the TV 1260 based on the indoor location of the device 100 and the direction 1280 of the device 100 without having to communicate with the washing machine 1250 and the TV 1260.

FIG. 13 is a flowchart of a method 1300 of determining, by the device 100, the indoor location, detecting the direction 1280 of the device 100, selecting the first device, and outputting the information of the first device, according to an embodiment of the present disclosure.

Since operations 1320, 1330, and 1380 may respectively correspond to operations 210a, 220a, and 260a of FIG. 2A, overlapping details thereof are not provided.

In operation 1310, the device 100 may store indoor locations of the washing machine 1250, the TV 1260, and the first through fourth nodes 1210 through 1240. The indoor locations of the washing machine 1250 and the TV 1260 may indicate intrinsic locations in a house or building where the user 110 is located. The indoor locations of the first through fourth nodes 1210 through 1240 may indicate intrinsic locations in the house or the building where the user 110 is located. For example, the indoor locations of the washing machine 1250, the TV 1260, and the first through fourth nodes 1210 through 1240 may be 2-dimensional (2D) coordinates set based on a certain starting point. Also, the device 100 may register, edit, and delete the indoor locations of the washing machine 1250 and the TV 1260.

In operation 1320, the device 100 may detect a bio-signal of the user 110.

In operation 1330, the device 100 may calculate a stress index of the user 110 based on the bio-signal and determine whether the stress index is equal to or higher than a threshold value.

In operation 1340, the device 100 may receive the first through fourth node signals 1211 through 1241 respectively from the first through fourth nodes 1210 through 1240.

The first through fourth node signals 1211 through 1241 may include ID information respectively of the first through fourth nodes 1210 through 1240. For example, the first node signal 1211 may include the ID information of the first node 1210.

Also, when it is determined that the stress index is equal to or higher than the threshold value, the device 100 may request the first through fourth nodes 1210 through 1240 to transmit the first through fourth node signals 1211 through 1241. For example, when it is determined that the stress index is equal to or higher than the threshold value, the device 100 may transmit a search signal to the first through fourth nodes 1210 through 1240, and receive the first through fourth node signals 1211 through 1241 respectively from the first through fourth nodes 1210 through 1240.

In FIG. 13, the device 100 receives the first through fourth node signals 1211 through 1241 when the stress index is equal to or higher than the threshold value, but alternatively, the device 100 may receive the first through fourth node signals 1211 through 1241 irrelevantly to the stress index. For example, operation 1340 may be performed before operation 1330.

The first through fourth nodes 1210 through 1240 may communicate with the device 100 via a wireless communication method. For example, the first through fourth nodes 1210 through 1240 may communicate with the device 100 via a wireless communication method, such as WiFi, NFC, ZigBee, BT, UWB communication, ultrasonic waves, and infrared ray.

In operation 1350, the device 100 may determine the indoor location of the device 100 based on signal strength of the first through fourth node signals 1211 through 1241 and locations of the first through fourth nodes 1210 through 1240.

The indoor location of the device 100 may indicate a location of the device 100 in a house or building where the user 110 is located. For example, the indoor location of the device 100 may be a 2D coordinate set based on a certain starting point. In this case, the 2D coordinate indicating the indoor location of the device 100 and 2D coordinates indicating indoor locations of peripheral devices, i.e., the washing machine 1250 and the TV 1260, may be set based on the same starting point.

For example, the device 100 may calculate distances between the device 100 and the first through fourth nodes 1210 through 1240 based on the signal strength of and ID information included in the first through fourth node signals 1211 through 1241. Also, the device 100 may determine the indoor location of the device 100 based on the calculated distances and the locations of the first through fourth nodes 1210 through 1240.

As another example, the device 100 may determine the indoor location of the device 100 based on a node signal finger print map according to indoor locations. In detail, the node signal finger print map according to indoor locations may denote information about the signal strength of the first through fourth node signals 1211 through 1241 detected intrinsically by the device 100 according to indoor locations. The device 100 may store the node signal finger print map, and determine the indoor location of the device 100 by pattern-matching or comparing the node signal finger print map with the signal strength of the first through fourth node signals 1211 through 1241 currently received by the device 100.

Accuracy of the indoor location of the device 100 increases when the number of node signals increases.

An example of the device 100 determining the indoor location of the device 100 will be described later with reference to FIG. 14.

In operation 1360, the device 100 may detect the direction 1280 of the device 100.

The device 100 may detect the direction 1280 that is pre-set based on a part of the device 100, based on at least one of an acceleration sensor, a terrestrial magnetic sensor, and a gyroscope sensor.

The direction 1280 may vary depending on a type of the device 100. For example, when the device 100 is worn on an ear, the direction 1280 may be perpendicular to a face of the user 110. As another example, when the device 100 is a glasses type, the direction 1280 may be perpendicular to lenses.

In operation 1370, the device 100 may select one of the washing machine 1250 and the TV 1260, of which the indoor locations are stored in the device 100 in operation 1310, as the first device, based on the indoor location and direction 1280 of the device 100. For example, the device 100 may determine one of the washing machine 1250 and the TV 1260, which is located within a certain range based on the direction 1280 and closest to the indoor location of the device 100, as the first device.

In operation 1380, the device 100 may output the information of the first device.

Figure 14:
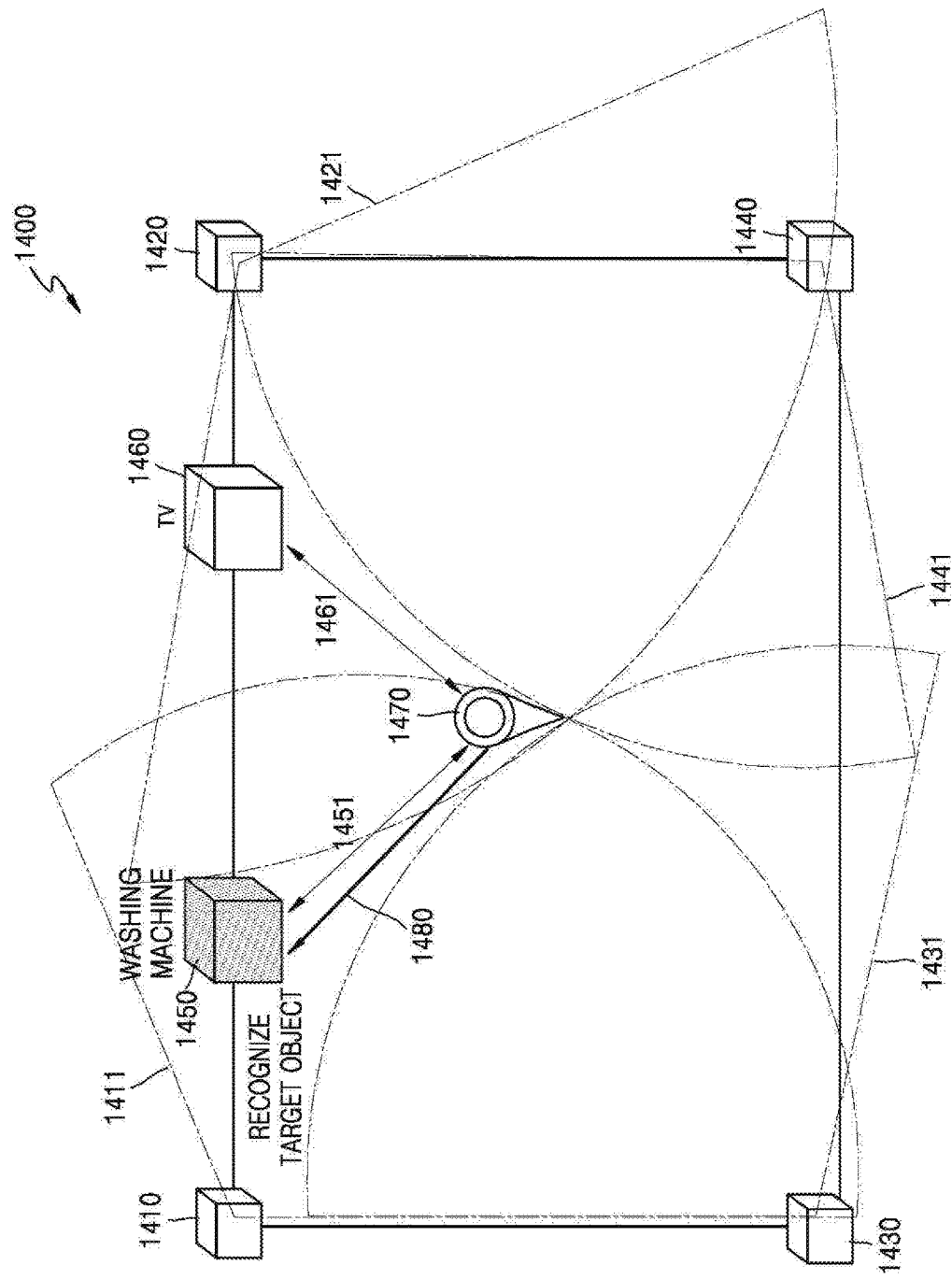
FIG. 14 is a diagram for describing a device selecting a first device based on an indoor location and a direction of the device, according to an embodiment of the present disclosure.

FIG. 14 is a conceptual diagram 1400 for describing an example of the device 100 selecting the first device based on an indoor location 1470 and a direction 1480 of the device 100, according to an embodiment of the present disclosure.

Referring to FIG. 14, first through fourth nodes 1410 through 1440, a plurality of peripheral devices, i.e., a washing machine 1450 and a TV 1460, and the device 100 outputting information of the washing machine 1450 and the TV 1460 may be located at home.

The device 100 may determine a node that transmitted a node signal based on ID information included in the node signal. Also, the device 100 may measure a distance between the device 100 and the node based on signal strength of the node signal. Hereinafter, for convenience of description, a distance between the device 100 and a $n^{th}$ node will be referred to as a $n^{th}$ node distance. For example, when signal strength or receiving sensitivity of a $n^{th}$ node signal from the $n^{th}$ node is high, the $n^{th}$ node distance may be short.

The device 100 may determine the indoor location 1470 of the device 100 based on indoor locations of the first through fourth nodes 1410 through 1440 and distances between the device 100 and the first through fourth nodes 1410 through 1440.

For example, the device 100 storing an indoor location of a $n^{th}$ node may determine the indoor location 1470 of the device 100 at one point on a circle having a radius equal to a $n^{th}$ node distance based on the indoor location of the $n^{th}$ node. Hereinafter, for convenience of description, the circle having the radius equal to the $n^{th}$ node distance based on the indoor location of the $n^{th}$ node may be referred to as a $n^{th}$ node circle.

Accordingly, the device 100 may determine the indoor location 1470 of the device 100 at a point where different $n^{th}$ node circles meet.

For example, referring to FIG. 14, parts of first through fourth node circles 1411 through 1441 are shown. The device 100 may determine the indoor location 1470 of the device 100 to be a point where the first through fourth node circles 1411 through 1441 meet.

Also, the device 100 may select the first device from among the washing machine 1450 and the TV 1460 based on the indoor location 1470 and the direction 1480 of the device 100. For example, referring to FIG. 14, a distance 1451 between the washing machine 1450 and the device 100 may be the same as a distance 1461 between the TV 1460 and the device 100. However, since the washing machine 1450 is located in the direction 1480 of the device 100 based on the indoor location 1470 of the device 100, the device 100 may select the washing machine 1450 as the first device.

FIGS. 15A and 15B are diagrams for describing a device 100 determining an indoor location of the device 100 and searching for peripheral devices, according to various embodiments of the present disclosure.

FIG. 15B shows a graph of a stress index according to time. When the user 110 is not stressed, a stress index of the user 110, calculated by the device 100, may be lower than a threshold value. However, when the user 110 is stressed, the stress index may be equal to or higher than the threshold value. For example, at a point of time t1, the user 110, who is a dementia patient, may not remember how to manipulate a washing machine 1550 due to intermittent memory loss and suffer from mental stress. Also, the stress index may exceed the threshold value at the point of time t1. For example, as described above with reference to FIG. 2A, the stress index may be a beta power ratio calculated based on EEG measured from the user 110. The beta power ratio may have a value from 0% to 100%. Also, a threshold value of the beta power ratio may be set to 70% by the user 110 and may vary according to location information of the user 110 or current time information.

When the stress index is equal to or higher than the threshold value, the device 100 may receive a user input requesting the device 100 to search for the peripheral devices, i.e., the washing machine 1550, a TV 1560, and a refrigerator 1570, from the user 110. For example, when the stress index is equal to or higher than the threshold value, the device 100 may output a voce signal of "Do you need help?" to request the user 110 to perform the user input. After requesting for the user input, the device 100 may recognize the voice of the user 110, such as "Yes" or "Device information request", to receive the user input. As another example, when the stress index is equal to or higher than the threshold value, the device 100 may output a vibration signal to request the user 110 for a user input. After requesting for the user input, the device 100 may receive the user input requesting the device 100 to search for the washing machine 1550, the TV 156, and the refrigerator 1570 based on at least one of voice recognition, button manipulation, and a UI screen. If the user 110 does not want help from the device 100 despite that the stress index is equal to or higher than the threshold value, the user 110 may end an operation of the device 100 based on at least one of voice recognition, button manipulation, and a UI screen.

Referring to FIG. 15A, the device 100 may determine an indoor location of the device 100 at the point of time t1 in order to search for a peripheral device that stressed the user 110. For example, when the device 100 receives the user input of requesting the device 100 to search for the washing machine 1550, the TV 1560, and the refrigerator 1570, the device 100 may determine the indoor location of the device 100 based on signal strength of first through fourth node signals 1511 through 1541 respectively from first through fourth nodes 1510 through 1540, and locations of the first through fourth nodes 1510 through 1540. An example of the device 100 determining the indoor location will be described later with reference to FIG. 17.

The device 100 may select one of the washing machine 1550, the TV 1560, and the refrigerator 1570 as the first device based on the indoor location of the device 100. For example, the device 100 may select the washing machine 1550 that is located closest to the device 100, as the first device.

FIG. 15B shows distances between the device 100 and the peripheral devices, i.e., the washing machine 1550, the TV 1560, and the refrigerator 1570, which are measured by the device 100. The device 100 may calculate the distances between the device 100, and the washing machine 1550, the TV 1560, and the refrigerator 1570 by comparing the indoor location of the device 100 at the point of time t1 with location information of the washing machine 1550, the TV 1560, and the refrigerator 1570 pre-stored in the device 100. For example, the device 100 may be away from the washing machine 1550 by 1 m, away from the TV 1560 by 2 m, and away from the refrigerator 1570 by 20 m. The device 100 may select the washing machine 1550 that is closest to the device 100 as the first device. Also, the device 100 may output a control method of the washing machine 1550 to help the user 110, who does not remember how to control the washing machine 1550.

As described above, the device 100 may search for the washing machine 1550, the TV 1560, and the refrigerator 1570 based on the indoor location of the device 100 without having to communicate with the washing machine 1550, the TV 1560, and the refrigerator 1570.

Figure 16:
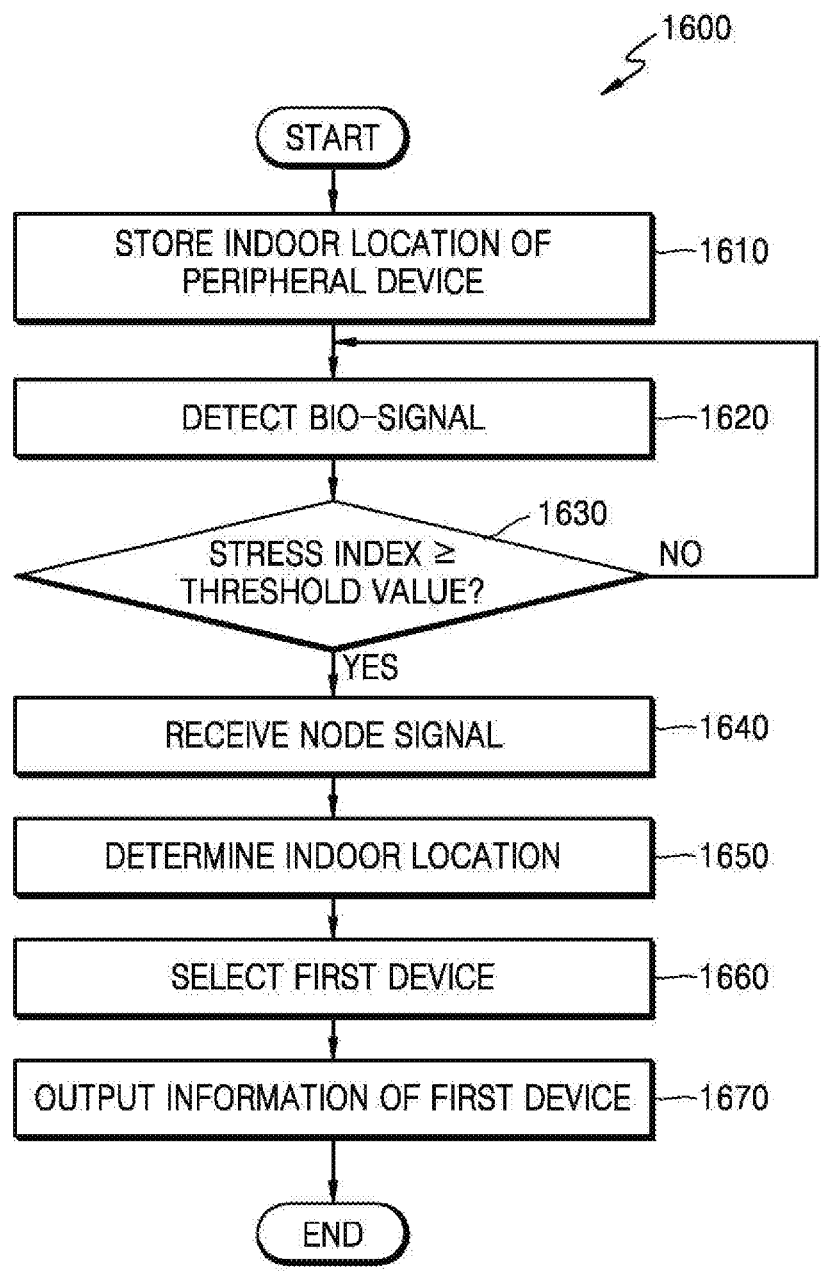
FIG. 16 is a flowchart of a method of determining, by a device, an indoor location of the device, and searching for, by the device, peripheral devices, according to an embodiment of the present disclosure.

FIG. 16 is a flowchart of a method 1600 of determining, by the device 100, the indoor location of the device 100, and searching for, by the device 100, the peripheral devices, i.e., the washing machine 1550, the TV 1560, and the refrigerator 1570, according to an embodiment of the present disclosure.

Since operations 1610 through 1650 and 1670 may respectively correspond to operations 1310 through 1350 and 1380 of FIG. 13, overlapping details thereof are not provided.

In operation 1610, the device 100 may store indoor locations of the washing machine 1550, the TV 1560, the refrigerator 1570, and the first through fourth nodes 1510 through 1540.

In operation 1620, the device 100 may detect a bio-signal of the user 110.

In operation 1630, the device 100 may calculate a stress index of the user 110 based on the bio-signal and determine whether the stress index is equal to or higher than a threshold value.

In operation 1640, the device 100 may receive the first through fourth node signals 1511 through 1541 respectively from the first through fourth nodes 1510 through 1540.

In operation 1650, the device 100 may determine the indoor location of the device 100 based on signal strength of the first through fourth node signals 1511 through 1541 and the indoor locations of the first through fourth nodes 1510 through 1540.

In operation 1660, the device 100 may select one of the washing machine 1550, the TV 1560, and the refrigerator 1570, of which the indoor locations are stored in operation 1610, as the first device based on the indoor location of the device 100.

Also, in operation 1670, the device 100 may output information of the first device.

Figure 17:
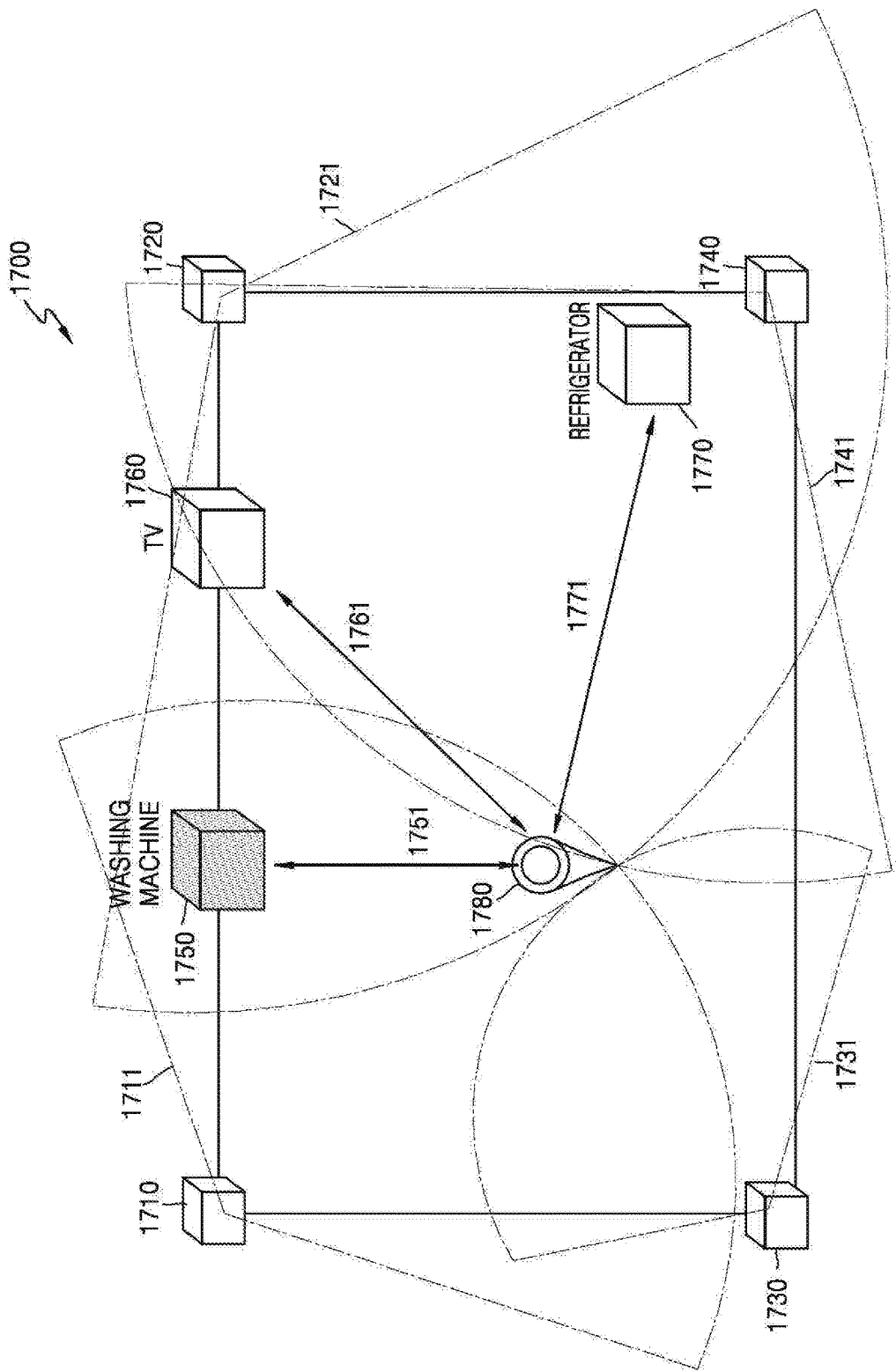
FIG. 17 is a diagram for describing a device selecting a first device based on an indoor location of the device, according to an embodiment of the present disclosure.

FIG. 17 is a diagram 1700 for describing a device 100 selecting the first device based on an indoor location 1780 of the device 100, according to an embodiment of the present disclosure.

Referring to FIG. 17, first through fourth nodes 1710 through 1740, a plurality of peripheral devices, i.e., a washing machine 1750, a TV 1760, and a refrigerator 1170, and the device 100 outputting information of the peripheral devices may be located at home.

As described above with reference to FIG. 14, the device 100 may determine the indoor location 1780 to be a point where first through fourth node circles 1711 through 1741 meet, and thus overlapping details thereof are not provided again.

For example, referring to FIG. 17, since a distance 1751 between the washing machine 1750 and the device 100 is shorter than a distance 1761 between the TV 1760 and the device 100 and a distance 1771 between the refrigerator 1770 and the device 100, the device 100 may select the washing machine 1750 as the first device.

As described above with reference to FIGS. 12A and 12B, 13, 14, 15A and 15B, 16, and 17, the device 100 according to an embodiment may determine an indoor location of the device 100 based on the first through fourth node signals 1211 through 1241. However, a method of determining, by the device 100, an indoor location is not limited thereto.

For example, the device 100 may determine the indoor location of the device 100 based on a surrounding magnetic field. For example, terrestrial magnetism changes according to a structure of a house, a steel frame structure of the house, and a metal included in the house, and thus terrestrial magnetism detected around the device 100 may be different according to the indoor location of the device 100. Accordingly, the device 100 may detect a magnetic field around the device 100 to determine the indoor location of the device 100. Also, the device 100 that stores location information of at least one peripheral device may select the first device from among the at least one peripheral device based on the indoor location of the device 100.

For example, the device 100 may determine the indoor location of the device 100 based on a terrestrial magnetic finger print map according to indoor locations. The terrestrial magnetic finger print map according to indoor locations may include information about a terrestrial magnetic signal intrinsically detected in the device 100 according to indoor locations.

The device 100 may pre-store the terrestrial magnetic finger print map. Also, the device 100 may determine the indoor location of the device 100 by pattern-matching or comparing the terrestrial magnetic finger print map with a terrestrial magnetic signal currently detected in the device 100.

Also, the device 100 may determine the indoor location of the device 100 by pattern-matching the terrestrial magnetic finger print map and a change of the terrestrial magnetic signal detected in the device 100. There may be a plurality of indoor locations matching signal strength of the terrestrial magnetic signal currently detected in the device 100. In this case, the device 100 may determine the indoor location of the device 100 by matching the terrestrial magnetic finger print map not only with the terrestrial magnetic signal currently detected but also with at least one terrestrial magnetic signal detected in the past.

Also, the device 100 may determine the indoor location of the device 100 based on a sound source localization method.

For example, the device 100 may receive information about a voice signal of the user 110 recognized by the washing machine 1750, the TV 1760, and the refrigerator 1770, from the washing machine 1750, the TV 1760, and the refrigerator 1770. For example, the information about the voice signal may include at least one of signal strength of the voice signal and an arrival time delay of the voice signal. Also, the device 100 may store the indoor locations of the washing machine 1750, the TV 1760, and the refrigerator 1770.

The device 100 may determine the indoor location of the device 100 based on the indoor locations of the washing machine 1750, the TV 1760, and the refrigerator 1770, and the signal strength of the voice signal recognized by the washing machine 1750, the TV 1760, and the refrigerator 1770.

As described above with reference to FIGS. 12A and 12B, 13, 14, 15A, 15B, 16, and 17, the device 100 according to an embodiment determines an indoor location of the device 100 to search for at least one peripheral device.

Hereinafter, another method of searching for, by the device 100, a peripheral device without having to directly communicate with the peripheral device will be described with reference to FIGS. 18 and 19.

Figure 18:
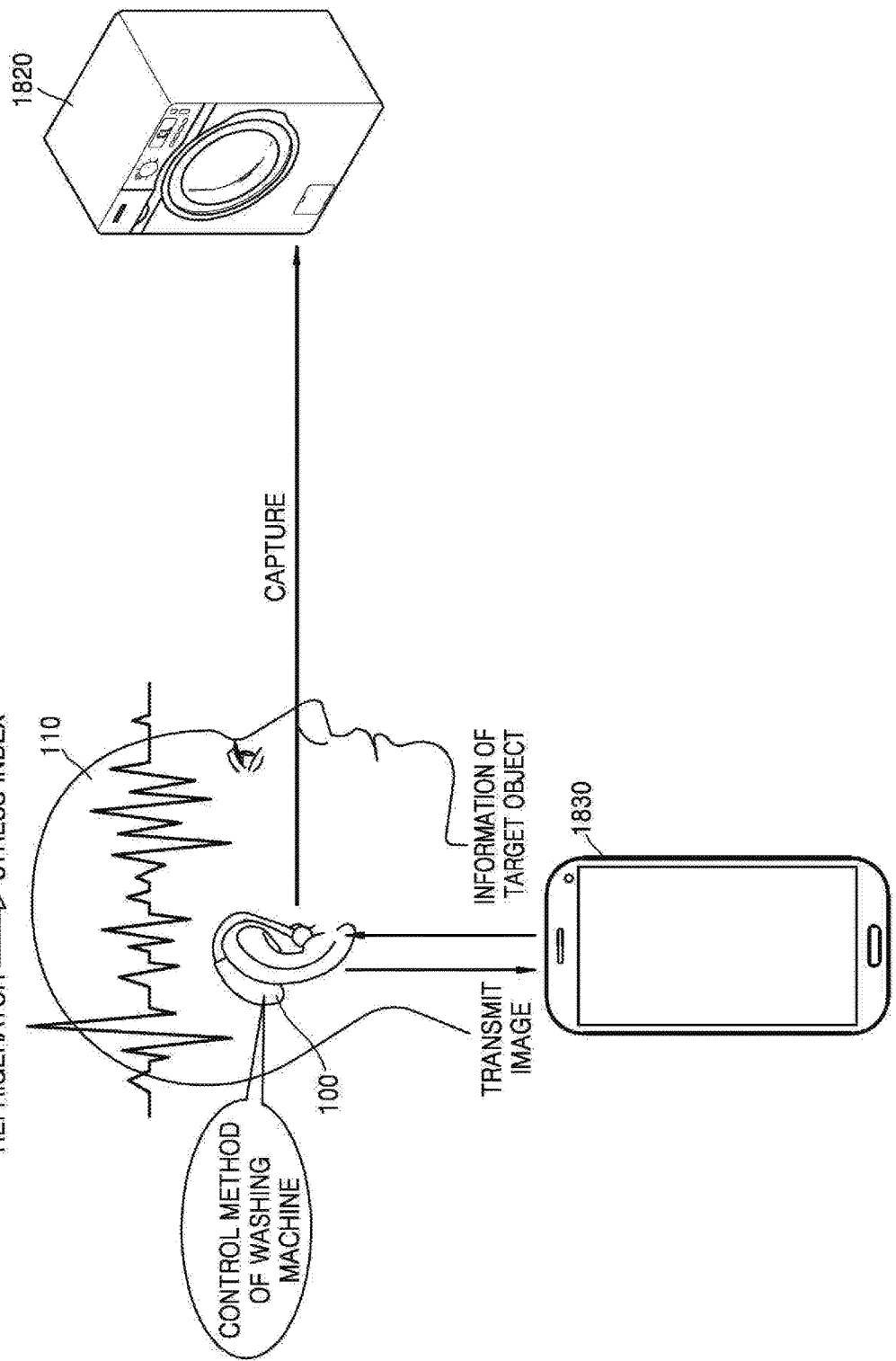
FIG. 18 is a diagram for describing a device capturing an image of a target object and searching for the target object, according to an embodiment of the present disclosure.

FIG. 18 is a diagram for describing a device 100 capturing an image of a target object 1820 and searching for the target object 1820, according to an embodiment of the present disclosure.

When a stress index of the user 110 is equal to or higher than a threshold value, the device 100 may capture an image of the target object 1820 by using a camera included in the device 100. Here, the target object 1820 may be a person or an object around the device 100. The target object 1820 may include a whole or part of an object around the device 100, or a person around the device 100.

The object around the device 100 may be a physical target located around the device 100. For example, the object around the device 100 may include an electronic device, such as a CE device, a home device, or a mobile device. Alternatively, the object around the device 100 may include a physical target, such as a calendar, a notebook, a book, a wallet, or clothes.

The device 100 may search for the target object 1820 that stressed the user 110 by analyzing the captured image. For example, the device 100 may compare the captured image of the target object 1820 and an image of the target object 1820 pre-stored in the device 100 to search for and identify the target object 1820.

Also, the device 100 may transmit the captured image to a host device 1830 and receive information of the target object 1820 from the host device 1830.

As described above with reference to FIG. 10, the host device 1830 may be a device capable of controlling the device 100. Also, the device 100 may be paired up with the host device 1830 to transmit data to the host device 1830 or receive data from the host device 1830. Thus, details overlapping those of FIG. 10 are not provided again.

The host device 1830 may search for the target object 1820 based on the image of the target object 1820 received from the device 100. For example, the host device 1830 may compare the received image of the target object 1820 and an image of the target object 1820 pre-stored in the host device 1830 to search for the target object 1820. Also, the host device 1830 may transmit the information of the target object 1820 to the device 100.

For example, the device 100 may capture the image of the target object 1820, i.e., a washing machine, when a stress index of the user 110 is equal to or higher than a threshold value. Then, the device 100 may transmit the captured image to the host device 1830. Also, the host device 1830 may search for the target object 1820 by comparing the received image with an image of the target object 1820 pre-stored in the host device 1830. Also, the host device 1830 may transmit information about a control method of the target object 1820 to the device 100.

As described above, the device 100 according to an embodiment may search for the target object 1820 by capturing the image of the target object 1820, even if the device 100 is unable to communicate with the target object 1820.

Figure 19:
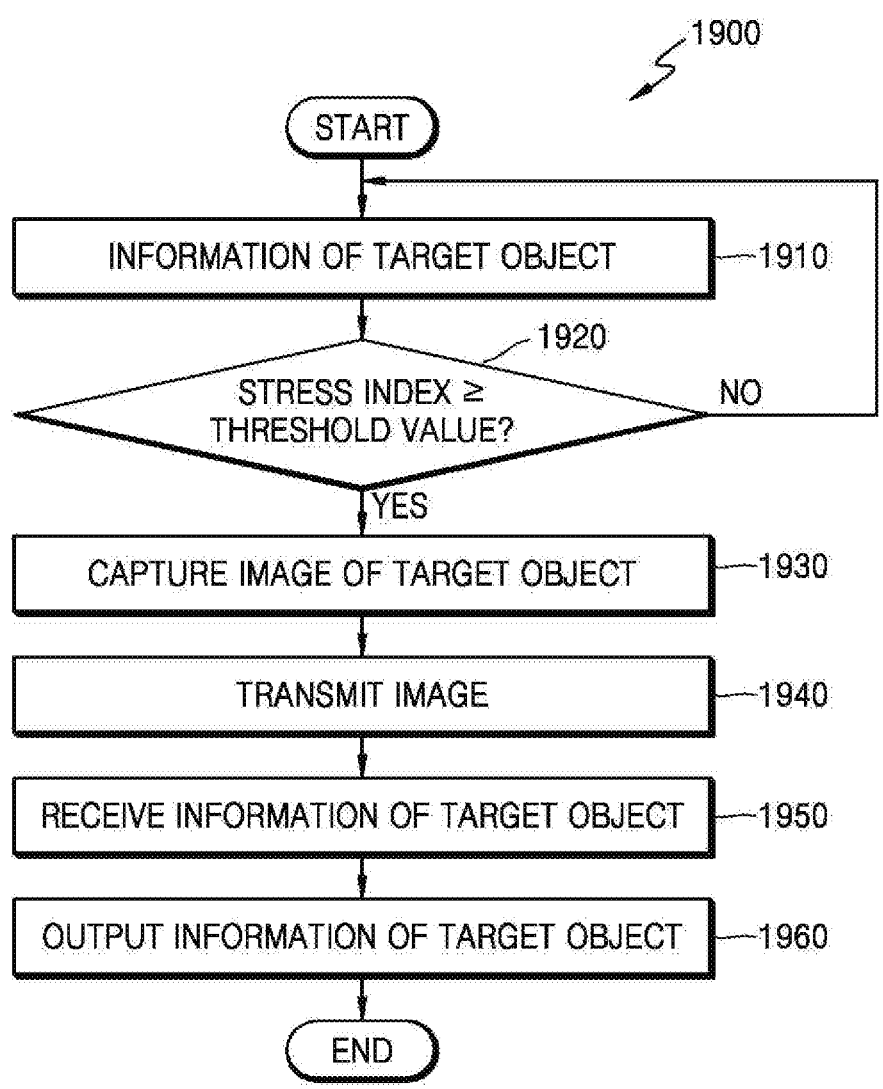
FIG. 19 is a flowchart of a method of capturing, by a device, an image of a target object, and searching for, by the device, the target object, according to an embodiment of the present disclosure.

FIG. 19 is a flowchart of a method 1900 of capturing, by the device 100, an image of the target object 1820, and searching for, by the device 100, the target object 1820, according to an embodiment of the present disclosure.

Since operations 1910 and 1920 may correspond to operations 210 and 220 of FIG. 2A, overlapping details thereof are not provided again.

In operation 1910, the device 100 may detect a bio-signal of the user 110.

In operation 1920, the device calculates a stress index of the user 110 based on the bio-signal of the user 110 and determine whether the stress index is equal to or higher than a threshold value.

When it is determined that the stress index is equal to or higher than the threshold value, the device 100 may capture an image of the target object 1820 in operation 1930. In operation 1940, the device 100 may transmit the captured image to the host device 1830. In operation 1950, the device 100 may receive information of the target object 1820 from the host device 1830. In operation 1960, the device 100 may output the received information of the target object 1820.

When the target object 1820 is an object around the device 100, the device 100 may output information of the object. The information of the object may be all or some information of the object. For example, the information of the object may include ID information and state information of the object, ID information and state information of a part of the object, guide information for executing a certain function of the object, and information about a method of controlling a part of the object.

For example, the device 100 may capture an image of a home-bar of a refrigerator when the stress index of the user 110 is equal to or higher than the threshold value. Then, the device 100 may transmit the image of the home-bar to the host device 1830. Also, the host device 1830 may search for the home-bar by comparing the received image of the home-bar with an image of the home-bar pre-stored in the host device 1830. Also, the host device 1830 may transmit information about a method of using the home-bar to the device 100.

As another example, the device 100 may capture an image of a displayer or UI unit capable of setting a temperature of a refrigerator when the stress index of the user 110 is equal to or higher than the threshold value. Then, the device 100 may transmit the captured image to the host device 1830. Also, the host device 1830 may search for the displayer or UI unit by comparing the captured image with an image of the displayer or UI unit pre-stored in the host device 1830. Also, the host device 1830 may transmit information about a method of adjusting a temperature of the refrigerator to the device 100.

The information of the object may be user information of the user 110 related to the object. For example, the user information may include schedule information or surrounding environment information of the user 110.

For example, the device 100 may capture an image of a calendar when the stress index of the user 110 is equal to or higher than the threshold value. Then, the device 100 may transmit the captured image to the host device 1830. The host device 1830 may search for the calendar by comparing the received image with an image of the calendar pre-stored in the host device 1830. Also, the host device 1830 may transmit recent schedule information to the device 100, and the device 100 may output the recent schedule information.

As another example, the device 100 may capture an image of a phone when the stress index of the user 110 is equal to or higher than the threshold value. Then, the device 100 may transmit the captured image to the host device 1830. Also, the host device 1830 may search for the phone by comparing the received image with an image of the phone pre-stored in the host device 1830. Also, the host device 1830 may transmit a phone number most frequently called (i.e., information of peripheral device) to the device 100.

Also, the device 100 may transmit an image obtained by capturing a plurality of devices to the host device 1830. Then, the host device 1830 may select a device on which an imaging unit is focused from among the plurality of devices and search for and identify the selected device. Also, the host device 1830 may transmit information of the selected device to the device 100.

When the target object 1820 is a person around the device 100, the device 100 may output information of the person. The information of the person may be profile information. The profile information may include a name, an age, an occupation, and a relation with the user 110 of the person. For example, the stress index of the user 110 may be equal to or higher than the threshold value since the user 110 is unable to recognize the person. The device 100 captures an image of the person and transmits the captured image to the host device 1830. The host device 1830 may search for and identify the person by comparing the captured image with an image of the person pre-stored in the host device 1830 or by using a face recognition function. The host device 1830 may transmit the profile information to the device 100. The device 100 may output the profile information.

Meanwhile, when the user 110 is to use a dangerous device, the device 100 according to an embodiment may alert the user 110 by outputting a warning signal. Also, the device 100 according to an embodiment may call a pre-set contact number to notify another person about a danger the user 110 is facing. Hereinafter, an operation of the device 100 outputting a warning signal or externally transmitting a notification will be described with reference to FIGS. 20 through 22.

Figure 20:
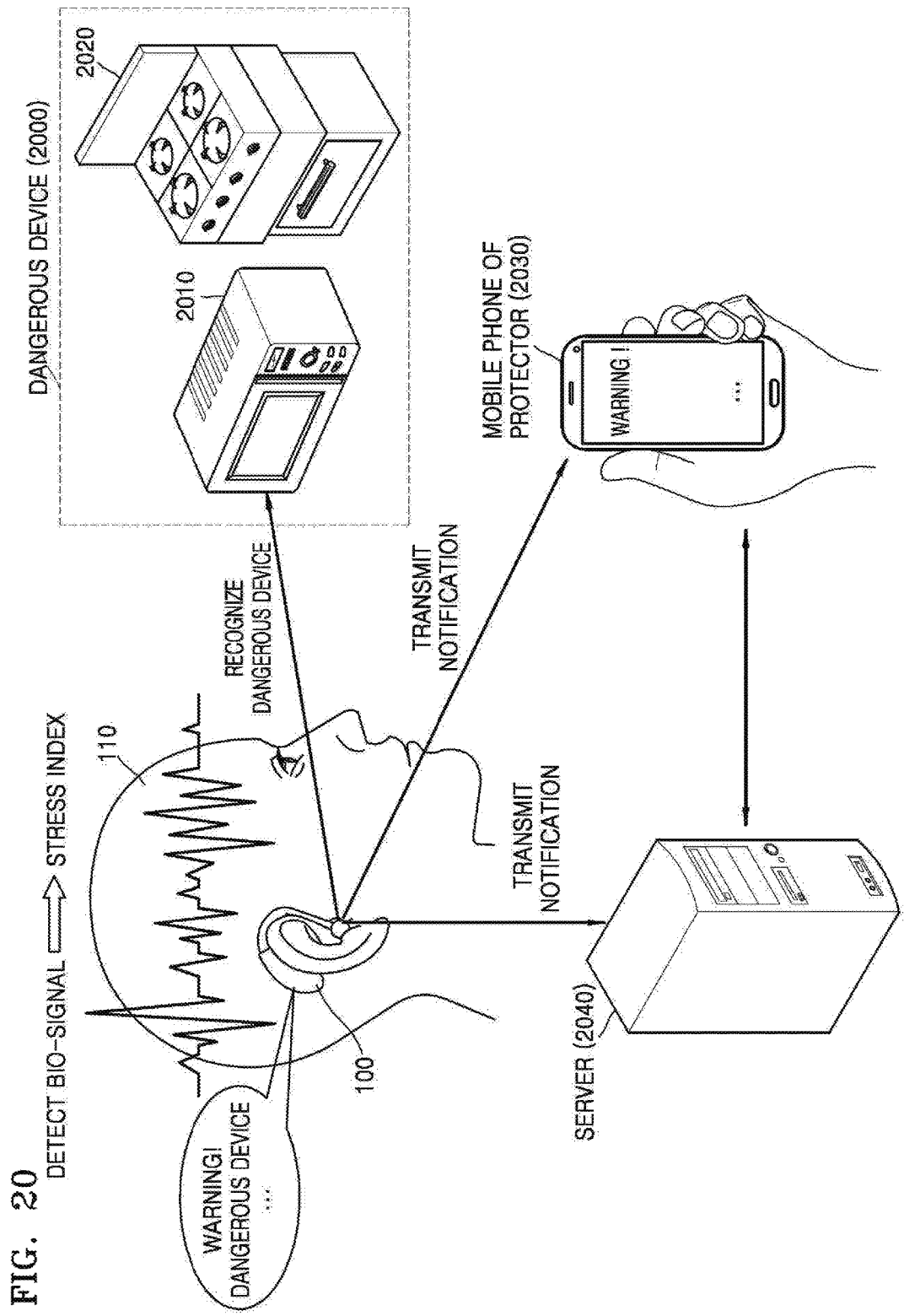
FIG. 20 is a diagram for describing a device selecting a dangerous device as a first device, and outputting a warning signal and information of the first device, according to an embodiment of the present disclosure.

FIG. 20 is a diagram for describing a device 100 selecting a dangerous device 2000 as a first device, and outputting a warning signal and information of the first device, according to an embodiment of the present disclosure.

Here, the dangerous device 2000 may be a device that may harm the user 110 if the user 110 is not well-acquainted with how to use the device.

The dangerous device 2000 may be pre-classified or pre-set by the user 110 by using the device 100. For example, the dangerous device 2000 may be a microwave 2010, a gas oven range 2020, or an electric heater (not shown).

When the selected first device is the dangerous device 2000, the device 100 may output a warning signal. Here, the warning signal may be a signal notifying the user 110 that the selected first device is the dangerous device 2000.

Also, when the selected first device is the dangerous device 2000, the device 100 may transmit a notification to a pre-set contact number. For example, the pre-set contact number may be a contact number of a protector or acquaintance of the user 110. The notification may be a message indicating that the user 110 may be in danger, and may be transmitted in a form of at least one of an email, an instant message, an image message, and a push notification. Content of the notification may include a name and type of the first device, and may include a name and type of stress detected from the user 110. Also, the content of the notification may include a time when the stress of the user 110 is detected.

For example, the device 100 may select the microwave 2010 as the first device. The microwave 2010 may be pre-set as a dangerous device in the device 100. Accordingly, the device 100 may output a voice signal of "Warning, it is dangerous device" as the warning signal. Also, after outputting the warning signal, the device 100 may output precautions while using the microwave 2010 and a method of operating the microwave 2010 (i.e., information of the first device). As described above, by outputting the warning signal, the device 100 may alert the user 110 about a danger. Also, the device 100 may transmit a notification to a mobile phone 2030 of a protector, wherein a phone number of the mobile phone 2030 is pre-set in the device 100. For example, the device 100 may transmit a text message to the mobile phone 2030. As described above, the device 100 may transmit the notification to the pre-set phone number to notify the protector about a dangerous situation of the user 110.

Figure 21:
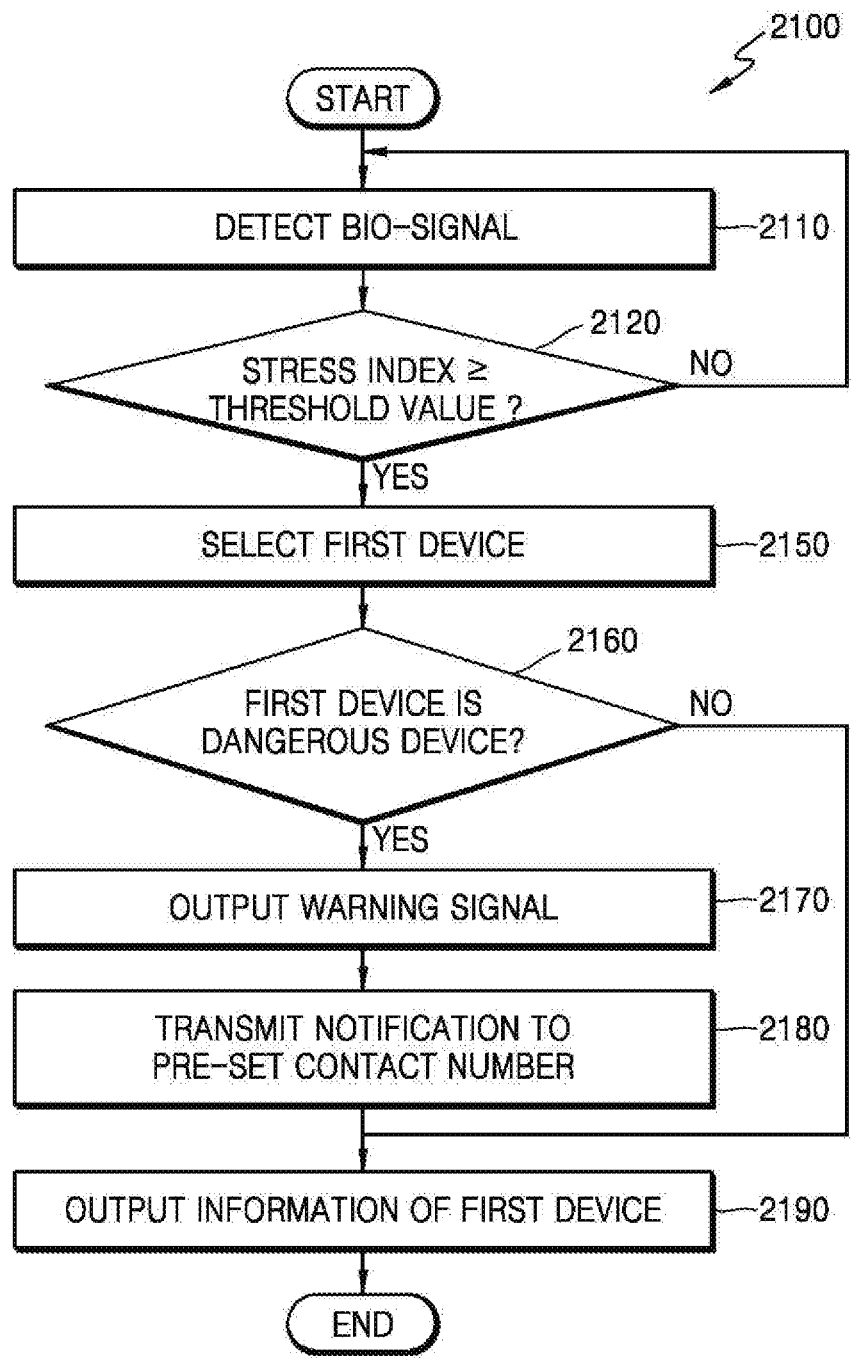
FIG. 21 is a flowchart of a method of selecting, by a device, a dangerous device as a first device, and outputting, by the device, a warning signal and information of the first device, according to an embodiment of the present disclosure.

FIG. 21 is a flowchart of a method 2100 of selecting, by the device 100, the dangerous device 2000 as a first device, and outputting, by the device 100, a warning signal and information of the first device, according to an embodiment of the present disclosure.

Since operations 2110, 2220, 2150, and 2190 may respectively correspond to operations 210*a*, 220*a*, 250*a*, and 260*a* of FIG. 2A, overlapping details thereof are not provided again.

In operation 2110, the device 100 may detect a bio-signal of the user 110. In operation 2120, the device 100 may calculate a stress index of the user 110 based on the bio-signal and determine whether the stress index is equal to or higher than a threshold value.

When it is determined that the stress index is equal to or higher than the threshold value, the device 100 may select a first device from among at least one peripheral device in operation 2150.

The device 100 may search for the at least one peripheral device by using any one of the methods described above with reference to FIGS. 1, 2A to 2D, 3, 4A and 4B, 5, 6A and 6B, 7 to 11, 12A and 12B, 13, 14, 15A and 15B, and 16 to 19. For example, the device 100 may search for the at least one peripheral device based on a search signal and a response signal. As another example, the device 100 may search for the at least one peripheral device based on an indoor location. As another example, the device 100 may search for the at least one peripheral device by capturing an image of the at least one peripheral device.

In operation 2160, the device 100 may determine whether the first device is the dangerous device 2000.

The device 100 may determine whether the first device is the dangerous device 2000 based on a database stored in the device 100. For example, the device 100 may pre-store a list of dangerous devices 2000. When the first device is included in the list of dangerous devices 2000, the device 100 may determine that the first device is the dangerous device 2000. The device 100 may register, edit, or delete the list based on a user input.

For example, as described above with reference to FIGS. 1, 2A to 2D, 3, 4A and 4B, 5, 6A and 6B, and 7, when the device 100 searches for a peripheral device based on a search signal and a response signal, the device 100 may compare ID information (for example, an ID of the first device) included in a response signal of the first device with the list pre-stored in the device 100. When it is determined that the first device is included in the list, the device 100 may determine that the first device is the dangerous device 2000.

As another example, as described above with reference to FIGS. 12A and 12B, 13, 14, 15A and 15B, 16, and 17, when the device 100 searches for a peripheral device based on an indoor location, the device 100 may compare ID information (for example, an ID of the first device) of the first device, which is pre-stored in the device 100, with the list pre-stored in the device 100. When it is determined that the first device is included in the list, the device 100 may determine that the first device is the dangerous device 2000.

The device may receive, from the first device, information indicating whether the first device is the dangerous device 2000.

For example, as described above with reference to FIGS. 1, 2A to 2D, 3, 4A and 4B, 5, 6A and 6B, and 7, when the device 100 searches for a peripheral device based on a search signal and a response signal, the device 100 may receive, from the first device, information indicating whether the first device is the dangerous device 2000.

The device 100 may receive the information indicating whether the first device is the dangerous device 2000 from the host device 1830.

For example, as described above with reference to FIGS. 18 and 19, when the device 100 searches for a peripheral device by capturing an image of the peripheral device, the device 100 may receive, from the host device 1830, information indicating whether the first device is the dangerous device 2000.

When it is determined that the first device is the dangerous device 2000 in operation 2160, the device 100 may output a warning signal in operation 2170. For example, the warning signal may include at least one of a visual signal, an auditory signal, a vibration signal, and a tactile signal. For example, the device 100 may output the warning signal in a form of at least one of voice, warning sound, siren, a text message, lighting, warning light, and vibration.

In operation 2180, the device 100 may transmit a notification to a pre-set contact number. For example, the device 100 may transmit the notification to a contact number of a protector. The device 100 may directly transmit the notification to the pre-set contact number. Alternatively, the device 100 may transmit the notification to the pre-set contact number through a server 2040.

Also, when it is determined that the first device is the dangerous device 2000, the device 100 may request the first device to output a warning signal. For example, the first device may transmit a danger signal to the user 110 and alert the user 110 by vibrating a button the user 110 pressed, sounding a siren, or turning on a light.

Also, when it is determined that the first device is the dangerous device 2000, the device 100 may request a second signal to output a warning signal. For example, the second device (for example, a wearable device worn on the user 110 or a peripheral device other than the first device) may transmit a danger signal to the user 110 and alert the user 110 by outputting a vibration signal, sounding a siren, or turning on a light.

In operation 2190, the device 100 may output information of the first device. For example, when it is determined that the first device is not the dangerous device 2000 in operation 2160, operations 2170 and 2180 may not be performed and operation 2190 may be performed. Also, when it is determined that the first device is the dangerous device 2000 in operation 2160, operations 2170 and 2180 may be performed and then operation 2190 may be performed.

In FIG. 21, operations 2170 through 2190 are illustrated to be sequentially performed, but an order of operations 2170 through 2190 may be changed. Also, operations 2170 through 2190 may be sequentially or simultaneously performed.

Figure 22:
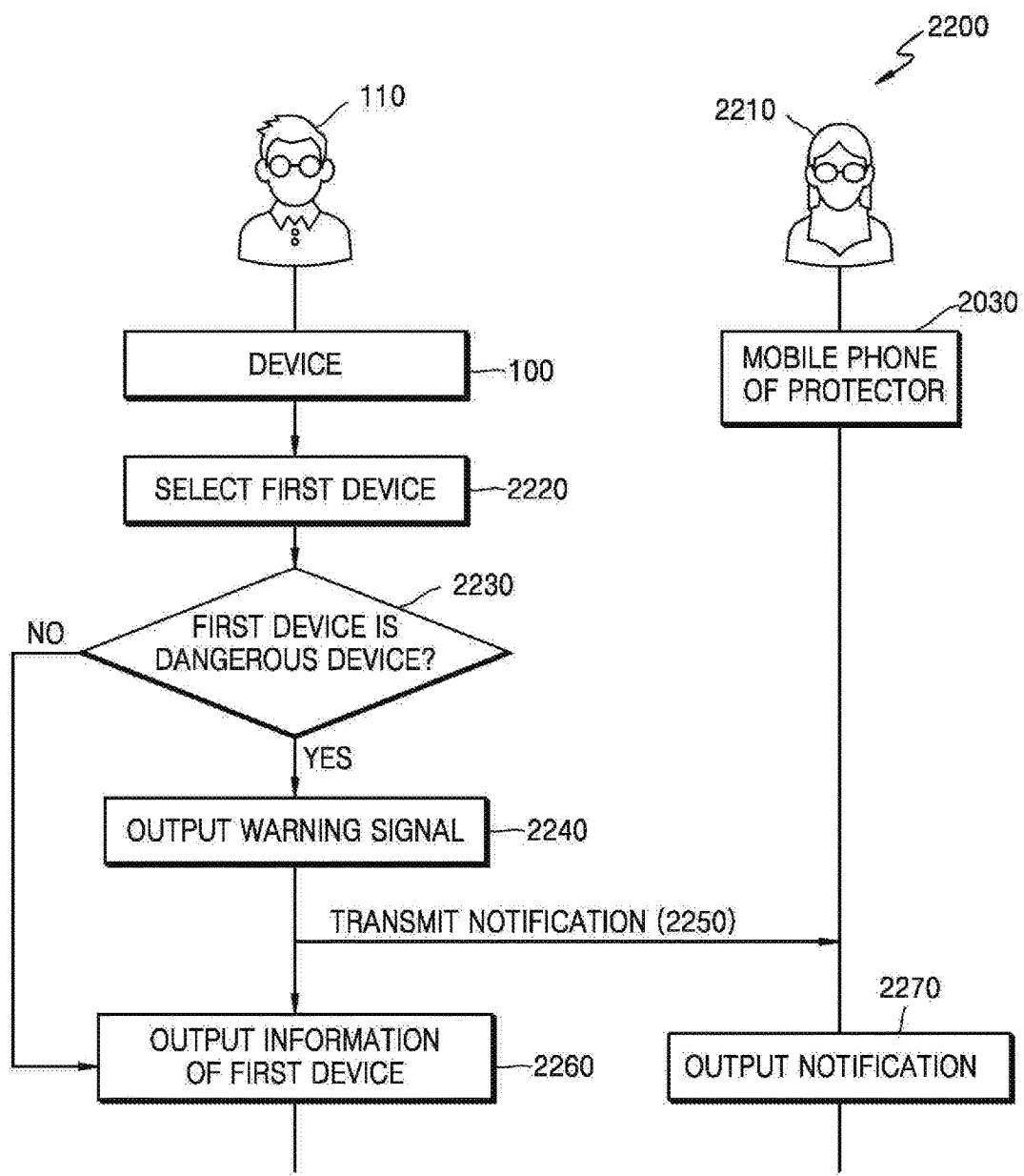
FIG. 22 is a flowchart of a method of selecting, by a device, a first device that is a dangerous device, and contacting a protector on a mobile phone, according to an embodiment of the present disclosure.

FIG. 22 is a flowchart of a method 2200 of selecting, by the device 100, a first device that is a dangerous device, and contacting a protector 2210 on the mobile phone 2030, according to an embodiment of the present disclosure.

After calculating a stress index of the user 110, the device 100 may select the first device in operation 2220. In operation 2230, the device 100 may determine whether the first device is a dangerous device. When it is determined that the first device is a dangerous device in operation 2230, the device 100 may output a warning signal in operation 2240, and transmit a notification to the mobile phone 2030 of the protector 2210 in operation 2250. Also, in operation 2260, the device 100 may output information of the first device. In operation 2270, the mobile phone 2030 of the protector 2210 may output the notification received in operation 2250.

Figure 23:
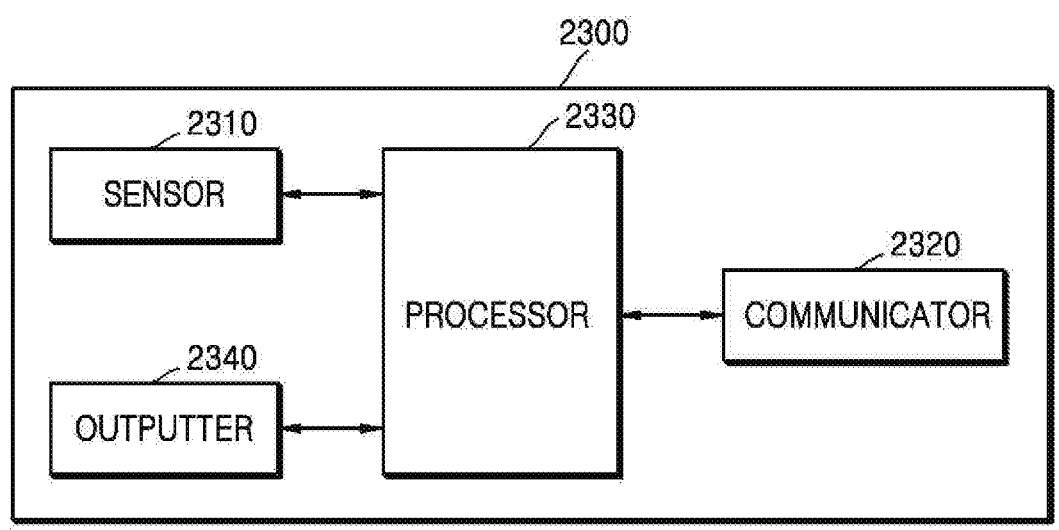
FIGS. 23 and 24 are block diagrams of devices outputting information of a peripheral device, according to various embodiments of the present disclosure.
Figure 24:
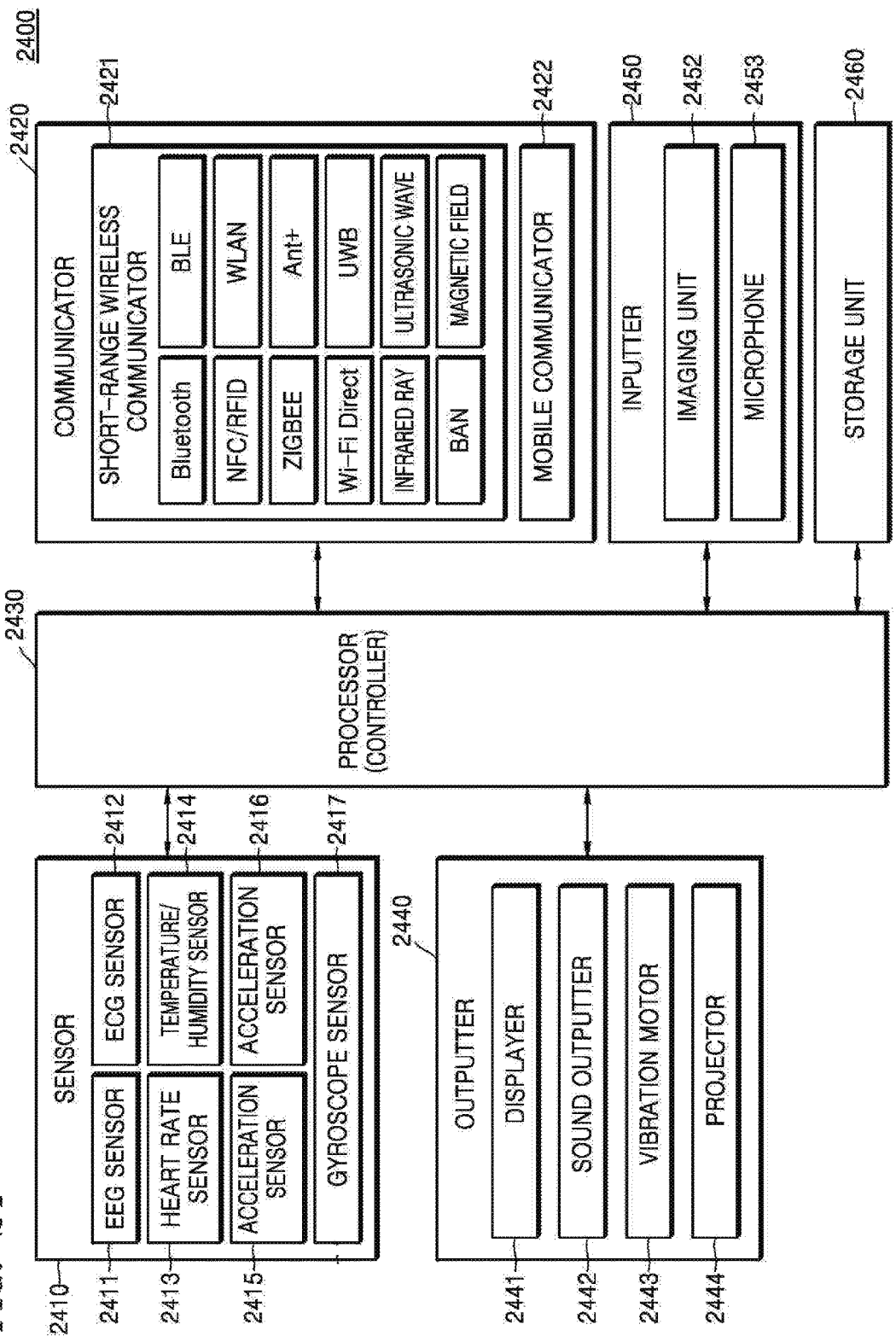

FIGS. 23 and 24 are block diagrams of devices 2300 and 2400 outputting information of a peripheral device, according to various embodiments of the present disclosure. The devices 2300 and 2400 of FIGS. 23 and 24 may correspond to the device 100 described above with reference to FIGS. 1, 2A to 2D, 3, 4A and 4B, 5, 6A and 6B, 7 to 11, 12A and 12B, 13, 14, 15A and 15B, and 16 to 22.

Referring to FIG. 23, the device 2300 according to an embodiment may include a sensor 2310, a communicator 2320, a processor 2330, and an outputter 2340.

Here, components of the device 2300 shown in FIG. 23 are not all essential. For example, the device 2300 may include more or less components than those shown in FIG. 23.

For example, referring to FIG. 24, the device 2400 may further include an inputter 2450 and a storage unit 2460 compared to the device 2300 of FIG. 23.

Sensors 2310 and 2410 may detect a state of the devices 2300 and 2400 or a state around the devices 2300 and 2400, and transmit the detected state to processors 2330 and 2430.

The sensors 2310 and 2410 may include at least one of an EEG sensor 2411, an ECG sensor 2412, a heart rate sensor 2413, a temperature/humidity sensor 2414, an acceleration sensor 2415, a magnetic sensor 2416, and a gyroscope sensor 2417, but are not limited thereto. Since functions of each sensor may be intuitively inferred by one of ordinary skill in the art based on its name, details thereof are not provided herein.

For example, the sensors 2310 and 2410 may detect a bio-signal of a user.

Also, the sensors 2310 and 2410 may detect a direction of the devices 2300 and 2400.

Also, the sensors 2310 and 2410 may detect magnetic fields around the devices 2300 and 2400.

Communicators 2320 and 2420 may include at least one component enabling data communication between the devices 2300 and 2400 and another device, or between the devices 2300 and 2400 and a server. For example, the communicators 2320 and 2420 may include a short-range wireless communicator 2421 and a mobile communicator 2422.

The short-range wireless communicator 2421 may include a BT communicator, a BLE communicator, a near field communicator, a wireless local area network (WLAN), a Wi-Fi communicator, a ZigBee communicator, an infrared data association (IrDA) communicator, a Wi-Fi direct (WFD) communicator, an UWB communicator, an Ant+ communicator, an infrared communicator, an ultrasonic communicator, a BAN communicator, and a magnetic field communicator, but components included in the short-range wireless communication unit 2421 are not limited thereto.

The mobile communication unit 2422 transmits and receives a wireless signal to and from at least one of a base station, an external terminal, and a server, on a mobile communication network. Here, a wireless signal may include data having various formats according to transmission and reception of a voice call signal, a video telephone call signal, or a text/multimedia message.

For example, the communicators 2320 and 2420 may transmit a search signal to at least one peripheral device, and receive at least one response signal from the at least one peripheral device.

Also, the communicators 2320 and 2420 may transmit the search signal in a direction pre-set based on the devices 2300 and 2400.

Also, the communicators 2320 and 2420 may request a first device to output information of the first device.

Also, the communicators 2320 and 2420 may receive at least one node signal from at least one node.

Also, the communicators 2320 and 2420 may transmit an image of a peripheral device to a host device, and receive information of the peripheral device from the host device.

Also, the communicators 2420 and 2420 may transmit a notification to a pre-set contact number.

The processors 2330 and 2430 generally control overall operations of the devices 2300 and 2400. For example, the processors 2330 and 2430 may control the sensors 2310 and 2410, the communicators 2320 and 2420, outputters 2340 and 2440, and inputter 2450 by executing programs stored in the storage unit 2460.

For example, the processors 2330 and 2430 may calculate a stress index of the user based on the bio-signal of the user.

Also, the processors 2330 and 2430 may search for the at least one peripheral device based on a search signal and a response signal. Also, the processors 2330 and 2430 may select the first device from the at least one peripheral device based on signal strength of the response signal and directions of the devices 2300 and 2400.

Also, the processors 2330 and 2430 may determine indoor locations of the devices 2300 and 2400 based on an indoor location of at least one node and signal strength of at least one node signal.

Also, the processors 2300 and 2430 may determine the indoor locations of the devices 2300 and 2400 based on magnetic fields around the devices 2300 and 2400.

Also, the processors 2330 and 2430 may select the first device from among the at least one peripheral device based on the indoor locations of the devices 2300 and 2400.

Also, the processors 2300 and 2430 may search for a person or object included in an image including the person or object, by using the image.

The outputters 2340 and 2440 may output an audio signal, a video signal, or a vibration signal, and may include a displayer 2441, a sound outputter 2442, a vibration motor 2443, and a projector 2444.

The displayer 2441 displays information processed by the devices 2300 and 2400. For example, the displayer 2441 may display a UI for selecting a virtual image or a UI for setting an operation of a virtual image.

Meanwhile, when the displayer 2441 is configured as a touch screen by forming a layer structure with a touch pad, the displayer 2441 may also be used as an input device as well as an output device. The displayer 2441 may include at least one of a liquid crystal display (LCD), a thin-film transistor-liquid crystal display (TFT-LCD), an organic light-emitting diode (OLED), a flexible display, a three dimensional (3D) display, and an electrophoretic display. According to an embodiment, the devices 2300 and 2400 may include at least two displayers 2441. Here, the at least two displayers 2441 may be disposed to face each other by using a hinge.

The sound outputter 2442 outputs audio data received from the communicators 2320 and 2420 or stored in the storage unit 2460. Also, the sound outputters 2442 outputs a sound signal related to a function performed by the devices 2300 and 2400, such as a call signal reception sound, a message reception sound, or a notification sound. The sound outputter 2442 may include a speaker or a buzzer.

The vibration motor 2443 may output a vibration signal. For example, the vibration motor 2443 may output a vibration signal corresponding to an output of audio data or video data, for example, a call signal reception sound or a message reception sound. Also, the vibration motor 2443 may output a vibration signal when a touch screen is touched.

The projector 2444 may externally output visual information. For example, the projector 2444 may externally project a character, a number, a photograph, a still image, or a moving image on a wall, a paper, a desk, a table, or skin of the user.

For example, the outputters 2340 and 2440 may output information of a peripheral device. Also, the outputters 2430 and 2440 may output a warning signal. For example, the sound outputter 2442 may output information of a peripheral device and a warning signal in at least one of voice and sound.

The inputter 2450 may be a unit into which the user inputs data for controlling the devices 2300 and 2400. Examples of the inputter 2450 include a keypad, a dome switch, a touch pad (a touch capacitance type, a pressure resistance film type, an infrared light detecting type, a surface ultrasound conducting type, an integral tension measuring type, or a piezo-effect type), a jog wheel, and a jog switch, but are not limited thereto.

For example, the inputter 2450 may receive a user input for searching for a peripheral device.

Also, the inputter 2450 may include an imaging unit 2452 and a microphone 2453 for respectively receiving an audio signal and a video signal. The imaging unit 2452 may obtain an image frame of a still image or a moving image through an image sensor. An image captured by the image sensor may be processed by the processors 2330 and 2430 or a separate image processor (not shown).

An image frame processed by the imaging unit 2452 may be stored in the storage unit 2460 or transmitted to an external device through the communicators 2320 and 2420. According to an embodiment, the devices 2300 and 2400 may include at least two imaging units 2452.

For example, the imaging unit 2452 may capture an image of a surrounding person or object when it is determined that the user is stressed.

The microphone 2453 receives an external sound signal and processes the external sound signal to electric voice data. For example, the microphone 2453 may receive a sound signal from an external device or the user. The microphone 2453 may use any one of various noise removing algorithms to remove noise generated while receiving the external sound signal.

For example, the microphone 2453 may receive a voice input of the user for searching for a peripheral device.

The storage unit 2460 may include at least one type of storage medium from among a flash memory, a hard disk, a multimedia card micro type memory, a card type memory (for example, a secure digital (SD) card or an extreme digital (XD) card), random access memory (RAM), static RAM (SRAM), read-only memory (ROM), electrically erasable programmable ROM (EEPROM), programmable ROM (PROM), a magnetic memory, a magnetic disk, and an optical disk.

The storage unit 2460 may store programs for processes or control of the processors 2330 and 2430, or may store data input to or output from the devices 2300 and 2400.

For example, the storage unit 2460 may store indoor locations of at least one peripheral device and at least one node.

Also, the storage unit 2460 may store a node signal strength finger print map according to indoor locations. Also, the storage unit 2460 may store a terrestrial magnetic finger print map according to indoor locations.

Also, the storage unit 2460 may store information about a history of the user selecting a first device.

Also, the storage unit 2460 may store a list of dangerous devices.

Figure 25:
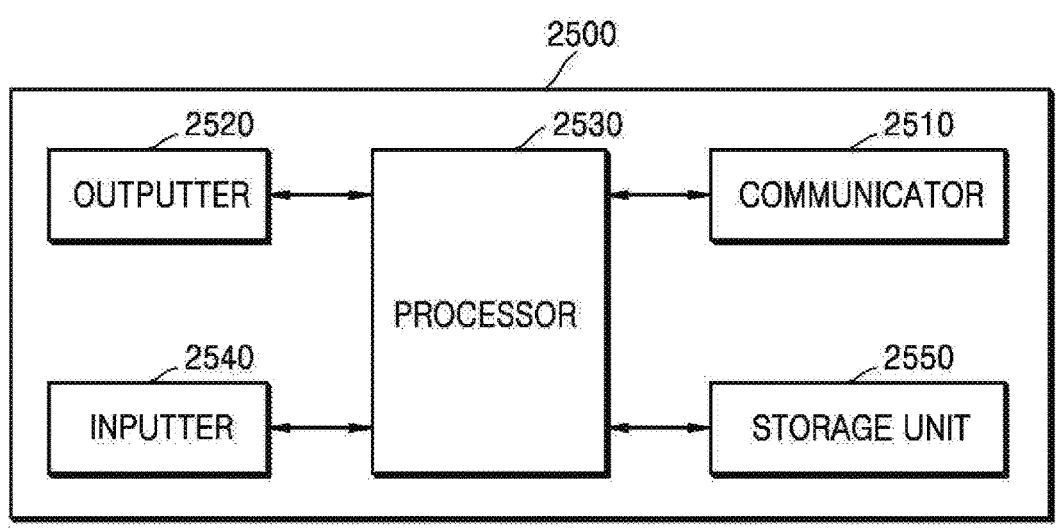
FIG. 25 is a block diagram of a home device according to an embodiment of the present disclosure.

FIG. 25 is a block diagram of a home device 2500 according to an embodiment of the present disclosure.

Here, the home device 2500 may correspond to a peripheral device described above with reference to FIGS. 1, 2A to 2D, 3, 4A, 4B, 5, 6A, 6B, 7 to 11, 12A, 12B, 13, 14, 15A, 15B, and 16 to 24. For example, the home device 2500 may include at least one of the peripheral device 120 of FIG. 1, the washing machine 420, the TV 430, and the refrigerator 440 of FIG. 4A, the washing machine 620, the TV 630, and the refrigerator 640 of FIG. 6A, the at least one peripheral device 820 of FIG. 8, the washing machine 1020 of FIG. 10, the washing machine 1250 and the TV 1260 of FIG. 12A, the washing machine 1550 and the TV 1560 of FIG. 15A, the target object 1820 of FIG. 18, and the dangerous device 2000 of FIG. 20. Thus, details about the home device 2500 overlapping those of FIGS. 1, 2A to 2D, 3, 4A, 4B, 5, 6A, 6B, 7 to 11, 12A, 12B, 13, 14, 15A, 15B, and 16 to 24 are not provided again.

Referring to FIG. 25, the home device 2500 according to an embodiment may include a communicator 2510, a processor 2530, and an outputter 2520.

The components shown in FIG. 25 are not all essential components of the home device 2500. The home device 2500 may include more or less components than those shown in FIG. 25.

For example, the home device 2500 may further include an inputter 2540 and a storage unit 2550.

When the communicator 2510 receives a request to output information of the home device 2500 from the device 100, the outputter 2520 may output the information of the home device 2500. For example, the home device 2500 may output the information of the home device 2500 in at least one of visual information, auditory information, and vibration information. For example, the home device 2500 may output the information of the home device 2500 in at least one of a character, an image, sound, and voice.

The processor 2530 controls overall operations of the home device 2500 in general. For example, the processor 2530 may generally control the communicator 2510 and the outputter 2520 by executing programs stored in the storage unit 2550.

Also, the inputter 2540 may be a unit into which a user inputs data for controlling the home device 2500. Examples of the inputter 2540 include a keypad, a dome switch, a touch pad (a touch capacitance type, a pressure resistance film type, an infrared light detecting type, a surface ultrasound conducting type, an integral tension measuring type, or a piezo-effect type), a jog wheel, and a jog switch, but are not limited thereto.

Also, the inputter 2540 may include an imaging unit and a microphone for respectively receiving an audio signal and a video signal. The imaging unit 2541 may obtain an image frame of a still image or a moving image through an image sensor. An image captured by the image sensor may be processed by the processor 2530 or a separate image processor (not shown).

An image frame processed by the imaging unit 2541 may be stored in the storage unit 2550 or transmitted to an external device through the communicator 2510. According to an embodiment, the home device 2500 may include at least two imaging units 2541.

For example, the imaging unit 2541 may capture an image of the user 110 upon receiving a search signal from the device 2300 or 2400.

The microphone 2542 receives an external sound signal and processes the external sound signal to electric voice data. For example, the microphone 2542 may receive a sound signal from an external device or the user. The microphone 2542 may use any one of various noise removing algorithms to remove noise generated while receiving the external sound signal.

For example, the microphone 2542 may receive a voice input of the user.

The storage unit 2550 may store programs for processes and control of the processor 2530, and may store data input to or output from the home device 2500.

The storage unit 2550 may include at least one type of storage medium from among a flash memory, a hard disk, a multimedia card micro type memory, a card type memory (for example, a SD card or an XD card), RAM, SRAM, ROM, EEPROM, PROM, a magnetic memory, a magnetic disk, and an optical disk.

The embodiments may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., compact disc ROM (CD-ROM), or digital versatile disc (DVD)), etc.

According to one or more embodiments, the device 100 may detect a stress of the user 110 and provide information of a peripheral device that is an interest to the user 110. Accordingly, the device 100 according to an embodiment may help the user 110 who is a dementia patient to maintain a normal life without help from other people despite of memory loss of the user 110.

It should be understood that embodiments described herein should be considered in a descriptive sense only and not for purposes of limitation. Descriptions of features or aspects within each embodiment should typically be considered as available for other similar features or aspects in other embodiments.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A device comprising:
a sensor configured to detect a bio-signal of a user;
a communicator configured to communicate with at least one peripheral device;
a processor configured to:
calculate a stress index of the user based on the bio-signal, and
based on the stress index being equal to or higher than a threshold value, search for the at least one peripheral device and select a first device from among the at least one peripheral device within a certain range based on a direction of the device; and
an outputter configured to output information of the first device,
wherein the processor is further configured to:
control the communicator to transmit a search signal to the at least one peripheral device, and
search for the at least one peripheral device in response to receiving at least one response signal from at least one peripheral device.

2. The device of claim 1, wherein the processor is further configured to control the communicator to transmit the search signal in a pre-set direction.

3. The device of claim 1, wherein the bio-signal comprises electroencephalography (EEG).

4. The device of claim 1, wherein the processor is further configured to control the outputter to output the information of the first device as at least one of visual information and auditory information.

5. The device of claim 1, wherein the information of the first device comprises guide information corresponding to execution of a function of the first device.

6. The device of claim 1, wherein, when the first device is a pre-classified dangerous device, the processor is further configured to control the outputter to output a warning signal.

7. The device of claim 1, wherein, when the first device is a pre-classified dangerous device, the processor is further configured to control the communicator to transmit a notification to a pre-set contact number.

8. A method for operating a device, the method comprising:
   detecting, by a sensor, a bio-signal of a user;
   calculating, by a processor, a stress index of the user based on the bio-signal;
   based on the stress index being equal to or higher than a threshold value, transmitting a search signal to at least one peripheral device and searching for the at least one peripheral device in response to receiving at least one response signal from the at least one peripheral device;
   selecting, by the processor, a first device from among the at least one peripheral device within a certain range based on a direction of the device; and
   outputting, by an outputter, information of the first device.

9. The method of claim 8, wherein the search signal is transmitted in a pre-set direction.

10. The method of claim 8, wherein the bio-signal comprises electroencephalography (EEG).

11. The method of claim 8, wherein the information of the first device is output as at least one of voice or sound.

12. The method of claim 8, wherein the information of the first device comprises guide information corresponding to execution of a function of the first device.

13. The method of claim 8, further comprising, when the first device is a pre-classified dangerous device, outputting a warning signal.

14. The method of claim 8, further comprising, when the first device is a pre-classified dangerous device, transmitting a notification to a pre-set contact number.

* * * * *